United States Patent [19]

Wadaka et al.

[11] Patent Number: 5,272,923

[45] Date of Patent: Dec. 28, 1993

[54] INSPECTION APPARATUS

[75] Inventors: Shusou Wadaka; Tsutomu Nagatsuka; Koichiro Misu; Mitsuhiro Koike, all of Kanagawa, Japan

[73] Assignee: Mitsubishi Denki Kabushiki Kaisha, Tokyo, Japan

[21] Appl. No.: 691,063

[22] Filed: Apr. 23, 1991

[30] Foreign Application Priority Data

| Apr. 27, 1990 [JP] | Japan | 2-109988 |
| Apr. 27, 1990 [JP] | Japan | 2-109989 |
| Apr. 27, 1990 [JP] | Japan | 2-109990 |

[51] Int. Cl.$^5$ ............................................ G01N 29/22
[52] U.S. Cl. ................................ 73/602; 364/728.03; 364/728.07; 364/819; 367/125; 367/126
[58] Field of Search ............... 73/602, 642, 626, 631; 364/728.07, 728.03, 819, 821, 507, 508, 496, 497; 367/100, 124, 125, 126, 905

[56] References Cited

U.S. PATENT DOCUMENTS

| 2,907,400 | 10/1959 | Swafford, Jr. | 364/819 |
| 3,763,465 | 10/1973 | Tatge et al. | 367/125 |
| 3,968,471 | 7/1976 | Savit | 364/728.03 |
| 4,156,876 | 5/1979 | Debuisser | 364/728.07 |
| 4,198,704 | 4/1980 | Munson | 367/125 |
| 4,224,679 | 9/1950 | Nossen et al. | 364/728.03 |
| 4,245,326 | 1/1981 | Gutleber | 364/728.07 |
| 4,471,785 | 9/1984 | Wilson et al. | 73/602 |
| 4,542,653 | 9/1985 | Liu | 73/626 |
| 5,000,183 | 3/1991 | Bonnefous | 73/602 |
| 5,043,951 | 8/1991 | Gilmour et al. | 367/126 |
| 5,060,515 | 10/1991 | Kanda et al. | 73/602 |
| 5,065,629 | 11/1991 | Koike et al. | 73/602 |
| 5,203,823 | 4/1993 | Wadaka et al. | 73/602 |

OTHER PUBLICATIONS von M. Platte, "Barker-codierte Mehrschichtwandler aus Polyvinyl-idenflurid...," Acustica, vol. 56 (1984), pp. 29–33. (German).

K. M. Sung, "Piezoelectric Multilayer Transducers...," 366 Ultrasonics vol. 22 (1984) Mar., No. 2, Guildford, Surrey, Great Britain.

B. B. Lee and E. S. Fergason, "Time Gain Control in Spread Ultrasound," vol. 18, No. 3, May 1980, pp. 136–137.

Ultrasonic Testing of Materials, by Nihon Moritsu Kyokai, Feb. 25, 1980, pp. 177–181, pp. 296–298 (Japanese).

Golay, M. "Complementary Series," IRE Transactions on Information Theory, vol. IT-7, Apr. 1961 (pp. 82–87).

"Construction and Mode of Operation of a Pulse-Edge Instrument," and Chapter 17, pp. 205–210, 344–347, translation of Reference 4.

Primary Examiner—Hezron E. Williams
Assistant Examiner—Rose M. Finley
Attorney, Agent, or Firm—Wolf, Greenfield & Sacks

[57] ABSTRACT

An inspection apparatus utilizing a pulse compression technique is described which comprises a signal generator, a transmission/reception probe; first and second correlators and an adder. The signal generator generates a composite transmission signal consisting of signals Sap(t), Saq(t), Sbp(t) and Sbq(t) respectively based on a basic unit signal ga(t) and a sequence {p}, the signal ga(t) and a sequence {q}, a basic unit signal gb(t) and the sequence {p}, and the signal gb(t) and the sequence {q}, to the probe to transmit the composite transmission signal to a target. The first correlator performs a correlation operation of echo signals Rap(t), Raq(t), Rbp(t) and Rbq(t) corresponding to the signal Sap(t), Saq(t) and Sbq(t) by utilizing reference signals Ua(t) and Ub(t) based on the sequences to provide results Caap(t), Caaq(t), Cbbp(t) and Cbbq(t). The second correlator performs a correlation operation of the results Caap(t), Caaq(t) Cbbp(t) and Cbbq(t) by utilizing the sequences {p} and {q} to provide compressed pulses Caapp(t), Caaqq(t), Cbbpp(t) and Cbbqq(t). These pulses are summed up at the adder to provide a composite compressed pulse C having the large amplitude main lobe and small amplitude side lobes.

36 Claims, 41 Drawing Sheets

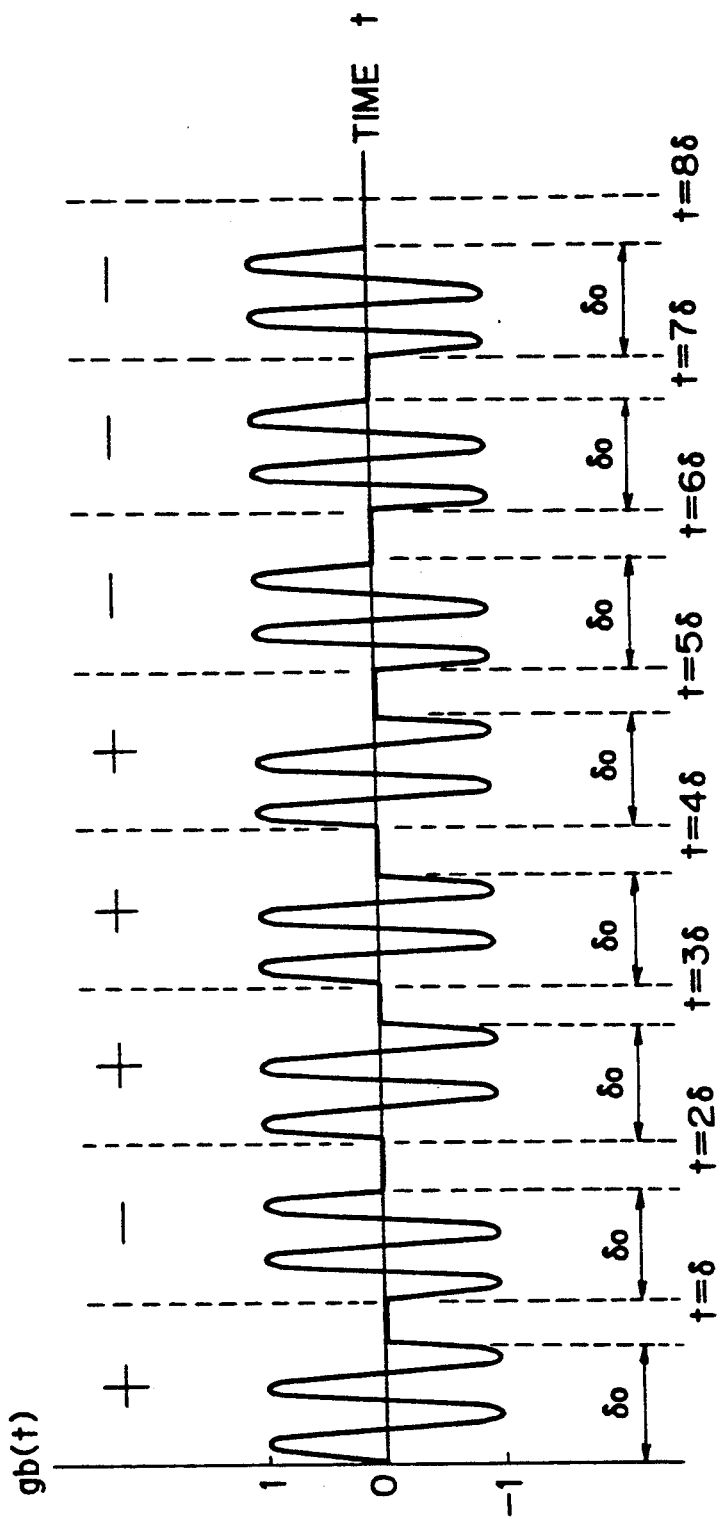

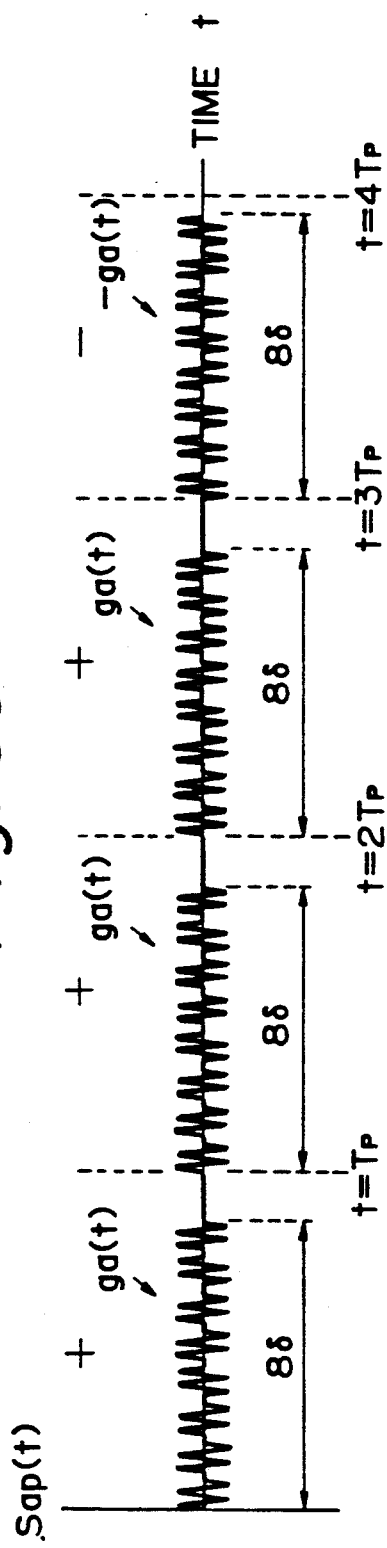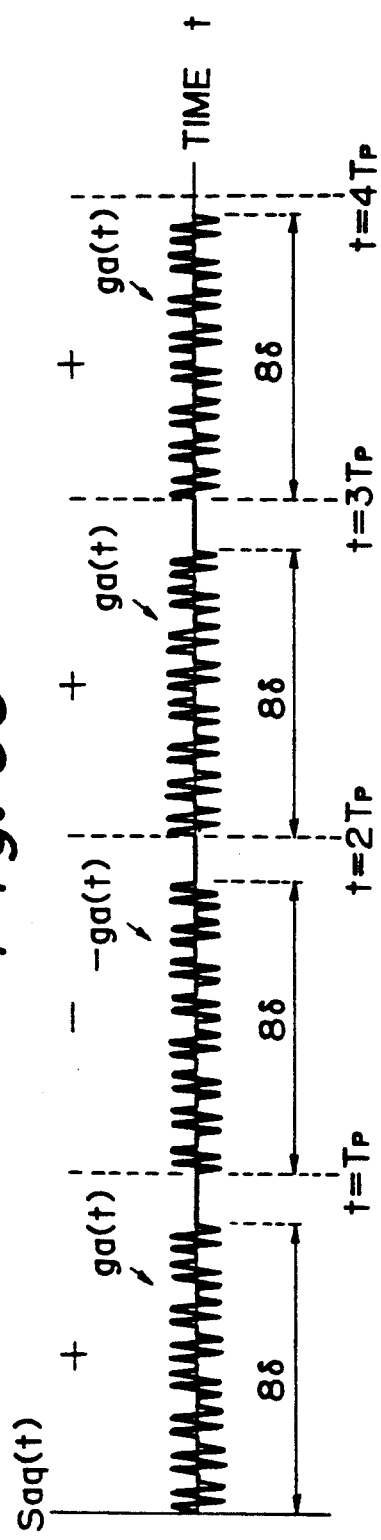

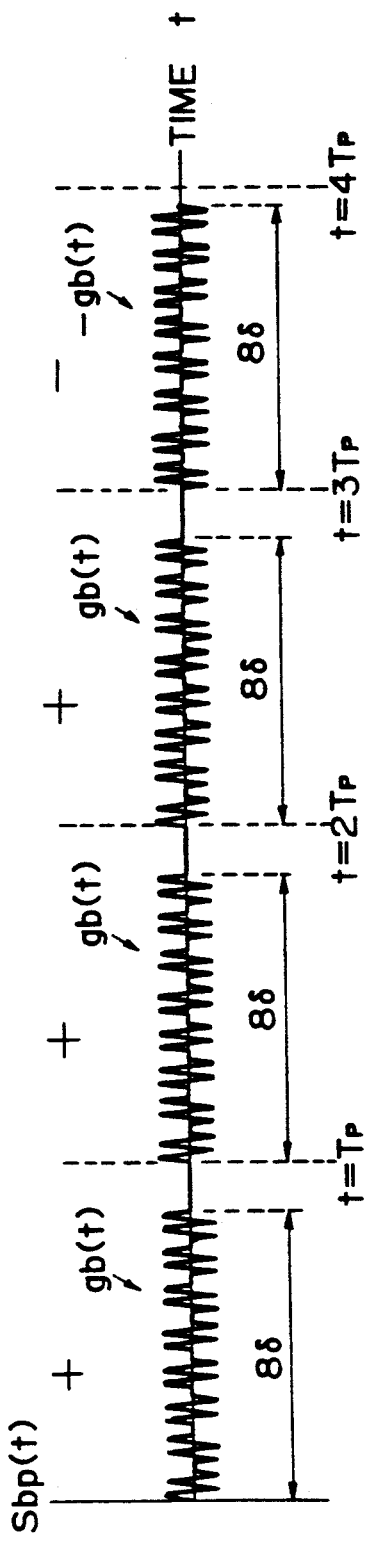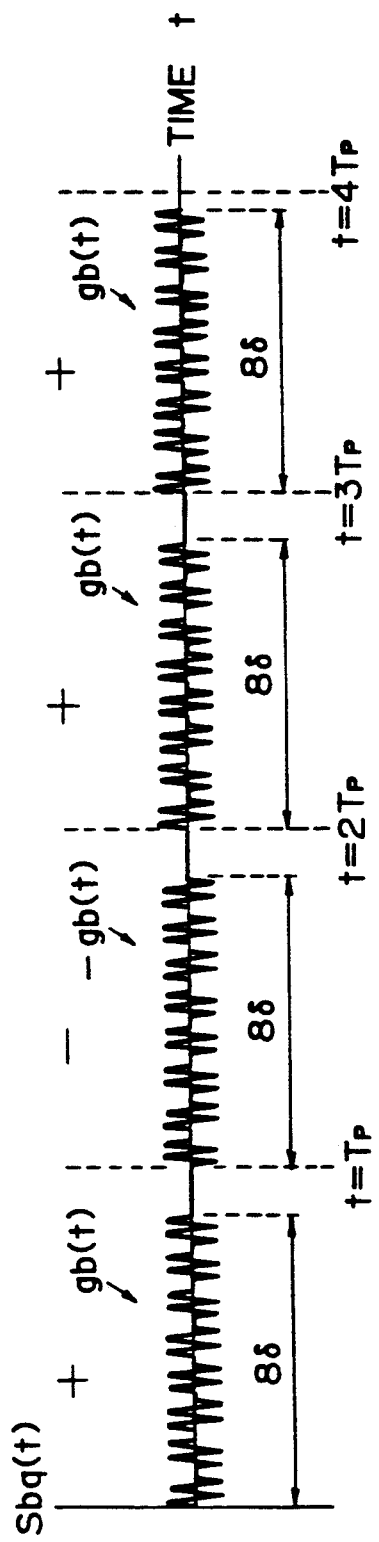

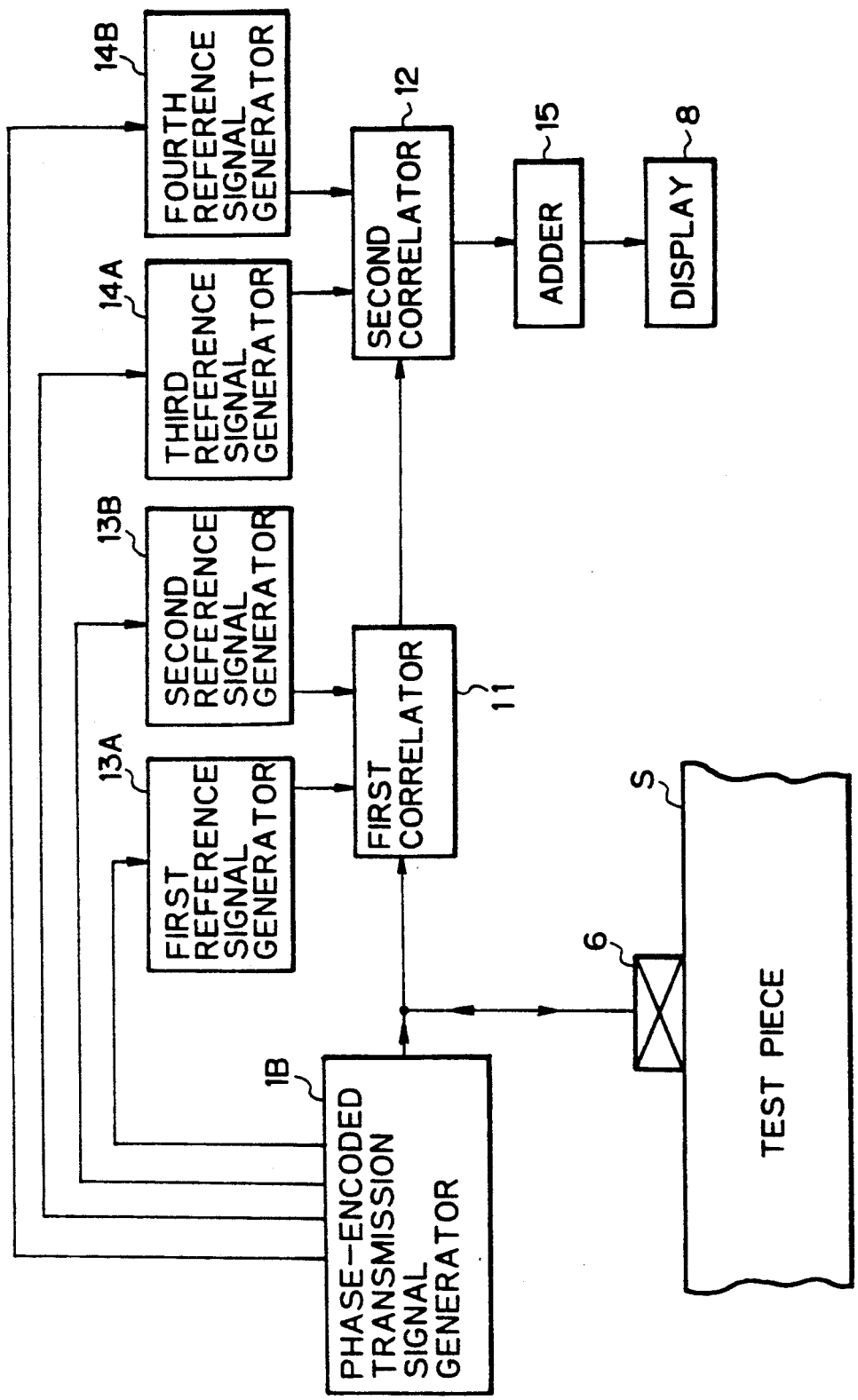

INSPECTION APPARATUS

BACKGROUND OF THE INVENTION

1. Field of the invention

The present invention relates to an inspection apparatus utilizing ultrasonic waves, electromagnetic waves or the like, and more particularly, relates to an inspection apparatus such as an ultrasonic non-destructive inspection apparatus utilizing a pulse compression method.

2. Prior Art

Conventional inspection apparatuses of the type explained above are disclosed, for example, in literatures A, B, C as listed below.

Literature A: B. B. Lee and E. S. Furgason, "High-Speed Digital Golay Code Flaw Detection System", in proceedings of IEEE Ultrasonics Symposium, 1981, pp 888 –891.

Literature B: B. B. Lee and E. S. Furgason, "An Evaluation of Ultrasound NDE Correlation Flaw Detection Systems", IEEE Transactions on Sonics and Ultrasonics, Vol. SU-29, No. 6, November, 1982, pp 359-369.

Literature C: B. B. Lee and E. S. Furgason, "High-Speed Digital Golay Code Flaw Detection System", Ultrasonics, July, 1983, pp 153-161.

The construction of a prior art will now be explained by referring to FIG. 1.

FIG. 1 is a block diagram illustrating an inspection apparatus utilizing ultrasonic waves as shown in the above Literature C. The inspection apparatus in FIG. 1 comprises a signal source 1, a digital delay line 2 indirectly connected to the signal source 1, a bipolar converter 3 indirectly connected to the signal source 1 and the digital delay line 2, a transmitter 4 connected to the bipolar converter 3, a bipolar converter 5 indirectly connected also to the signal source 1 and the digital delay line 2, an ultrasonic probe 6, an analog correlator 7 connected to the ultrasonic probe 6, the transmitter 4 and the bipolar converter 5, a display 8 connected to the analog correlator 7, and a system control unit 9.

It is to be noted that the ultrasonic probe 6 is submerged in a water vessel and a target S to be inspected is disposed at the location opposedly facing the ultrasonic probe 6 in the water vessel. It is also to be noted that the analog correlator 7 consists of a multiplier 7a connected to the ultrasonic probe 6 and the bipolar converter 5 and an integrator 7b connected to the multiplier 7a. Furthermore, logic circuits such as NAND gate and the like are interposed between the signal source 1 and the bipolar converters 3 and 5 as well as between the digital delay line 2 and the bipolar converters 3 and 5. The system control unit is connected to the respective elements as described above to control the system.

Operation of the prior art as shown in FIG. 1 will now be explained by referring to FIGS. 2 and 3.

FIGS. 2 and 3 are waveform diagrams respectively illustrating a transmission signal and a compressed pulse signal provided by the inspection apparatus as disclosed in Literature B.

In FIG. 2, the abscissa is illustrated in the unit of bits and if the unit time is regarded to correspond to the unit of bits, the unit of the abscissa can be taken as the time unit. In Literature B, the unit time corresponding to the unit bit is expressed by $\delta$. Therefore, the pulse duration of the transmission signal in FIG. 2 is $63 \times \delta$.

This transmission signal comprises a signal having a frequency of the base band, and an amplitude of which has been encoded by a special sequence. Encoding of the amplitude will be explained later and the sequence utilized for encoding will be firstly explained.

The utilized sequence is a finite length sequence which has been provided by taking out one cycle of the maximal length sequence (M-sequence) which is a cyclic sequence having a cyclic length of 63 bits.

The M-sequence is described in detail in "Coding Theory" coauthored by Hiroshi Miyagawa, Yoshihiro Iwatare and Hideki Imai, published on Jun. 29, 1979 by Shoukoudo, pp 474–499 (to be referred to a Literature D).

The M-sequence is a cyclic sequence having an infinite length and is a binary sequence components of which are comprised of two elements. The two elements may be allocated with symbols (+) and (−), numeral values +1 and −1 or numeric values 1 and 0 depending on the cases. In the example shown in FIG. 2, a finite length sequence is provided by using one cycle of the M-sequence having the cyclic length of 63 bits and a infinite length.

Encoding of the amplitude of the signal by utilizing this one cycle of M-sequence, or finite length sequence will next be explained.

By providing one element of the finite length sequence with the amplitude +1 and the other element with the amplitude −1, the amplitude for each unit time $\delta$ is modulated with +1 by the relative value in the order of appearance of these two elements of the sequence. The modulated signal may be called an amplitude-encoded signal.

Similarly to FIG. 2, in FIG. 3, the abscissa is indicated in terms of unit of bits and if a bit as a unit is regarded as the unit of time $\delta$, the unit of the abscissa may be read as the time.

This compressed pulse signal is an example in which the transmission signal amplitude of which have been encoded by the finite length sequence having a length of 64 bits, is used. This sequence having 64 bits has been provided by adding one bit to the finite length sequence of having 63 bits which was used for generating the transmission signals as shown in FIG. 2. Accordingly, the pulse duration of this transmission signal is $64 \times \delta$. The pulse duration of corresponding echo signals has also the nearly same length.

However, as seen in FIG. 3, a majority of the energy of the compressed pulse signal is concentrated on the central part of the abscissa (time) (a few bit $\times \delta$) in the drawing. The portion of the signal located on the central part of the abscissa which have been a considerable amplitude is called as the main lobe of the compressed pulse. The pulse duration of the main lobe is short. This means that the energy of the echo signal which has been substantially uniformly distributed over a long period of time similarly to the pulse duration of the transmission signal has been compressed substantially at one point along the time base. The signal portions having smaller amplitudes at the both sides of the main lobe are called as range side lobes of the compressed pulse.

It is to be noted that the transmission signal as shown in FIG. 2 is generated from the signal source 1 through the digital delay line 2, bipolar converter 3 and the transmitter 4, and the ultrasonic probe 6 is driven by the transmission signal to emit an ultrasonic wave.

The ultrasonic wave emitted into the water in the vessel by the ultrasonic probe 6 will be reflected by the target S and returned again to the ultrasonic probe 6. The echo signal received by the ultrasonic probe 6 will be sent to the multiplier 7a of the analog correlator 7.

The pulse width of the echo signal has nearly the same length as that of the transmission signal. More specifically, the energy of the echo signal has been substantially uniformly distributed over a long duration of time nearly corresponding to the pulse width of the transmission signal (i.e., nearly 63×δ in the case of FIG. 2, and nearly 64×δ in the case of FIG. 3).

The same signal as the transmission signal as described above is sent to the multiplier 7a of the analog correlator 7 via the digital delay line 2 and the bipolar converter 5. The analog correlator 7 is adapted to execute a correlation operation between the echo signal and the transmission signal. This correlation operation will cause the energy of the echo signal, which is substantially uniformly distributed along the time base for a long time duration equivalent to that of the transmission signal, to be compressed substantially at one point along the time base. It is to be noted that the pulse signal obtained through such correlation operation is called the compressed pulse.

The compressed pulse provided by the analog correlator 7 is sent to the display 8 where it is displayed as the final result.

The distance resolution of the conventional inspection apparatus explained above depends on the duration of the main lobe of the compressed pulse (which is referred briefly to as the pulse duration of the compressed pulse). The pulse duration of the compressed pulse is short as described above despite the pulse duration of the transmission signal being long. Accordingly, an equivalent resolution to that of the prior inspection apparatus based on a pulse echo method using a transmission signal with a short pulse duration will be obtained.

On the other hand, the S/N ratio (signal vs noise ratio) becomes higher, as the average transmission energy of the transmission signal becomes larger, and the average transmission energy is larger, as the pulse duration of the transmission signal is larger. Accordingly, according to the conventional inspection apparatus, a higher S/N ratio may be obtained as compared to the pulse echo method using a transmission signal with a short pulse duration.

As explained above, the prior inspection apparatus utilizing the finite length sequence is excellent in resolution and can attain a high S/N ratio.

It is here to be understood that the result of the correlation operation between the echo signal and the transmission signal is represented by a new function with $\tau$ as a variable, expressed as the following equation:

$$\int_{-\infty}^{\infty} s(t - \tau)r(t)dt \quad (1)$$

where r(t) and s(t) respectively represent the echo signal and the transmission signal. This new function is called as correlation function and represents the compressed pulse described above. It is needless to say that the above integration range ($-\infty - \infty$) can be limited to a finite range of time, if either of the echo signal r(t) or the transmission signal s(t) assumes to take value(s) other than zero in the finite time range and to take zero out of the finite time range.

As explained above, according to the conventional inspection apparatus, the correlation operation between the echo signal and the transmission signal is executed by use of the analog correlator 7. However, since the analog correlator 7 consists only of the multiplier 7a and the integrator 7b, operation of varying the variable $\tau$ in the equation (1) has to be externally executed. In other words, the operation of delaying the transmission signal s(t) by $\tau$ will be executed by the digital delay line 2 and the system control unit 9 and s(t−$\tau$) is input to the multiplier 7a. This means the following.

Since operation of varying the variable $\tau$ in the relation of equation (1) will not be executed only in the analog correlator 7, this means that the analog correlator 7 is not a correlator in the strict sense of the correlation operation. Furthermore, a single transmission will not provide a wave form of a compressed pulse (correlation function). In other words, what is obtained by a single transmission is only the value of a compressed pulse with regard to a fixed certain value of the variable $\tau$. In order to obtain the whole waveform of a compressed pulse, signal transmission must be repeated a number of times by changing the value of the variable $\tau$ for each transmission. Accordingly, it takes a relative long time until the final result of the whole waveform of the compressed pulse is obtained.

Other correlators for executing strictly (exactly) the correlation operation as expressed by equation (1) will be explained by referring to FIG. 4.

FIG. 4 is a block diagram illustrating another correlator disclosed in Japanese Patent Application No. 1-45316 relating to the present invention.

In FIG. 4, a correlator 10 is constituted by the delay line 10a with output taps, a plurality of multipliers 10b respectively connected to the output taps of the delay line 10a and an adder 10c connected to these multipliers 10b.

The correlator 10 realizes the correlation operation by utilizing the fact that the equation (1) can be transformed as follows:

$$\int_{-\infty}^{\infty} s(t-\tau)r(t)dt = \int_{-\infty}^{\infty} r(t+\tau)s(t)dt \quad (2)$$
$$= \int_{0}^{T} r(t+\tau)s(t)dt$$
$$\approx \sum_{k=1}^{K} r(k\Delta t + l\Delta t)s(k\Delta t)$$

provided that the transmission signal s(t) is assumed to take zero out of the time range from 0 to T, k and l are integers, $\Delta t$ is a sampling interval, K is a constant, t=k$\Delta t$, $\tau$=l$\Delta t$ and T=k$\Delta t$.

According to the correlator 10, $\Delta t$ designates a unit time delay of the delay line 10a between neighboring taps and K designates the aggregate number of taps. When the echo signal r(t) is input to the delay line 10a, an output from the k-th tap (k=1, 2, ..., K) will be multiplied by the multiplier 10b with a weight value s(k$\Delta t$) which has been prepared in advance. Subsequently, the adder 10c is caused to add outputs from all the multipliers 10b, whereby the result of the addition is equivalent to equation (2).

According to this correlator 10, operation of changing the variable $\tau$ corresponds to inputting the echo signal r(t) to the delay line 10a in the sequential timing. The echo signal r(t) is naturally input from the ultrasonic probe 6 in the sequential timing. Accordingly, the operation of changing the variable $\tau$ is automatically executed. Namely, according to the correlator 10 shown in FIG. 4, the time waveform of the compressed pulse can be obtained by only one transmission and in real time.

However, when the duration of the transmission signal, namely T becomes larger, the delay line 10a having a greater many number of taps will be required, and hence a greater many number of multipliers 10b will also be required. Further, also the adder 10c having a greater many number of input terminals will be required when a greater many number of the multipliers 10b is required. As the number of multipliers 10b and the number of input terminals of the adder 10c increase, the operation speed of the correlator 10 decreases. Moreover, the cost of such a correlator will be more expensive.

Furthermore, as seen in FIG. 3, the conventional apparatus has such a drawback as the level of the side lobes of the compressed pulse being relatively high.

Accordingly, the prior inspection apparatus as explained above takes a great deal of time to obtain the compressed pulse as a final result, while the operation speed has to be made slower if an attempt is to be made to realize real-time inspection by shortening the time required for obtaining the compressed pulse and the cost of the apparatus becomes expensive.

There is also a problem that the level of the side lobes of the compressed pulse is high.

SUMMARY OF THE INVENTION

The present invention has been provided to solve the problems as explained above. Accordingly, an object of the present invention is to provide an inspection apparatus which is inexpensive and capable of increasing the operation speed. Further object of the present invention is to provide an inspection apparatus which is capable of obtaining a compressed pulse having side lobes with a low level, preferably zero, in addition to being inexpensive and capable of attaining a high operational speed.

To attain these objects, an inspection apparatus according to the present invention is provided with the following means:

(1) transmission signal generation means adapted to generate first and second basic unit signals ga(t) and gb(t) in accordance with first and second sequences {a} and {b}, generate a first transmission signal Sap(t) based on the first basic unit signal ga(t) and a third sequence {p}, generate a second transmission signal Saq(t) based on the first basic unit signal ga(t) and a fourth sequence {q}, generate a third transmission signal Sbp(t) based on the second basic unit signal gb(t) and the third sequence {p}, and generate a fourth transmission signal Sbq(b) based on the second basic unit signal gb(t) and the fourth sequence {q};

(2) transmission means adapted to transmit waves driven by the first, second, third and fourth transmission signals to a target;

(3) reception means adapted to receive first, second, third and fourth echoes reflected from the target to provide echo signals Rap(t), Raq(t), Rbp(t) and Rbq(t) corresponding to the first, second, third and fourth transmission signals;

(4) first correlation means adapted to process by correlation the first and second echo signals Rap(t) and Raq(t) by using a first reference signal Ua(t) generated based on the first sequence {a} and process by correlation the third and fourth echo signals Rbq(t) and Rbq(t) by using a second reference signal Ub(t) generated based on the second sequence {b};

(5) second correlation means adapted to process by correlation the output of the first correlation means corresponding to the first and third echo signals Rap(t) and Rbp(t) by using a third reference signal Up(t) generated based on the third sequence {p} and process by correlation the output of the first correlation means corresponding to the second and fourth echo signals Raq(t) and Rbq(t) by using a fourth reference signal Uq(t) generated based on the fourth sequence {q}; and (6) adder means adapted to sum up the respective outputs from the second correlation means.

BRIEF DESCRIPTION OF THE DRAWINGS

FIGS. 32 and 33 are waveform diagrams illustrating first and second basic unit signals of the third embodiment;

FIGS. 35-38 are waveform diagrams illustrating first through fourth transmission signals of the third embodiment;

FIGS. 39-41 are block diagram illustrating fourth through sixth embodiments of the present invention;

DETAILED DESCRIPTION OF THE PREFERRED EMBODIMENTS

Figure 5:
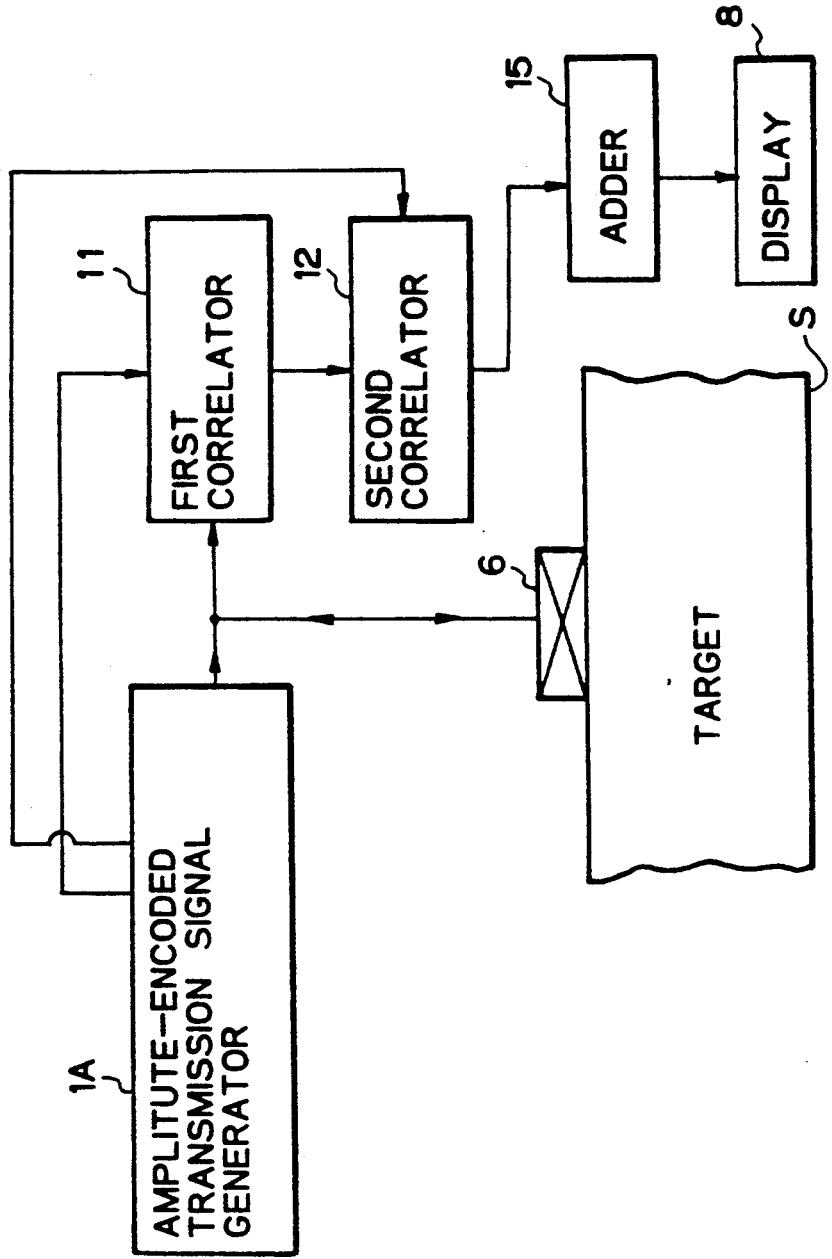
FIG. 5 is a block diagram illustrating a first embodiment of the present invention.

The constitution of a first embodiment of the present invention will firstly be explained by referring to FIG. 5.

Figure 1:
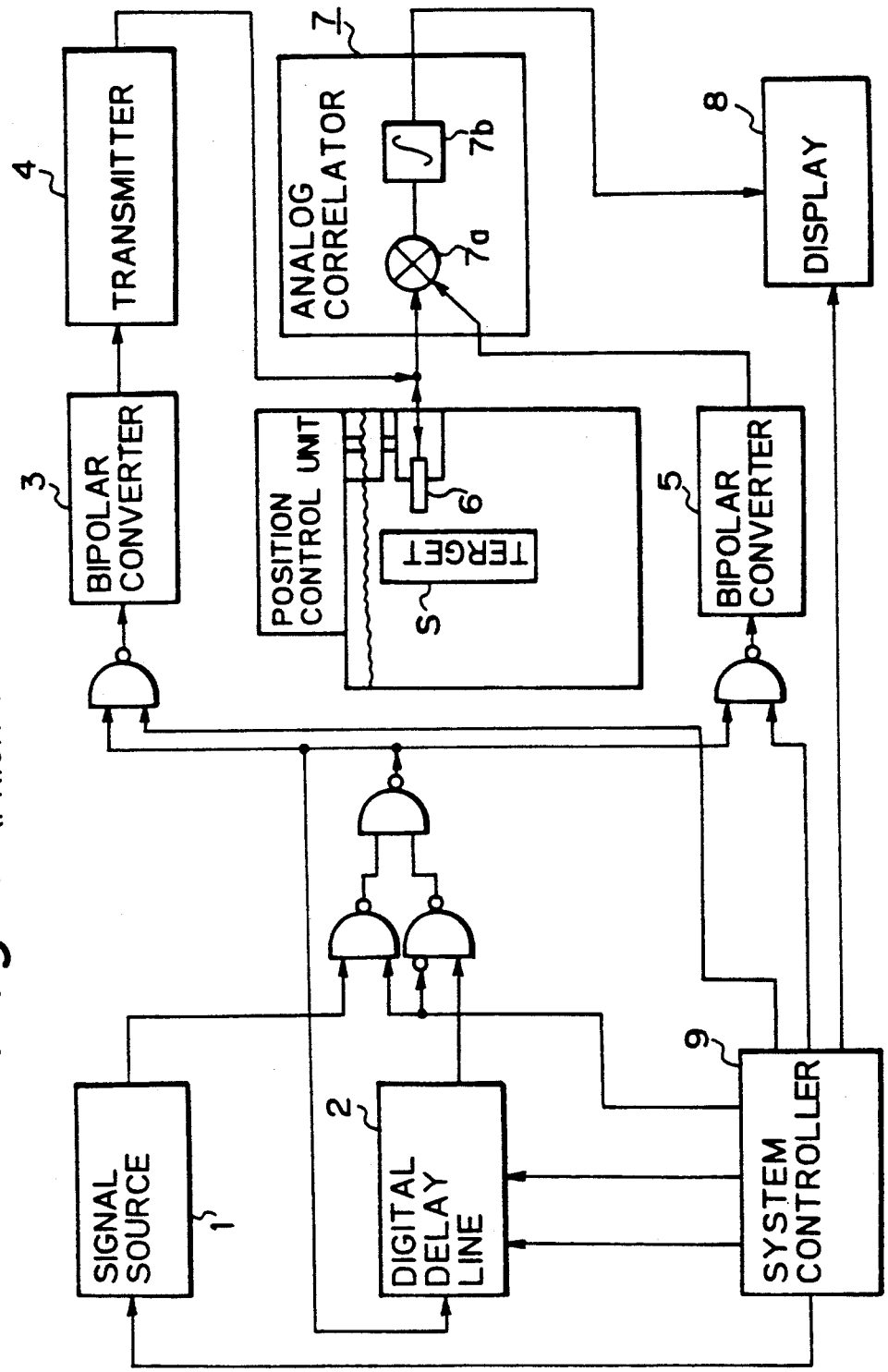
FIG. 1 is a block diagram illustrating an inspection apparatus according to a prior art.

As seen in FIG. 5, the first embodiment of the present invention is constituted with an ultrasonic probe 6 and a display 8 which are identical to those of the conventional apparatus as shown in FIG. 1, an amplitude-encoded transmission signal generator 1A, a first correlator 11 connected to the generator 1A and the ultrasonic probe 6, a second correlator 12 connected to the first correlator and the generator 1A and an adder 15 having memory function, an input of which is connected to the second correlator 12 and an output of which is connected to the display 8. It is to be noted that the ultrasonic probe 6 is connected not only to the first correlator but also to the generator 1A and is contacted to a target S to be inspected.

Operation of the first embodiment will be explained by referring to FIGS. 6 through 11.

Figure 6:
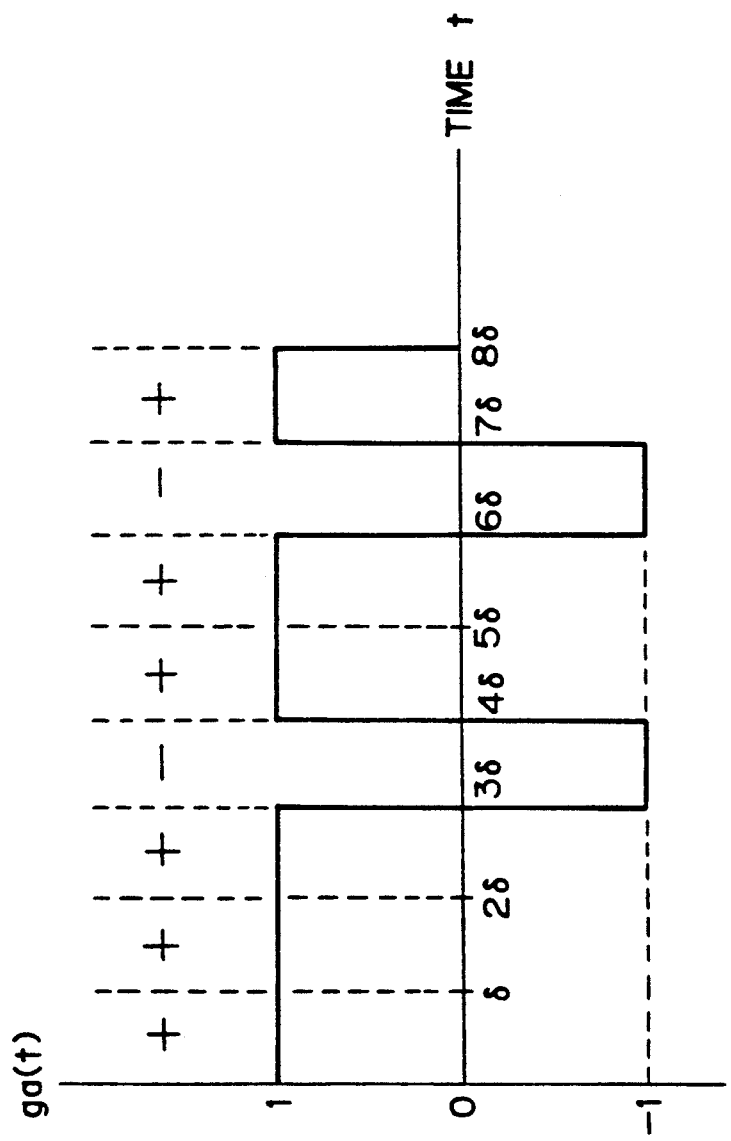
FIGS. 6 and 7 are waveform diagrams illustrating first and second basic unit signals of the first embodiment.
Figure 7:
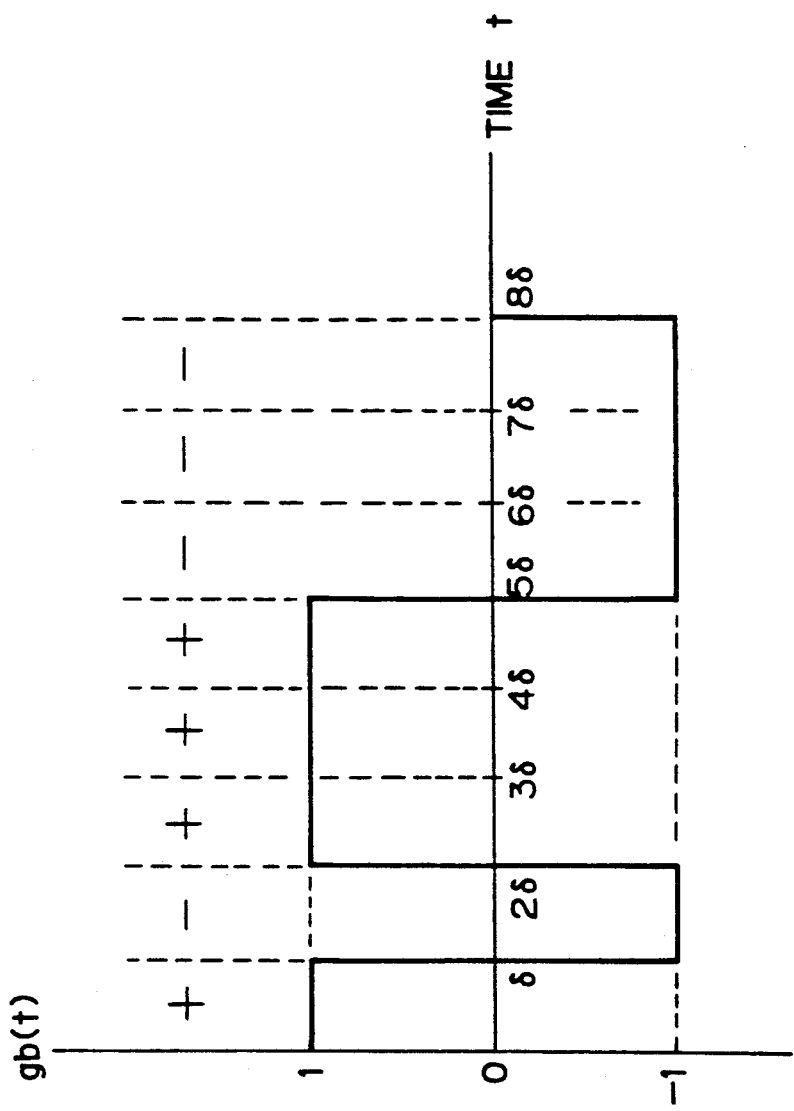

FIGS. 6 and 7 are waveform diagrams respectively showing first and second basic unit signals ga(t) and gb(t) in the first embodiment. FIGS. 8 through 11 are waveform diagrams respectively showing first through fourth transmission signals Sap(t), Saq(t), Sbp(t) and Sbq(t).

The generator 1A is adapted to internally generate first through fourth sequences {a}, {b}, {p} and {q}, and to generate the first and second basic unit signals ga(t) and gb(t) as shown in FIGS. 6 and 7, which is defined respectively by the first and second sequences {a} and {b}.

The generator 1A outwardly generates first through fourth transmission signals. The first transmission signal is provided based on the third sequence {b} and the first basic unit signal ga(t), the second transmission signal is provided based on the fourth sequence {q} and the first basic unit signal ga(t), the third transmission signal is provided based on the third sequence {p} and the second basic unit signal gb(t), and the fourth transmission signal is provided based on the fourth sequence {q} and the second basic unit signal gb(t).

These first through fourth transmission signals are generated repeatedly with a constant transmission repetition period Tr and then sequentially sent to the ultrasonic probe 6.

The first sequence {a} has a length (M) of 8, and is represented as follows:

$$\{a\} = \{a_1, a_2, a_3, a_4, a_5, a_6, a_7, a_8\}$$
$$= \{+, +, +, -, +, +, -, +\}$$

Figure 2:
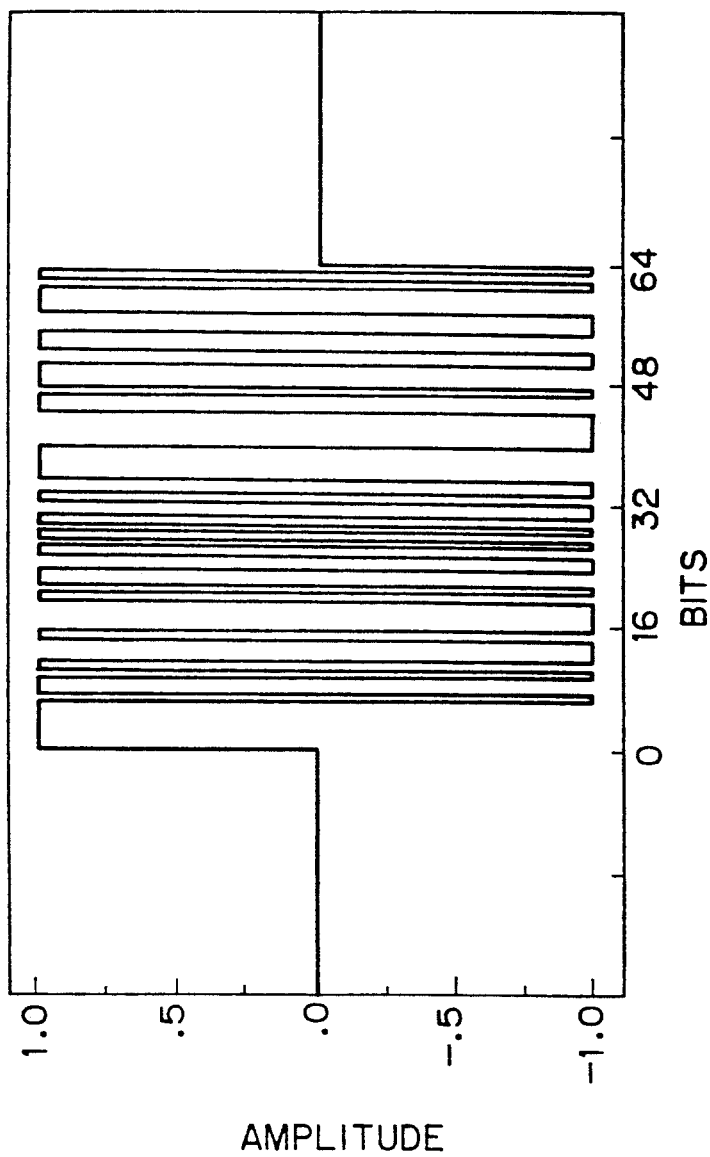
FIG. 2 is a waveform diagram illustrating a transmission signal from the prior inspection apparatus shown in FIG. 1.
Figure 3:
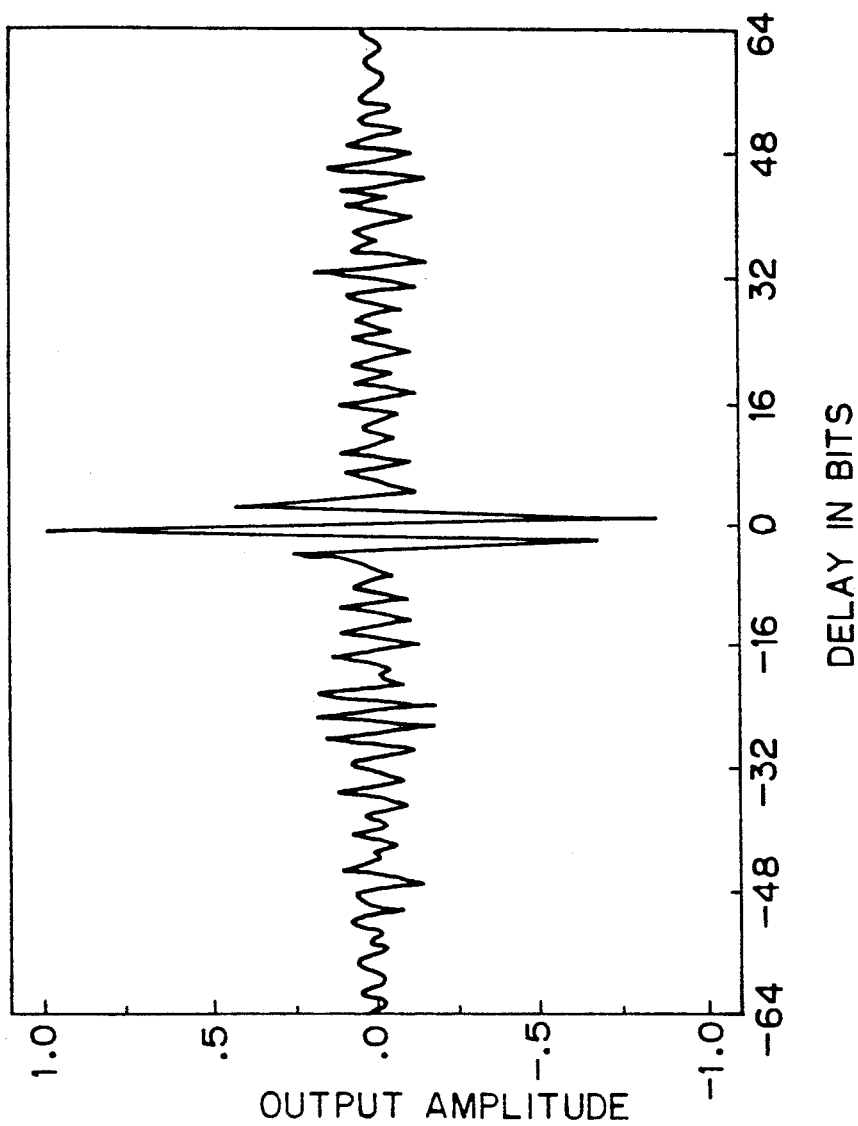
FIG. 3 is a waveform diagram illustrating a compressed pulse obtained by the prior inspection apparatus shown in FIG. 1.

As shown in FIG. 6, the first basic unit signal ga(t) is generated by encoding amplitudes with the sequence {a}, similarly to the prior art as shown in FIG. 2. In FIG. 6, in order to enable the relationship between the first sequence {a} and the amplitude-encoding operation to be better understood, the symbols (+) and (−) which are the contents of the components of the sequence {a} are also inserted. $\delta$ is a fixed time duration.

Similarly, the second basic unit signal gb(t) is generated by encoding amplitudes with the sequence {b} which has a length of 8 and is represented as follows:

$$\{b\} = \{b_1, b_2, b_3, b_4, b_5, b_6, b_7, b_8\}$$
$$= \{+, -, +, +, +, -, -, -\}$$

Figure 8:
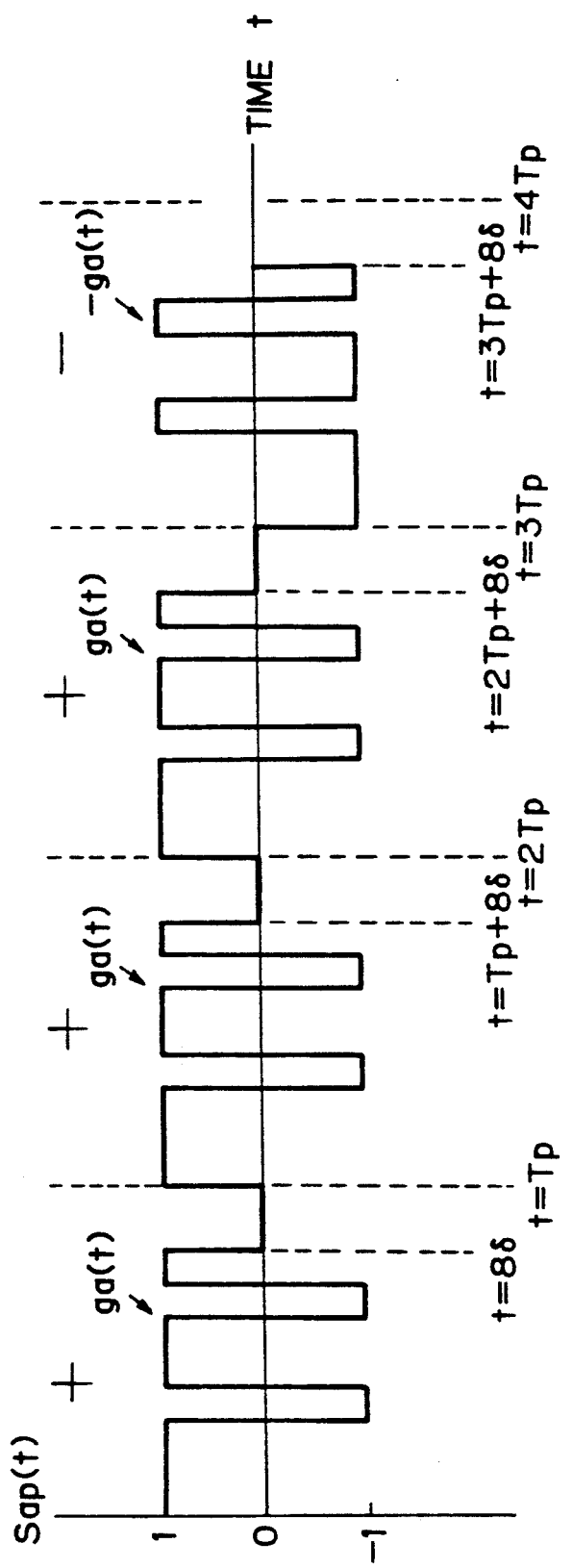
FIGS. 8-11 are waveform diagrams illustrating first through fourth transmission signals of the first embodiment.
Figure 9:
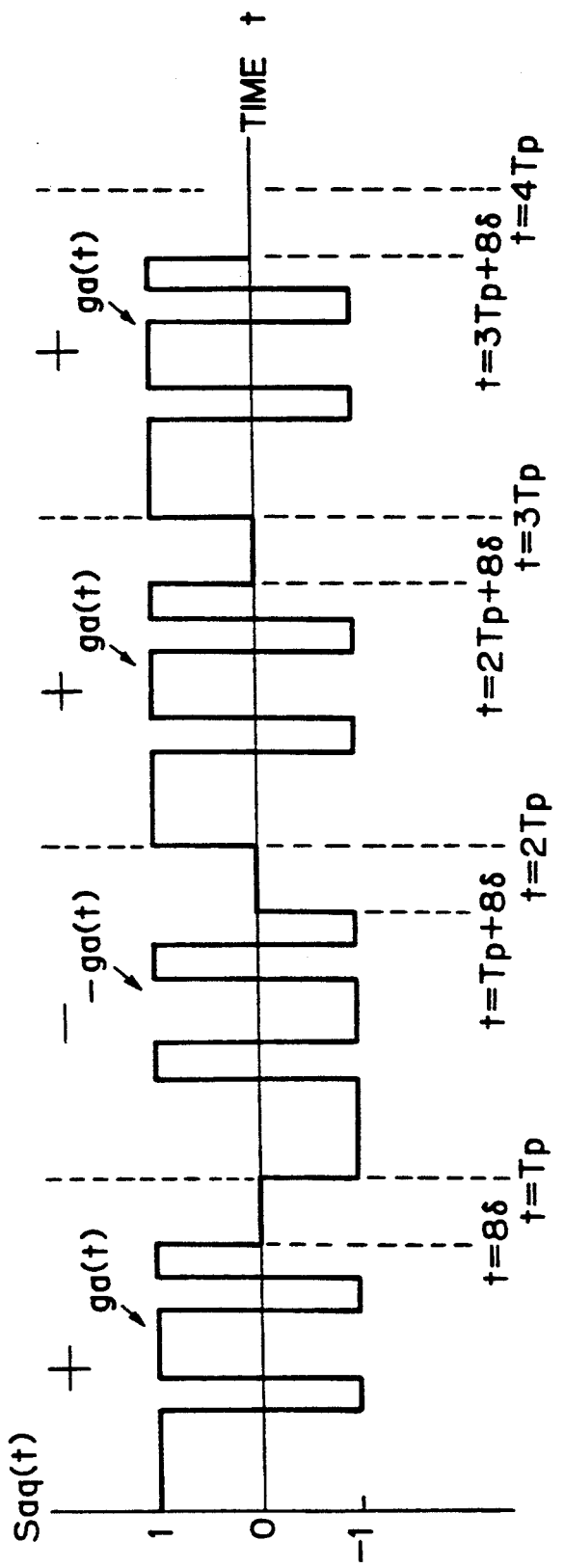

The first and second transmission signals Sap(t) and Saq(t) are respectively represented in FIGS. 8 and 9, together with the symbols (+) and (−) representing the contents of the components of the third and fourth sequences. These sequences {p} and {q} are expressed as follows:

$$\{p\} = \{p_1, p_2, p_3, p_4\}$$
$$= \{+, +, +, -\}$$
$$\{q\} = \{q_1, q_2, q_3, q_4\}$$
$$= \{+, -, +, +\}$$

The first transmission signal Sap(t) is generated in accordance with the following relationships:

When the component of the third sequence {p} is (+), the signal Sap(t) is allocated to the first basic unit signal ga(t), while the component is (−), the signal Sap (t) is allocated to the signal −ga(t) which is obtained by multiplying the signal ga(t) by −1. Accordingly, the first transmission signal Sap(t) are formed by arranging ga(t) and −ga(t) along the time base according to the order in which the symbols (+) and (−) in the third sequence {p} will appear.

In a similar manner, the second transmission signal Saq(t) is generated using the fourth sequence {q} and the first basic unit signal ga(t).

Figure 10:
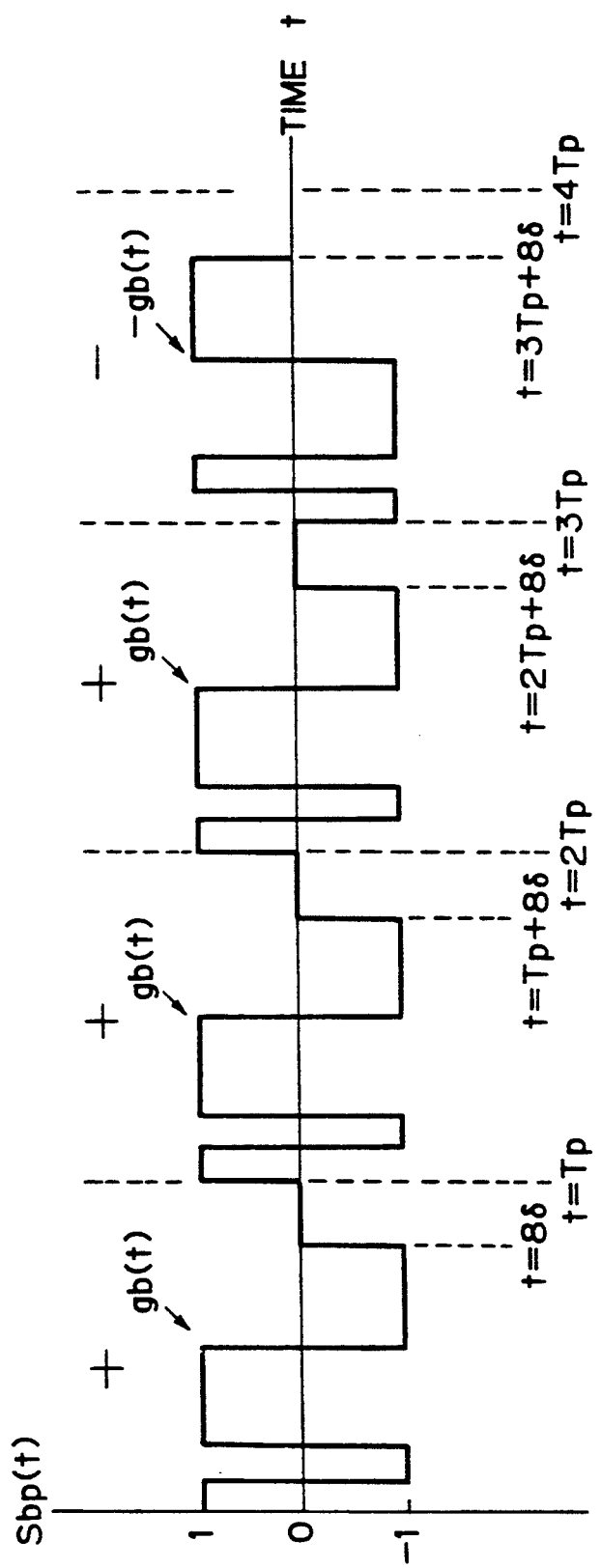
Figure 11:
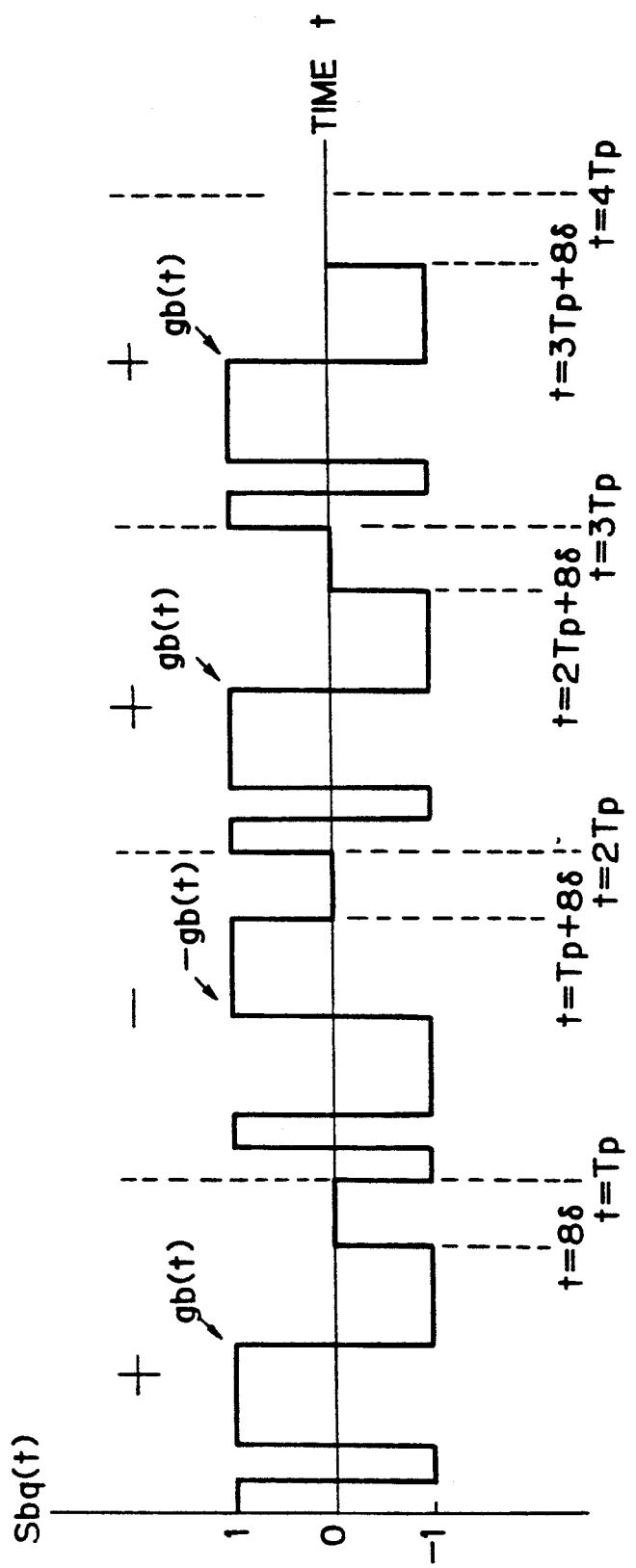

The third and fourth transmission signals Sbp(t) and Sbq(t) is respectively shown in FIGS. 10 and 11, together with the arrangements of the symbols (+) and (−) according to the third and fourth sequences {p} and {q}. These signals Sbp(t) and Sbq(t) are formed, in the similar manner to the first and second transmission signals Sap(t) and Saq(t), by arranging the signals gb(t) and −gb(t) along the time base according to the order of the symbols (+) and (−) in the third and fourth sequences {p} and {q}.

The ultrasonic probe 6 is driven by the first through fourth transmission signals to transmit ultrasonic waves into the target, or test piece S for inspection, and receives the echoes reflected from objects such as flaws in the test piece S. It is to be understood that received electrical echo signals corresponding respectively to the first through fourth transmission signals are to be referred to as first through fourth echo signals and designated respectively with Rap(t), Raq(t), Rbp(t) and Rbq(t).

The received first through fourth echo signals are sent to the first correlator 11.

On the other hand, a first reference signal Ua(t) which sill be used for correlation processing of the first and second echo signals Rap(t) and Raq(t) is generated by the generator 1A and sent to the first correlator 11. The first reference signal is a signal relevant to the first sequence {a}, for example the signal ga(t). A second reference signal Ub(t) which will be used for correlation processing of the third and fourth echo signals Rbp(t) and Rbq(t) is also generated by the generator 1A and sent to the first correlator 11. The second reference signal Ub(t) is the signal relevant to the second sequence {b}, for example gb(t).

The first correlator 11 executes a correlation operation between the first echo signal Rap(t) and the first reference signal Ua(t). The result of the correlation operation is expressed by Caap(t) and referred to as a first correlation operation result. The first correlator 11 also executes correlation operation between the second echo signal Raq(t) and the first reference signal Ua(t). The result of this correlation operation is expressed by Caaq(t) and referred to as a second correlation operation result. The first correlator 11 executes correlation operation between the third echo signal Rbp(t) and the second reference signal Ub(t) and also between the fourth echo signal Rbq(t) and the second reference signal Ub(t). The results of these correlation operation are expressed by Cbbp(t) and Cbbq(t) and referred to as third and fourth correlation operation results respectively.

These first through fourth correlation operation results of the first correlator 11 are then sent to the second correlator 12.

On the other hand, third and fourth reference signals Up(t) and Uq(t) which will be utilized in the correlation processing in the second correlator 12 are generated by the generator 1A and sent to the second correlator 12. The third and fourth reference signals are signals relevant to the third and fourth sequences {p} and {q} respectively.

In the second correlator 12, correlation operation will be conducted between the first correlation operation result Caap(t) and the third reference signal Up(t), between the second correlation operation result Caaq(t) and the fourth reference signal Uq(t), between the third correlation operation result Cbbp(t) and the third reference signal Up(t) and between the fourth correlation operation result Cbbq(t) and the fourth reference signal Uq(t). The results of these correlation operation in the second correlator 12 are respectively designated by Caapp(t), Caaqq(t), Cbbpp(t) and Cbbqq(t) and referred to respectively as the first through fourth compressed pulses.

These first through fourth compressed pulses are sent to the adder 15 and stored therein to sum up these compressed pulses as follows:

$$C = Caapp(t) + Caaqq(t) + Cbbpp(t) + Cbbqq(t)$$

The result of this summing operation is referred to as a composite compressed pulse.

This composite compressed pulse C is transmitted to the display 8 from the adder 15, and displayed in a similar manner to that of a prior art.

The operational principle of the first embodiment as mentioned above will next be explained by referring to FIGS. 12 through 25.

Figure 12:
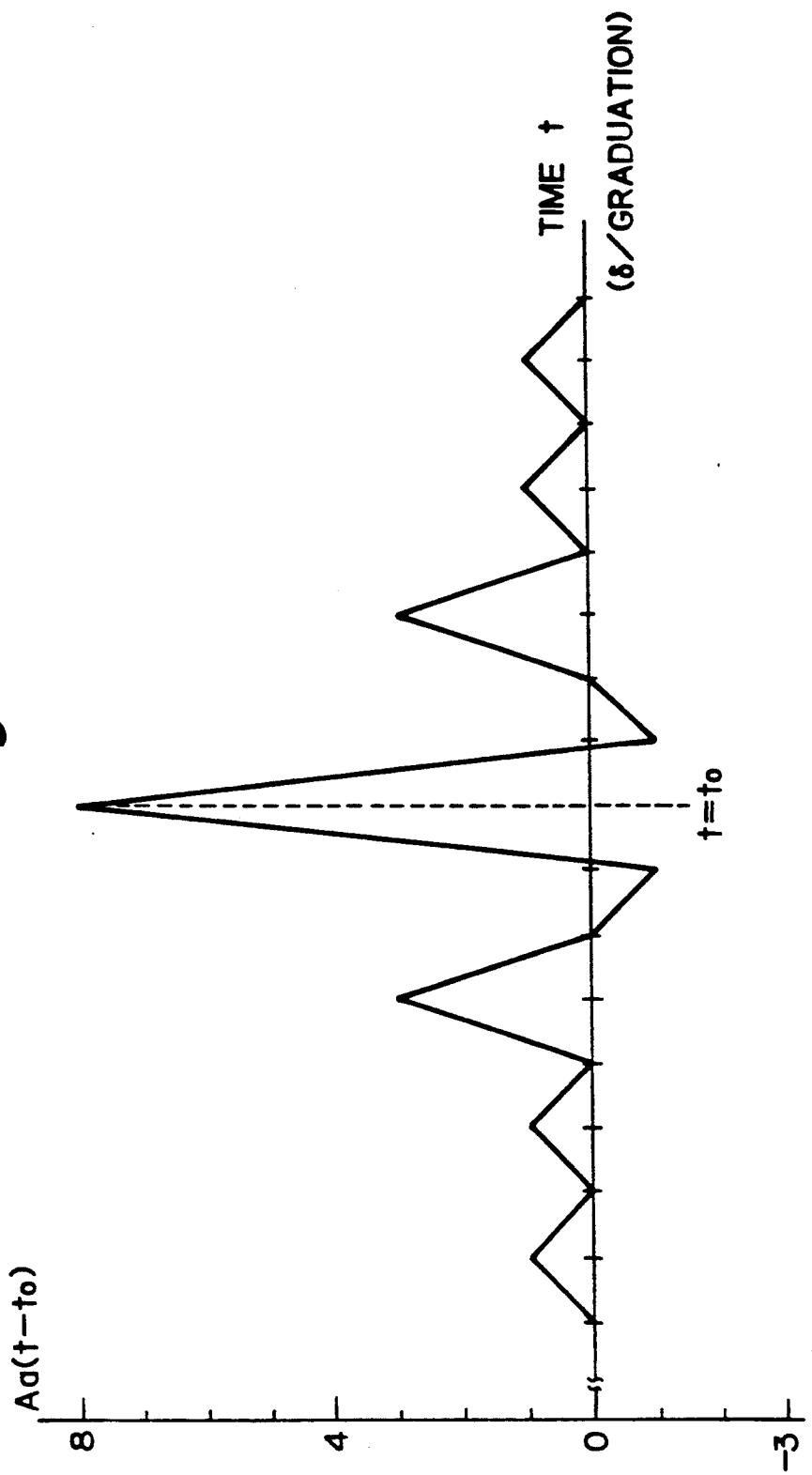
FIGS. 12 and 13 are waveform diagrams illustrating first and second basic unit compressed pulses of the first embodiment.
Figure 13:
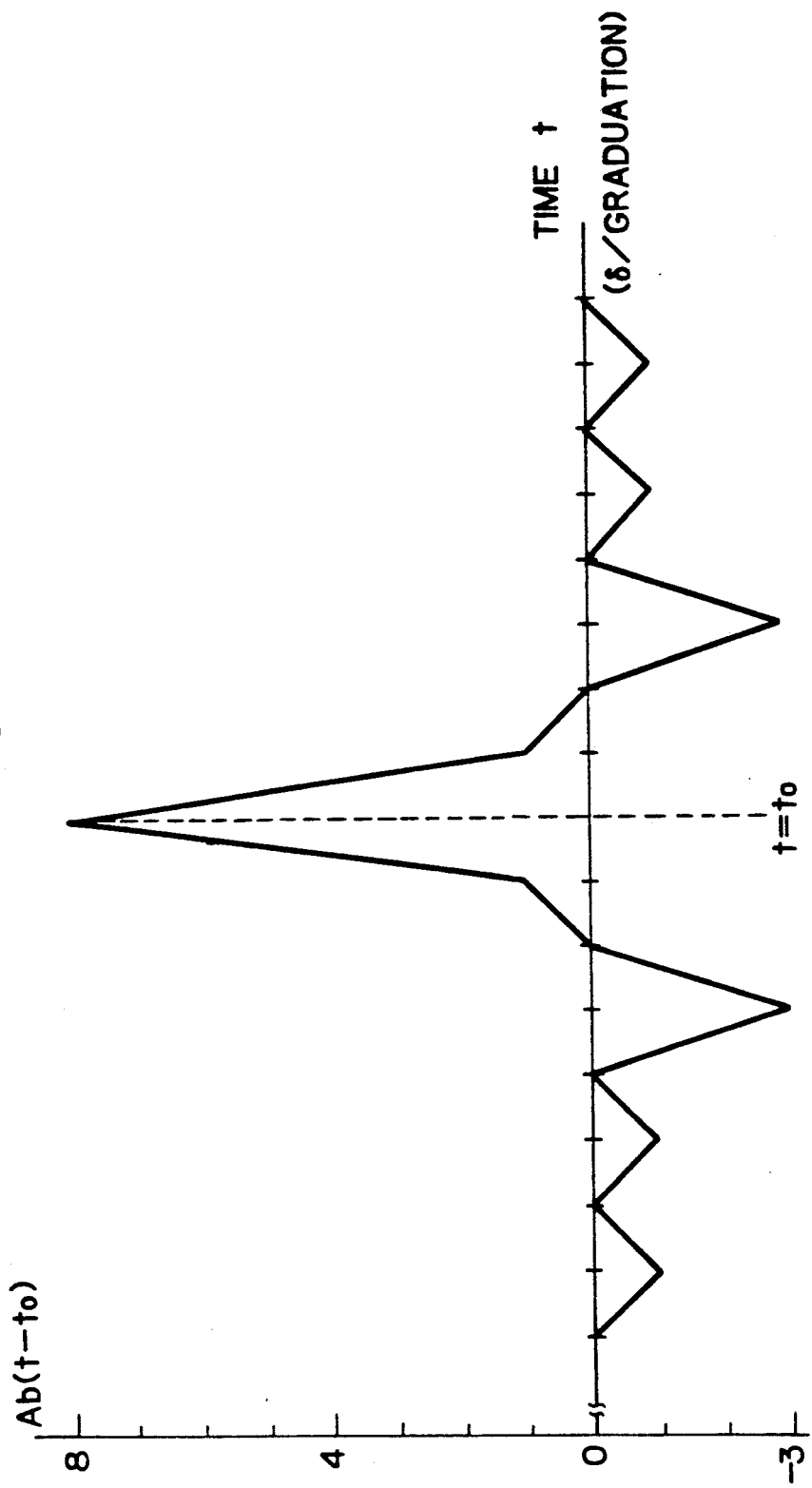
Figure 18:
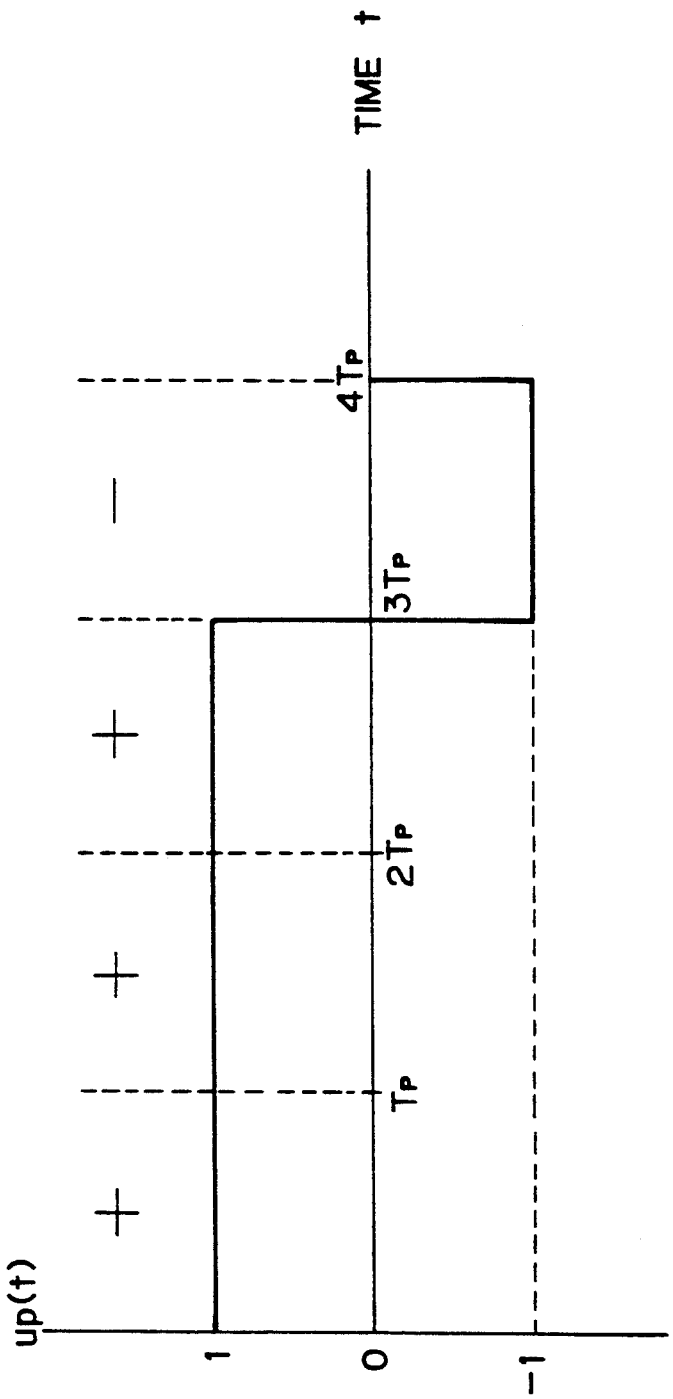
FIGS. 18 and 19 are waveform diagrams illustrating third and fourth reference signals of the first embodiment.
Figure 19:
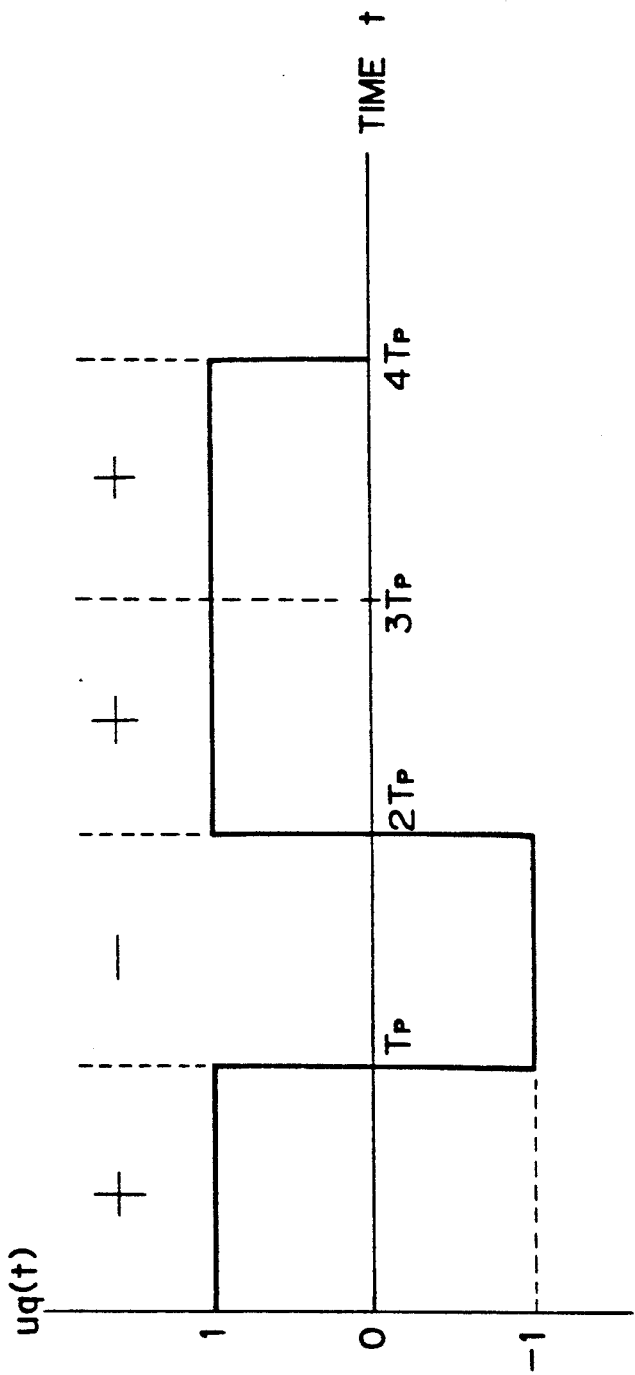
Figure 24:
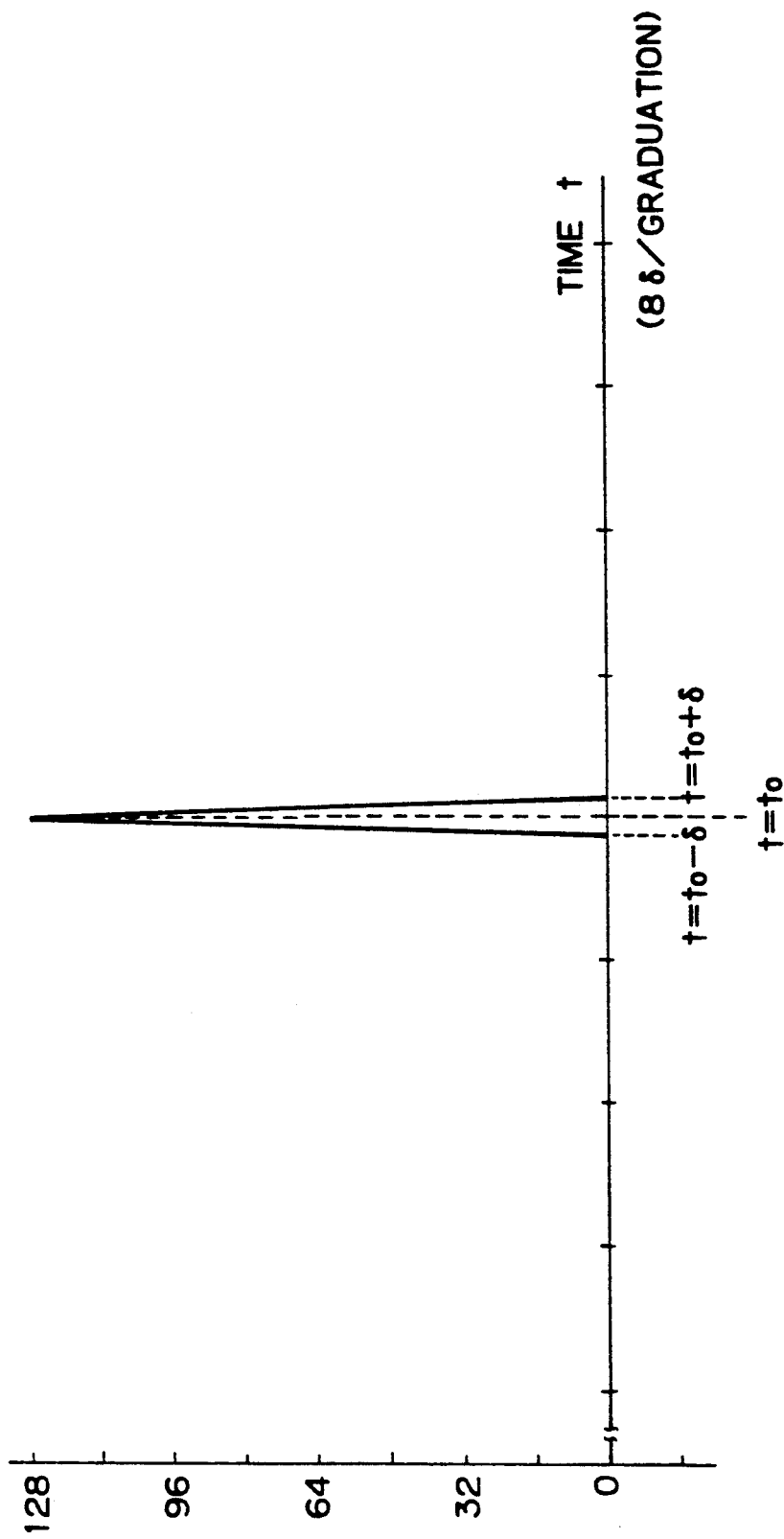
FIG. 24 is a waveform diagram illustrating composite compressed pulse of the first embodiment.
Figure 25:
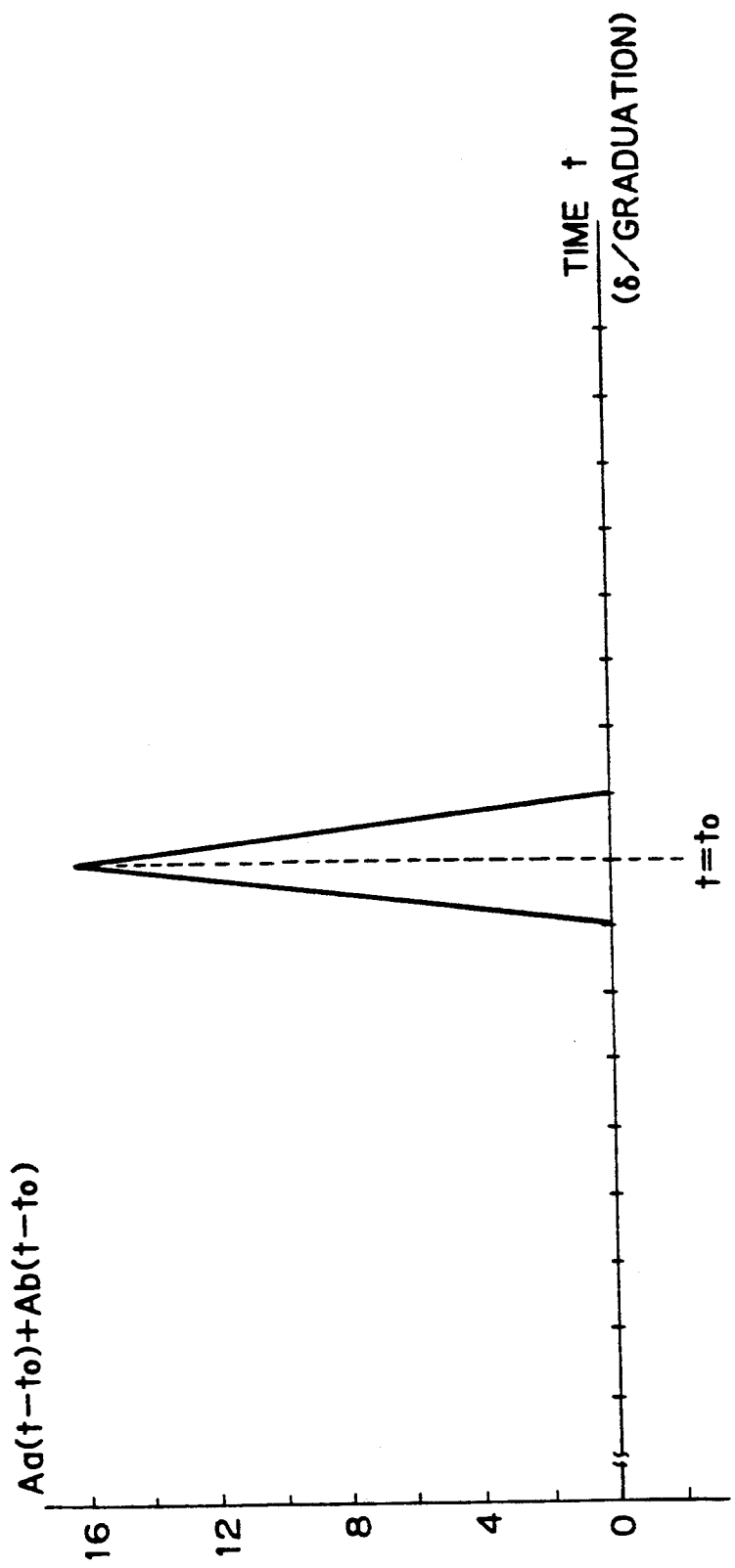
FIG. 25 is a waveform diagram illustrating a composite basic unit compressed pulse of the first embodiment.

FIGS. 12 and 13 show waveform diagrams illustrating first and second basic unit compressed pulses according to first embodiment of the present invention, FIGS. 14 through 17 waveform diagrams respectively illustrating the first through fourth correlation operation results Caap(t), Caaq(t), Cbbp(t) and Cbbq(t), and FIGS. 18 and 19 waveform diagrams respectively illustrating the third and fourth reference signals Up(t) and Uq(t), FIGS. 20 through 23 waveform diagrams respectively illustrating the first through fourth compressed pulses Caapp(t), Caaqq(t), Cbbpp(t) and Cbbqq(t). FIG. 24 is a waveform diagram illustrating the composite compressed pulse C, and FIG. 25 is a waveform diagram illustrating a composite basic unit compressed pulse $Aa(t-t_0) + Ab(t-t_0)$.

The first transmission signal Sap(t) shown in FIG. 8 is expressed by the following equation.

$$Sap(t) = \sum_{i=1}^{N} p_i ga[t - (i-1)Tp] \quad (3)$$
$$= p_1 ga(t) + p_2 ga(t - Tp) + p_3 ga(t - 2Tp) + p_4 ga(t - 3Tp)$$

where the symbols (+) and (−) of the component $p_i$ of the third sequence {p} are regarded as identical to +1 and −1 respectively and thus ga(t) is multiplied by $p_1$. (Same applies to the following transmission signals.)

The second transmission signal Saq(t) shown in FIG. 9 can be expressed by the equation which has replaced the component $p_i$ of the third sequence {p} by the component $q_i$ of the fourth sequence {q} at the right side of the equation (3). The third transmission signal Sbp(t) shown in FIG. 10 can be expressed by the equation which has replaced the first basic unit signal ga(t) by the second basic unit signal gb(t) at the right side of equation (3). Furthermore, the fourth transmission signal Sbq(t) shown in FIG. 11 can be expressed by the equation which has replaced the component $p_i$ of the third sequence {p} by the component $q_i$ of the fourth sequence {q} and the first basic unit signal ga(t) by the second basic unit signal gb(t) at the right side of the equation (3). It is to be noted that the time origin is rearranged to each generation time of the second through fourth transmission signals.

The first echo signal Rap(t) is expressed by the following equation:

$$Rap(t) = Co \times \int_{-\infty}^{\infty} Sap(t_1) h(t - t_0 - t_1) dt_1 \quad (4)$$

In the above, $t_0$ is a constant and h(t) signifies the inverted Fourier transform of the frequency of response characteristics in the signal propagation path from the output terminal of the generator 1A to the input terminal of the first correlator 11 by way of the ultrasonic probe 6, the reflective body of the test piece S and again the ultrasonic probe 6. That is, h(t) represents impulse response characteristics at the signal propagation path. $t_0$ is the time required for the ultrasonic wave to travel to and from the reflective body in the test piece S.

Even if Co=1 is applied, generality is not lost. Therefore, Co=1 is used in the following explanation.

The second through fourth echo signals Raq(t), Rbp(t) and Rbq(t) can be expressed by the equations which have replaced the first transmission signal Sap(t) by the second through fourth transmission signal Saq(t), Sbp(t) and Sbq(t) at the right side of equation (4), respectively.

The first correlation operation results Caap(t) is expressed as follows:

$$Caap(t) = \int_{-\infty}^{\infty} Ua(t_2 - t)Rap(t_2)dt_2 \tag{5}$$

If the following equation 6 is applied, $$Aa(t) = \int_{-\infty}^{\infty} \int_{-\infty}^{\infty} Ua(t_2 - t)ga(t_1)h(t_2 - t_1)dt_1dt_2, \tag{6}$$

the result Caap(t) can be expressed by the following equation, in accordance with equations (3) through (6):

$$\begin{aligned} Caap(t) &= \sum_{i=1}^{N} p_i Aa[t - t_0 - (i-1)Tp] \\ &= p_1 Aa(t - t_2) + p_2 Aa(t - t_0 - Tp) + \\ &\quad p_3 Aa(t - t_0 - 2Tp) + p_4 Aa(t - t_0 - 3Tp) \end{aligned} \tag{7}$$

In equation (7), $Aa(t-t_0)$ corresponds to a compressed pulse which is obtained by causing the ultrasonic probe 6 to be driven by the first basic unit signal ga(t) to obtain an echo signal and correlation processing this echo signal using the first reference signal Ua(t) as the reference signal. This compressed pulse is referred to as a first basic unit compressed pulse and shown in FIG. 12.

It is seen from equation (7) that Caap(t) is equal to what is obtained by displacing four of the first basic unit compressed pulses $Aa(t-t_0)$ in respect of time along the time base by 0, Tp, 2Tp and 3Tp, multiplying the displaced pulses with the components $p_1$, $p_2$, $p_3$, $p_4$ of the third sequence {p} and adding them together.

The second correlation operation result Caaq(t) can be expressed by the equation which has replaced the first echo signal Rap(t) by the second echo signal Raq(t) at the right side of equation (5). This is also equivalent to the equation which has replaced $p_i$ by $q_i$ (i=1, 2, 3, 4) at the right side of equation (7).

Similarly, the third correlation operation result Cbbp(t) can be expressed by the equation which has replaced the first echo signal Rap(t) by the third echo signal Rbp(t) and also replaced the first reference signal Ua(t) by the second reference signal Ub(t) at the right side of equation (5). This Cbbp(t) is also equivalent to the equation which has replaced Aa(t) by Ab(t) at the right side of equation (7) if the following equation (8) is applied.

$$Ab(t) = \int_{-\infty}^{\infty} \int_{-\infty}^{\infty} Ub(t_2 - t)gb(t_1)h(t_2 - t_1)dt_1dt_2 \tag{8}$$

It is to be noted that $Ab(t-t_0)$ corresponds to a compressed pulse which is obtained by causing the ultrasonic probe 6 to be driven by the second basic unit signal gb(t) and correlation processing an echo signal by utilizing the second reference signal Ub(t). This compressed pulse $Ab(t-t_0)$ is referred to as a second basic unit compressed pulse and shown in FIG. 13.

The fourth correlation operation result Cbbq(t) can be expressed by the equation which has replaced the first reference signal Rap(t) by the fourth echo Rbq(t) and also replaced the first reference signal Ua(t) by the second reference signal Ub(t) at the right side of equation (5). The result Cbbq(t) is equivalent to the equation which has replaced Aa(t) by Ab(t) and also replace $p_i$ and $q_i$ (i=1, 2, 3, 4) at the right side of equation (7).

The first compressed pulse Caapp(t) can be expressed by the following equation:

$$Caapp(t) = \int_{-\infty}^{\infty} Up(t_3 - t)Caap(t_3)dt_3 \tag{9}$$

The second compressed pulse Caaqq(t) can be expressed by the equation which has replaced the first correlation operation result Caap(t) by the second correlation operation result Caaq(t) and replaced the third reference signal Up(t) by the fourth reference signal Uq(t) at the right side of equation (9). The third compressed pulse Cbbpp(t) can be expressed by the equation which has replaced the first correlation operation result Caap(t) by the third correlation operation result Cbbp(t) at the right side of equation (9). The fourth compressed pulse Cbbqq(t) can be expressed by the equation which has replaced the first correlation operation result Caap(t) by the fourth correlation operation result Cbbq(t) and also replaced the third reference signal Up(t) by the fourth reference signal Uq(t) at the right side of equation (9). Accordingly, the second, third and fourth compressed pulses Caaqq(t), Cbbpp(t) and Cbbqq(t) are expressed as follows:

$$Caaqq(t) = \int_{-\infty}^{\infty} Uq(t_3 - t)Caaq(t_3)dt_3$$

$$Cbbpp(t) = \int_{-\infty}^{\infty} Up(t_3 - t)Cbbp(t_3)dt_3$$

$$Cbbqq(t) = \int_{-\infty}^{\infty} Uq(t_3 - t)Cbbq(t_3)dt_3$$

The first basic unit compressed pulse $Aa(t-t_0)$ shown in FIG. 12 has been provided as the result of computing equation (6) by utilizing the signal shown in FIG. 6 as the first basic unit signal ga(t) and this first basic unit signal ga(t) as the first reference signal Ua(t) with h(t) being a delta ($\delta$) function.

The second basic unit compressed pulse $Ab(t-t_0)$ shown in FIG. 13 has been provided as the result of computing equation (8) by using the signal shown in FIG. 7 as the second basic unit signal gb(t) and this second basic unit signal gb(t) as the second reference signal Ub(t) with h(t) being a delta ($\delta$) function.

Figure 14:
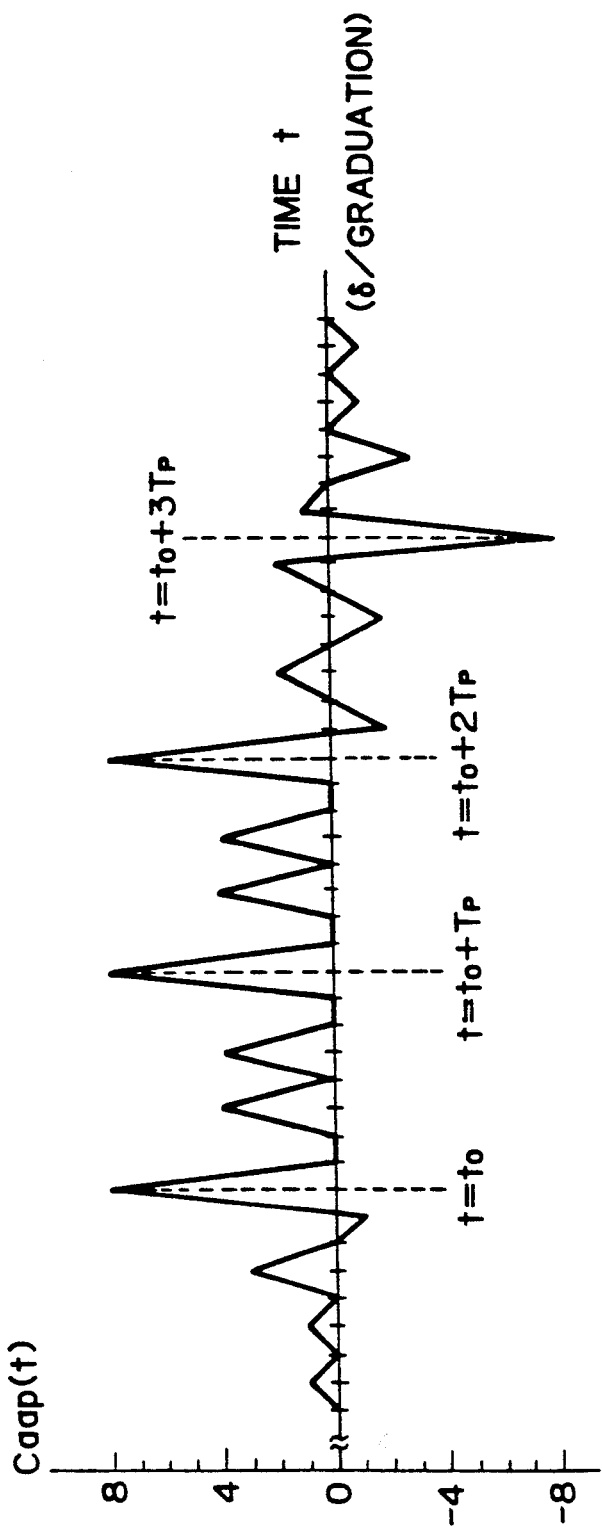
FIGS. 14-17 are waveform diagrams illustrating correlation operation results executed by a first correlator in the first embodiment.

The first correlation operation result Caap(t) by the first correlator 11 shown in FIG. 14 has been provided as the result of computing equation 7 with the first basic unit compressed pulse $Aa(t-t_0)$ shown in FIG. 12. The second correlation operation result Caaq(t) by the first correlator 11 shown in FIG. 15 has been provided as the result of the similar computing by using the first basic unit compressed pulse $Aa(t-t_0)$ shown in FIG. 12. The third and fourth correlation operation results Cbbp(t) and Cbbq(t) shown in FIGS. 16 and 17 have been provided as the results of the similar computing by using the second basic unit compressed pulse $Ab(t-t_0)$ shown in FIG. 13. In these computations, Tp has been set to be $8\delta$.

It is seen from FIGS. 14 through 17 that the first through fourth correlation operation results exhibit the energy being dispersed along the time base. This dispersion of the energy along the time base remains unchanged even if Tp is changed from 8δ to another time interval.

It can be noted, however, that the first through fourth correlation operation results can be compressed respectively through correlation processing by the second correlator 2.

In this respect, the signals shown in FIGS. 18 and 19 which have been generated using the third and fourth sequences {p} and {q} as the third and fourth reference signals respectively will now be explained.

The signal Up(t) shown in FIG. 18 has a waveform an amplitude of which has been encoded by using the third sequence {p}={+, +, +, −}. For better understanding of the relationship between this signal and the symbols (+) and (−) of the third sequence {p}, these symbols are also correspondingly indicated in FIG. 18.

Figure 15:
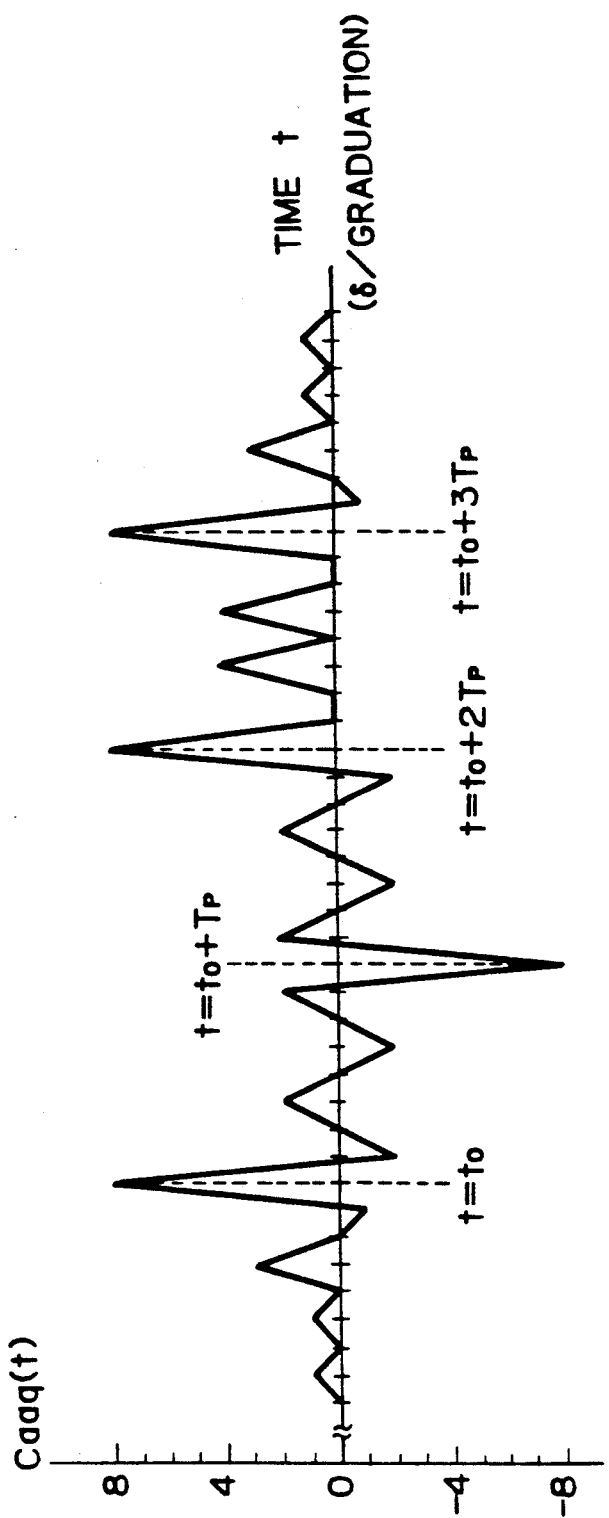
Figure 16:
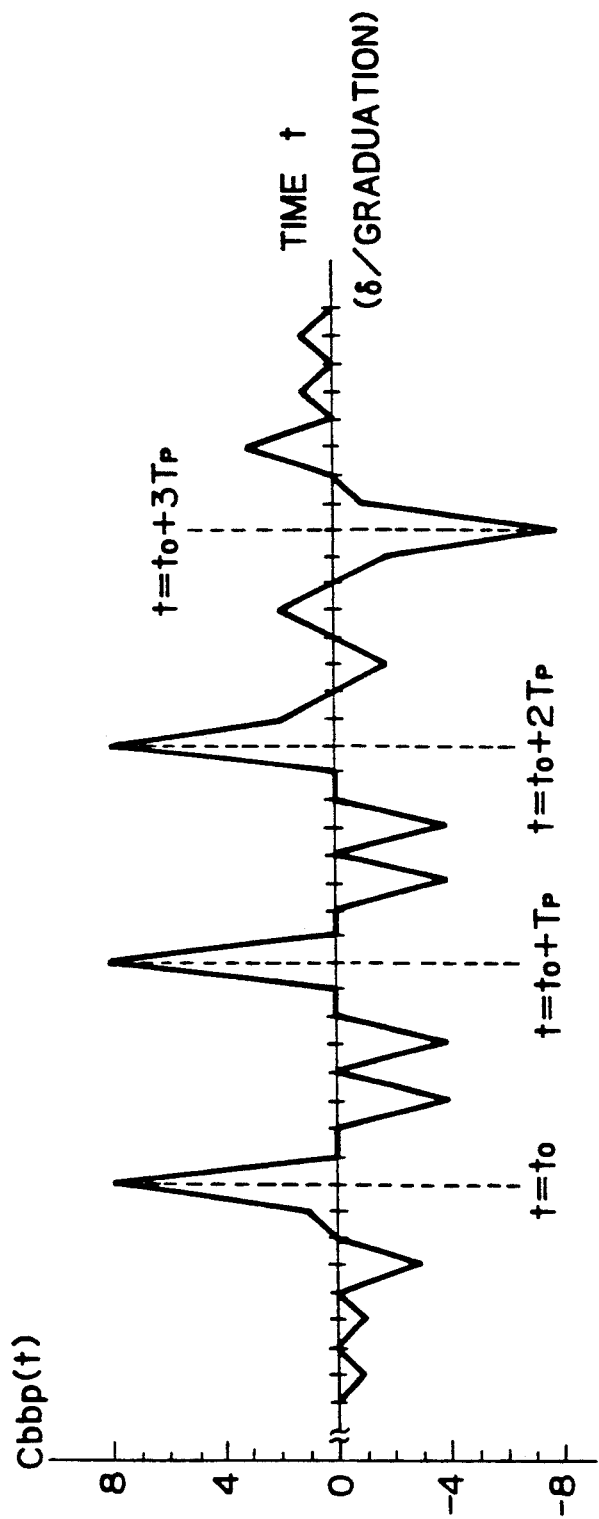
Figure 17:
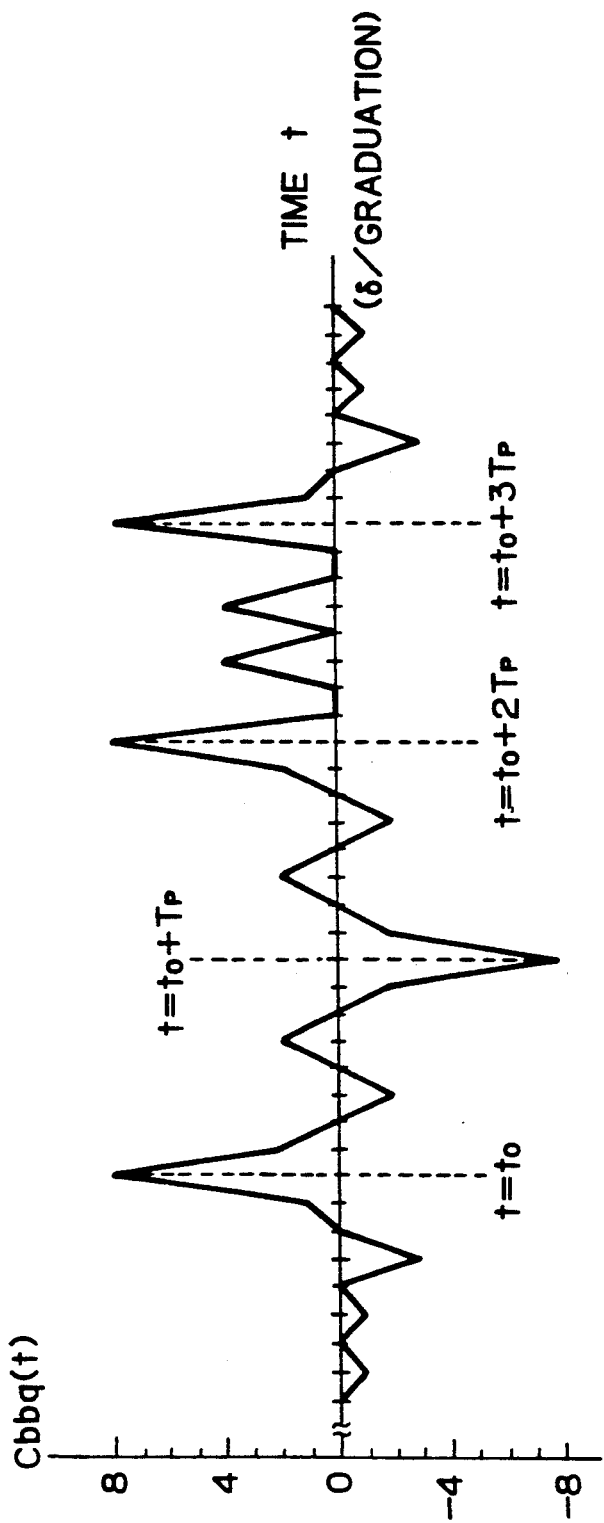

The signal shown in FIG. 19 has a waveform an amplitude of which has been encoded by using the fourth sequence {q}={+, −, +, +}, and similarly to above the symbols (+) and (−) are also indicated in FIG. 15.

In case that the third reference signal Up(t) shown in FIG. 18 is used, the first compressed pulse Caapp(t) will be as follows in accordance with equation (9):

$$Caap(t) = \sum_{i=1}^{N} p_i Caap[t + (i - 1)Tp] \quad (10)$$
$$= p_1 Caap(t) + p_2 Caap(t + Tp) + p_3 Caap(t + 2Tp) + p_4 Caap(t + 3Tp)$$

where $N = 4$.

Furthermore, if the autocorrelation function of the third sequence {p} is expressed by $ppp(i)$, [$i = 0, \pm 1, \pm 2, \ldots, (N-1)$], the first compressed pulse Caapp(t) will be provided as follows in accordance with equations (7) and (10).

$$Caapp(t) = ppp(0)Aa(t - t_0) + \quad (11)$$
$$\sum_{i=1}^{N-1} ppp(i)[Aa(t - t_0 - iTp) + Aa(t - t_0 + iTp)]$$
$$= ppp(0)Aa(t - t_0) +$$
$$ppp(1)[Aa(t - t_0 - Tp) + Aa(t - t_0 + Tp)] +$$
$$ppp(2)[Aa(t - t_0 - 2TP) + Aa(t - t_0 2Tp)] +$$
$$ppp(3)[Aa(t - t_0 - 3Tp) + Aa(t - t_0 + 3Tp)]$$

The second compressed pulse Caaqq(t) can be expressed by the equation which has replaced Caap(t) by Caaq(t) and also replaced $p_i$ by $q_i$ ($i = 1, 2, 3, 4$) at the right side of equation (10). It is also to be noted that this replaced equation for Caaqq(t) is equivalent to the equation which has replaced the autocorrelation function $ppp(i)$ of the third sequence {p} by the autocorrelation function $pqq(i)$ of the fourth sequence {q} at the right side of equation (11). The third compressed pulse Cbbpp(t) can be expressed by the equation which has replaced Caap(t) by Cbbp(t) at the right side of the equation (10), and is equivalent to the equation which has replaced Aa(t) by Ab(t) at the right side of equation (11). The fourth compressed pulse Cbbqq(t) can be expressed by the equation which has replaced Caap(t) by Cbbq(t) and also replaced $p_i$ by $q_i$ ($i = 1, 2, 3, 4$) at the right side of equation (10), and is equivalent to the equation which has replaced the autocorrelation function $ppp(i)$ by the autocorrelation function $pqq(i)$ and also replaced Aa(t) by Ab(t) at the right side of equation (11).

Figure 20:
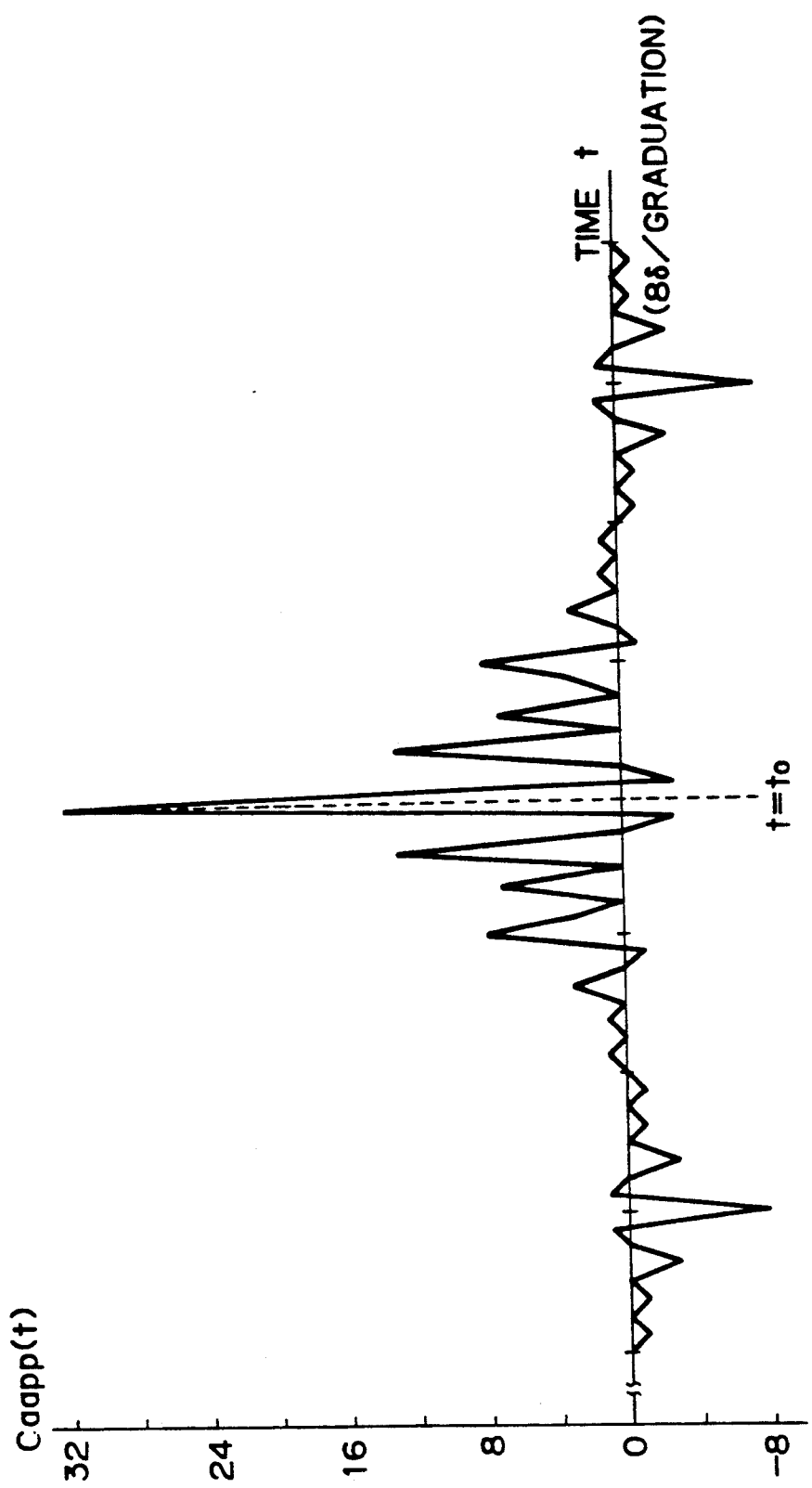
FIGS. 20-23 are waveform diagrams illustrating first through fourth compressed pulses of the first embodiment.

FIG. 20 illustrates the first compressed pulse Caapp(t) which has been provided by computation in accordance with equation (11).

In FIG. 20, the pulse shown in FIG. 12 has been used as the first basic unit compressed pulse Aa(t−t₀) and $ppp(0) = 4$, $ppp(1) = 1$, $ppp(2) = 0$ and $ppp(3) = −1$ have been used as the autocorrelation function $ppp(i)$ of the third sequence {p}. Tp has been set to be 8δ.

Figure 21:
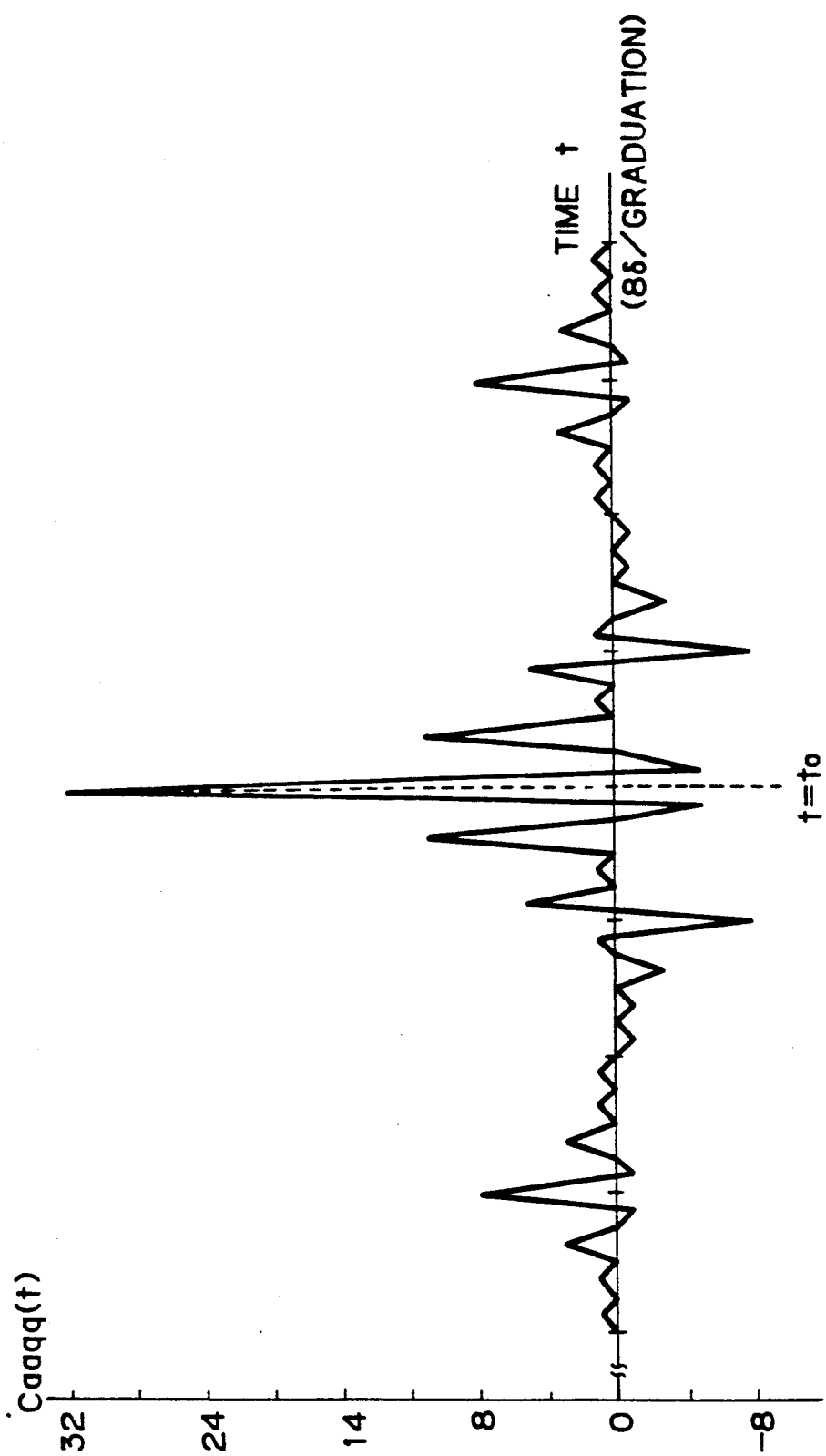
Figure 22:
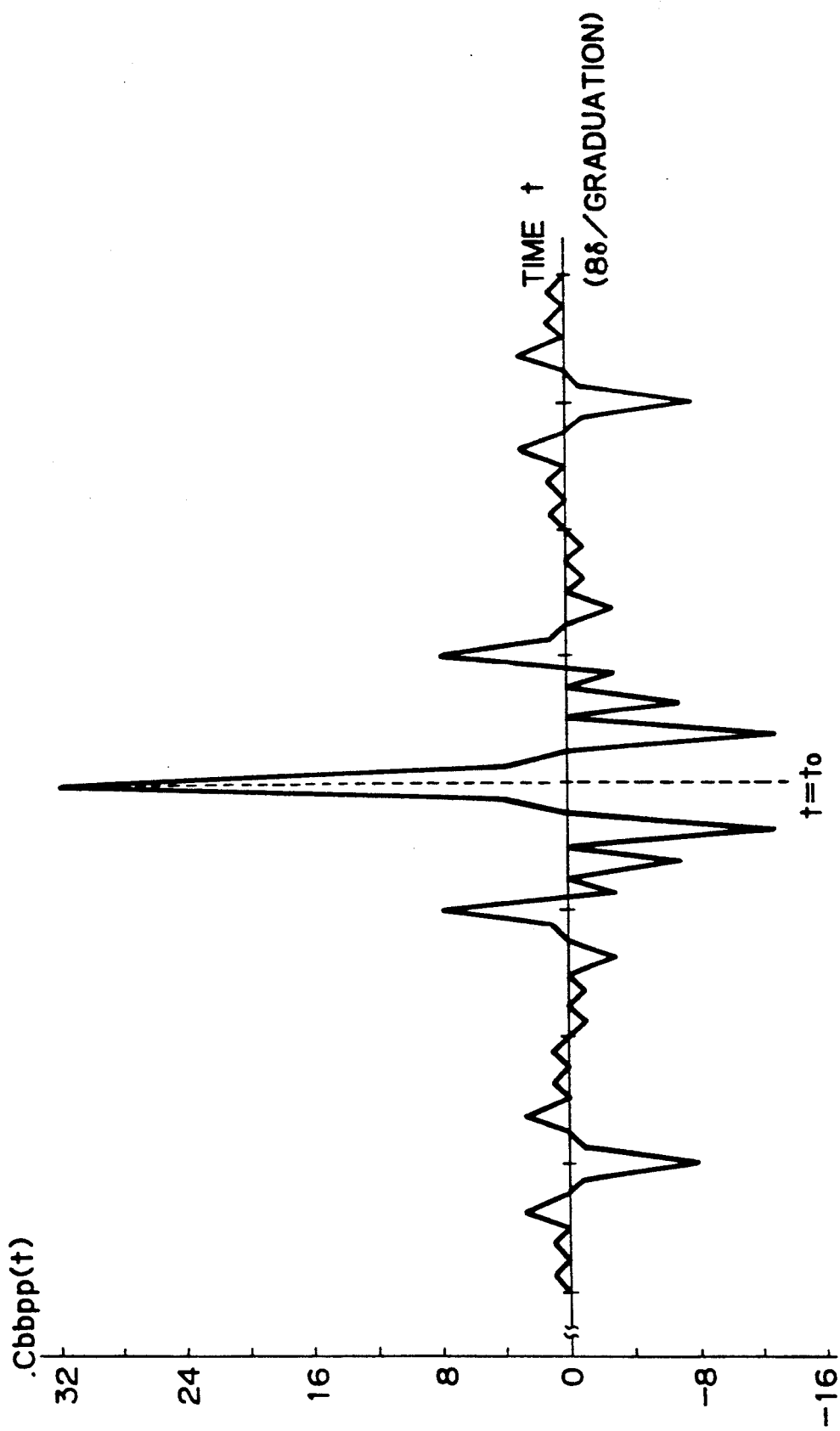
Figure 23:
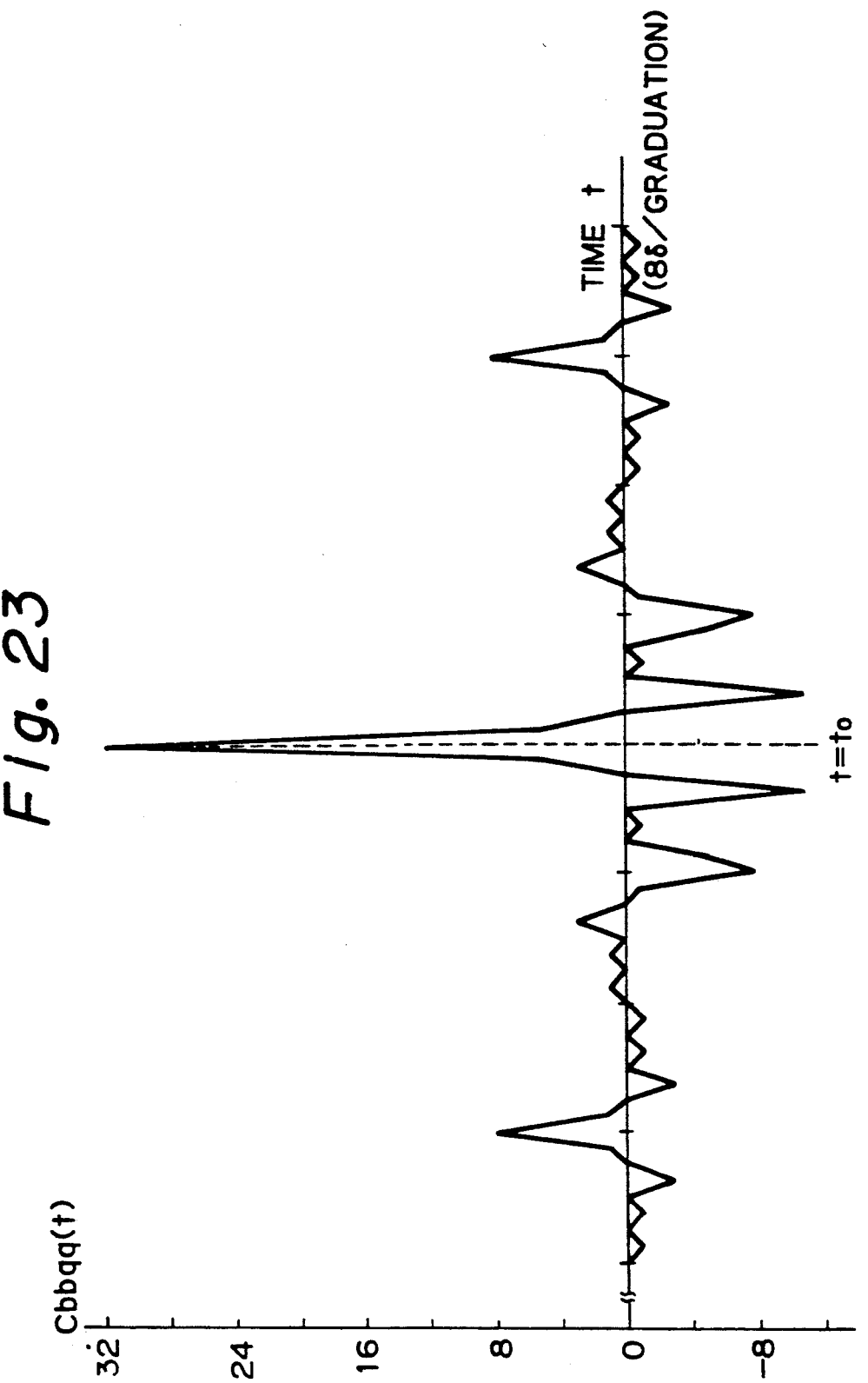

FIGS. 21 through 23 respectively illustrate the second compressed pulse Caaqq(t), the third compressed pulse Cbbpp(t) and the fourth compressed pulse Cbbqq(t) which have been obtained respectively by executing similar computations to that of the first compressed pulse Caapp(t). As the second basic unit compressed pulse Ab(t−t₀), the pulse shown in FIG. 13 has been employed. Further as the autocorrelation function $pqq(i)$ of the fourth sequence {q}, $pqq(0) = 4$, $pqq(1) = −1$, $pqq(2) = 0$ and $pqq(3) = 1$ have been applied. Also Tp = 8δ has been applied.

As apparent from FIGS. 20 through 23, the majority of the signal energy in each of the first through fourth compressed pulses is concentrated near $t = t_0$. In other words, they have large amplitudes only in the neighborhood of $t = t_0$, and they have side lobes with certain small levels. It is observed, however, that there are still relatively large side lobes even at time locations where time t is considerably spaced from $t_0$.

FIG. 24 shows the composite compressed pulse C which has been provided by summing the first through fourth compressed pulses; C = Caapp(t) + Caaqq(t) + Cbbpp(t) + Cbbqq(t). In the composite compressed pulse C, according to the summing operation, the main lobes of the pulses Caapp(t), Caaqq(t), Cbbpp(t) and Cbbqq(t) are strengthened while the side lobes thereof are cancelled and reduced to zero level, as shown in FIG. 24.

Accordingly, it would have been understood that a compressed pulse, which includes the main lobe having a large amplitude at $t = t_0$ and no side lobes, can be obtained by the embodiment of this invention mentioned above, and thus the value of $t_0$ can be easily detected.

It is further to be understood that when the first and second basic unit compressed pulses Aa(t−t₀) and Ab(t−t₀) are added together, the resultant pulse has a large amplitude, as the main lobe, only in the vicinity of $t = t_0$, and amplitudes in the other range are zero, as shown in FIG. 25. This is induced from the fact that if the autocorrelation functions of the first and second sequence {a} and {b} are expressed as $paa(i)$ and $pbb(i)$, then $paa(0) = pbb(0)$ and $paa(i) = −pbb(i)$ ($i = 1, 2, \ldots, M − 1$) can be applied. Such relationships as those between Aa(t−t₀) and Ab(t−t₀), or {a} and {b} may be called complementary relationships.

Similarly, between the third and fourth sequences {p} and {q}, $ppp(0) = pqq(0)$ and $ppp(i) = −pqq(i)$ ($i = 1, 2, \ldots, N − 1$) can be applied. Accordingly, in the embodiment described above, the first and second sequences {a} and {b} constitute complementary relationships and the third and fourth sequences {p} and {q} also constitute complementary relationships.

Another effect which can be derived by the first embodiment of the present invention will be explained.

In an inspection apparatus of this sort, improvement of S/N ratio can be more enhanced, as the duration of a transmission pulse signal becomes longer, and, in order to realize a longer pulse duration of the transmission signal, it is necessary to utilize sequences having a longer sequence length.

According to the first embodiment of the present invention, as it is seen from FIGS. 8 through 11, the pulse duration of the transmission signal depends not only on the length M of the first and second sequences {a} and {b} but also on the length N of the third and fourth sequences {p} and {q}. If the third and fourth sequences the length N of which is larger are employed, the pulse duration of the transmission signal can be made longer correspondingly.

Those sequences which are in the complementary relationships can not exist at any length but exist at specific sequence lengths. According to the first embodiment of the present invention, since two kinds of sequence length M and N are used in combination, the substantial length of the sequence of the transmission signal is M×N.

Accordingly, since the pulse duration of the transmission signal can be made longer, S/N ratio can be improved. Furthermore, by combining different lengths M and N, freedom for selection of various pulse durations for transmission signals can be provided.

Figure 26:
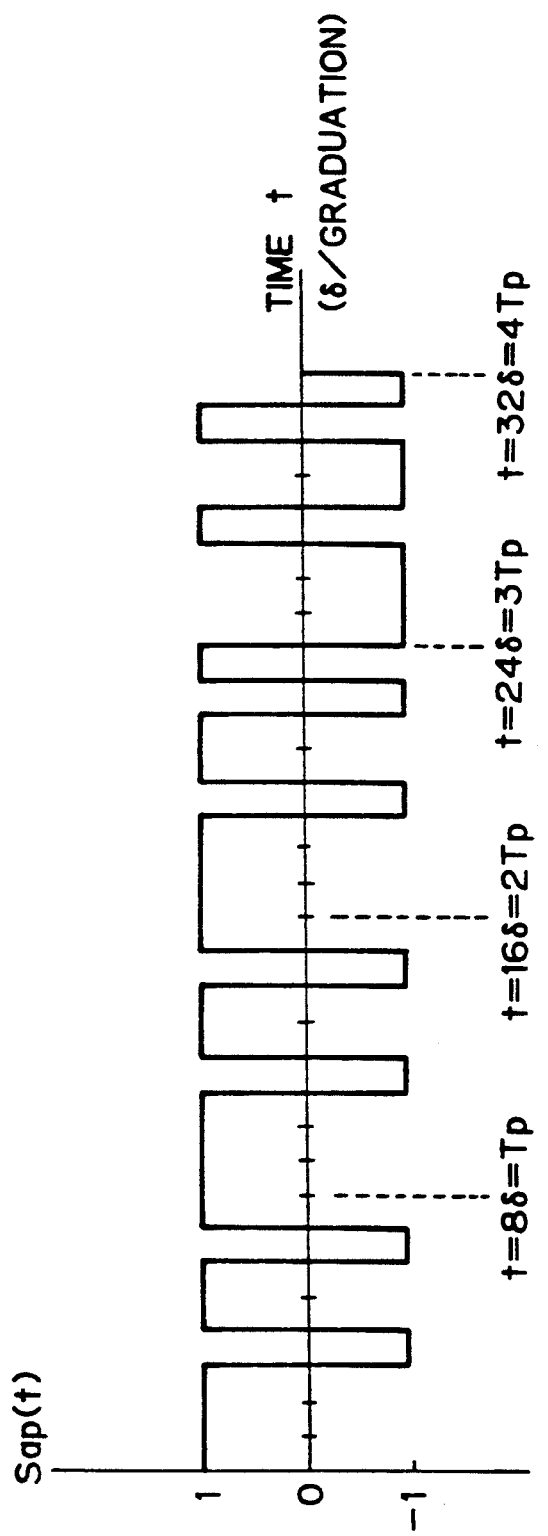
FIG. 26 is a waveform diagram illustrating another first transmission signal of the first embodiment.
Figure 27:
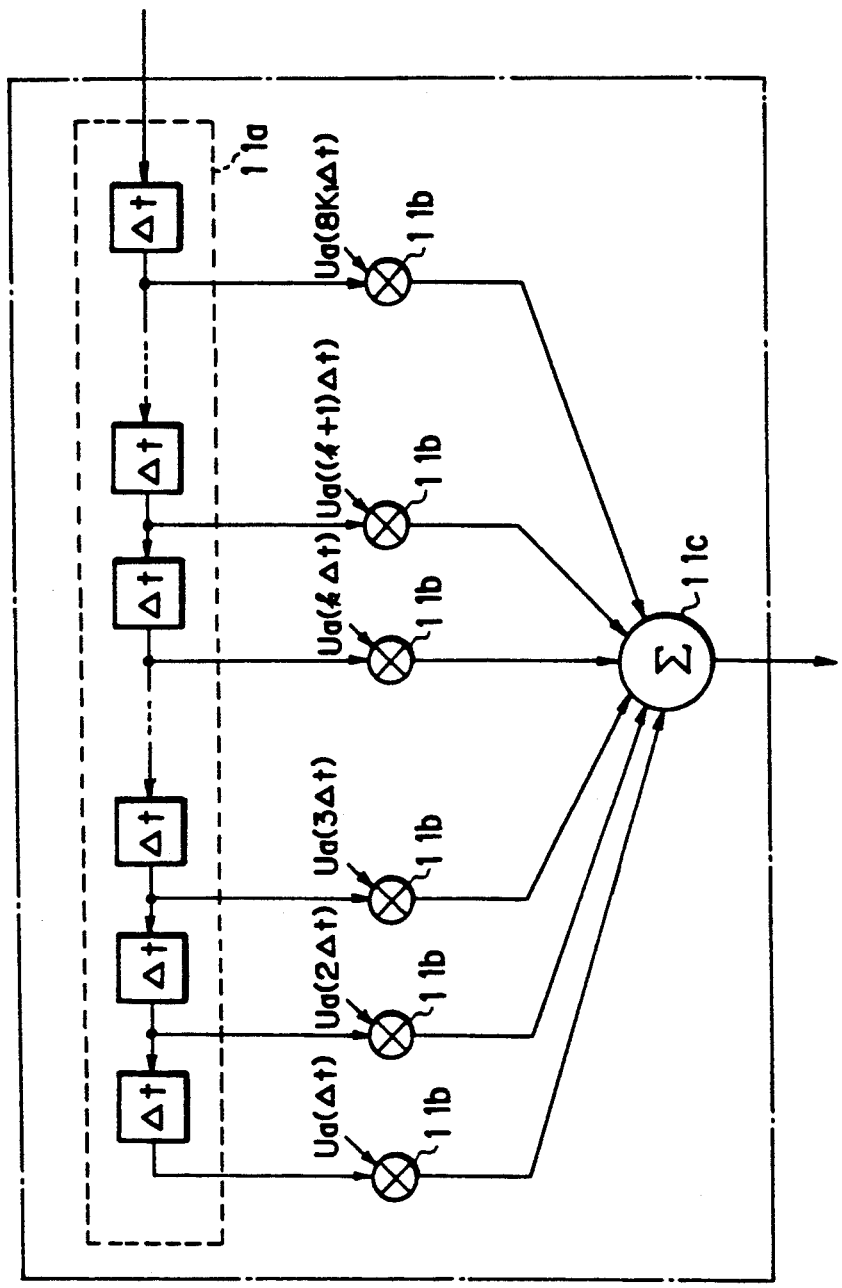
FIG. 27 is a block diagram illustrating a concrete constitution of the first correlator in the first embodiment.
Figure 28:
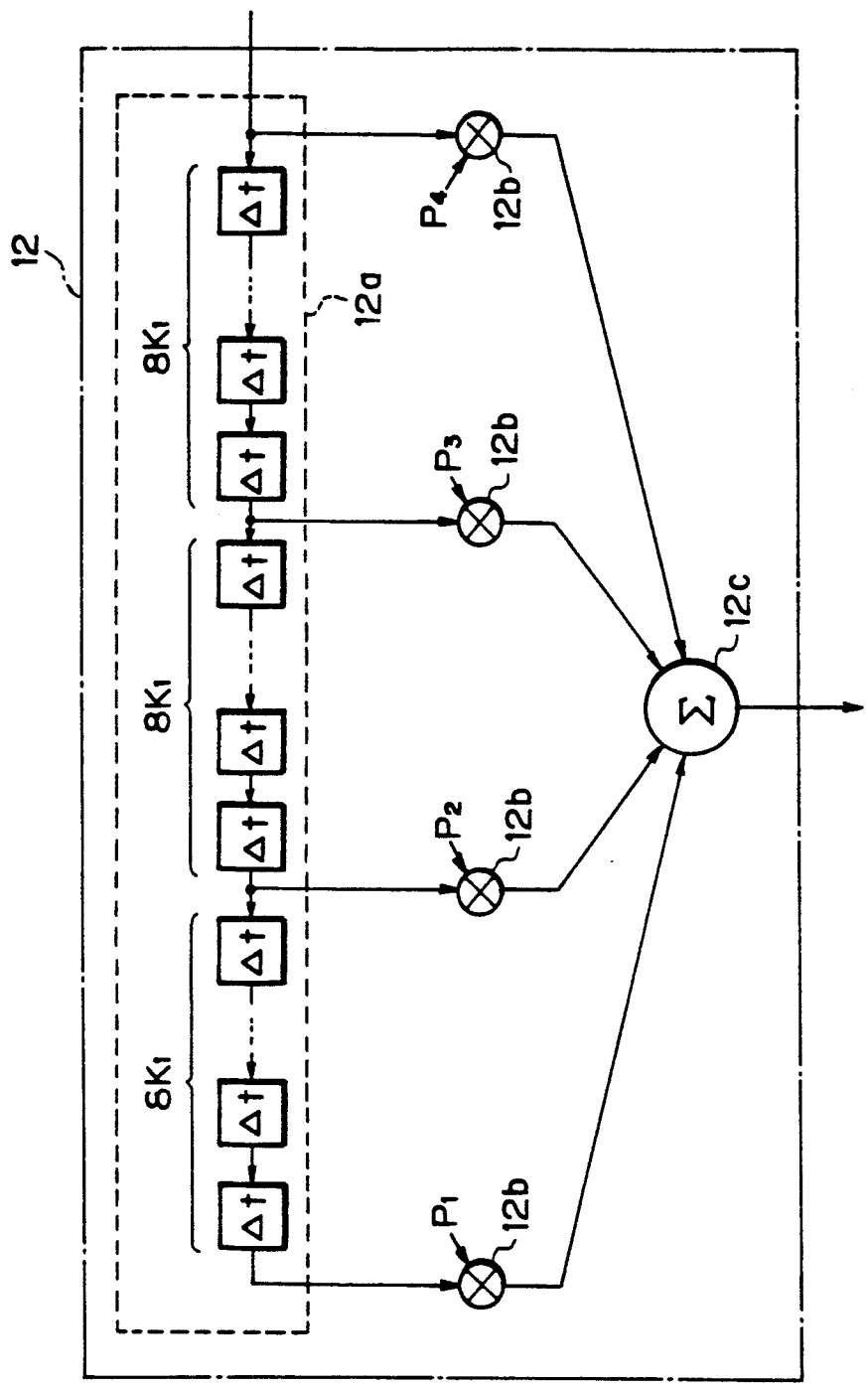
FIG. 28 is a block diagram illustrating a concrete constitution of a second correlator in the first embodiment.

Other effects of the first embodiment of the present invention will further be explained by referring to FIGS. 26 through 28.

FIG. 26 is a waveform diagram showing another first transmission signal Sap(t) when $Tp=8\delta$ according to the first embodiment of the present invention is applied.

FIGS. 27 and 28 are block diagrams illustrating constitutions of the first and second correlators 11 and 12.

The first transmission signal shown in FIG. 26 is equivalent to a signal an amplitude of which has been encoded by using the following sequence:

{+, +, +, −, +, +, −, +,
+, +, +, −, +, +, −, +,
+, +, +, −, +, +, −, +,
−, −, −, +, −, −, +, −}

It is to be noted that the above sequence is equivalent to the following sequence having a length of 32 obtained using the first and third sequences {a} and {p}:

{$a_1p_1$, $a_2p_1$, $a_3p_1$, $a_4p_1$, $a_5p_1$, $a_6p_1$, $a_7p_1$, $a_8p_1$,
$a_1p_2$, $a_2p_2$, $a_3p_2$, $a_4p_2$, $a_5p_2$, $a_6p_2$, $a_7p_2$, $a_8p_2$,
$a_1p_3$, $a_2p_3$, $a_3p_3$, $a_4p_3$, $a_5p_3$, $a_6p_3$, $a_7p_3$, $a_8p_3$,
$a_1p_4$, $a_2p_4$, $a_3p_4$, $a_1p_4$, $a_5p_4$, $a_6p_4$, $a_7p_4$, $a_8p_4$}

It is here to be noted that the symbols (+) and (−) are regarded as equivalent to +1 and −1, and thus multiplication operation is utilized.

Figure 4:
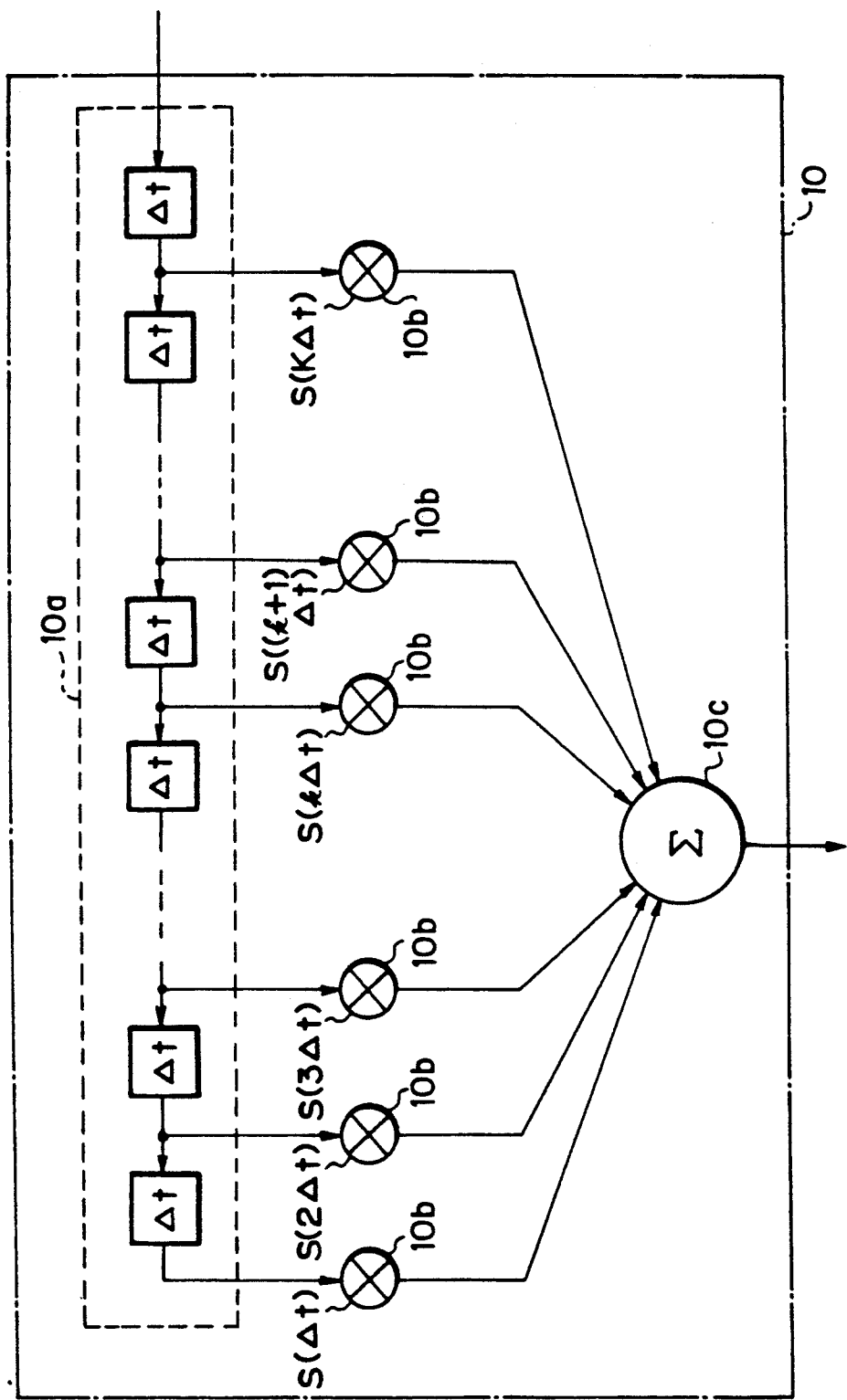
FIG. 4 is a block diagram illustrating a correlator in the prior inspection apparatus.

Next, a consideration is made on such a situation that the first transmission signal shown in FIG. 26 having a long pulse duration is employed as a transmission signal in the conventional apparatus shown in FIGS. 1 and 4 for the purpose of improving the S/N ratio.

The duration T of the transmission signal is $32\delta$ as seen from FIG. 26. Accordingly, when sampling of $K_1$ times per the unit time $\delta$ is executed and the correlator 10 shown in FIG. 4 is constituted in accordance with equation (2), since $K=32\times K_1$ is obtained, a delay line having $32\times K_1$ number of taps as the delay line 10a, $32\times K_1$ number of multipliers as the multipliers 10b, and adder having $32\times K_1$ number of input terminals as the adder 10c are required.

The inspection apparatus according to the first embodiment of the present invention utilizes the first basic unit signal ga(t) as the first reference signal, and the duration of the first basic unit signal ga(t) is $8\times\delta$ as seen from FIG. 6. Accordingly, the first correlator 11 is constituted as shown in FIG. 27 if equation (5) is modified like equation (2) and sampling of $K_1$ times is executed for the unit time $\delta$.

As shown in FIG. 27, the first correlator 11 consists of a delay line 11a with $8\times K_1$ number of output taps, $8\times K_1$ number of multipliers 11b connected to the respective output taps of the delay line 11a, and adder 11c having $8\times K_1$ number of input terminals connected to the multipliers 11b.

Consideration is next made with regard to the second correlator 12 for the inspection apparatus according to the first embodiment of the present invention.

The second correlator 12 is acceptable if it is provided with a function to compute the right side of equation (10) based on the first correlation operation result Caap(t) by the first correlator 11. The right side of equation (10) comprises Caap(t)×$p_1$ at the time t, Caap(t)×$p_2$ at the time (t+Tp), Caap(t)×$p_3$ at the time (t+2Tp), and Caap(t)×$p_4$ at the time (t+3Tp), which are summed all together. Accordingly, supposing that sampling of $K_1$ times for the unit time $\delta$ is executed, since $Tp=8\delta$, the second correlator 12 may be constituted as shown in FIG. 28.

More specifically, in FIG. 28, the second correlator 12 consists of the delay line 12a with $24\times K_1$ number of output taps, four multipliers 12b connected to the output taps of the delay line 12a for each $8\times K_1$ number of output taps (corresponding to each Tp) and adder 12c having four input terminals connected to the multipliers.

Now, the aggregate number of the multipliers 11b and 12b required by the first and second correlators 11 and 12 of the first embodiment of the present invention is compared to the number of the multipliers 10b required by the correlator 10 shown in FIG. 4 of the conventional inspection apparatus. According to the former, the total ($8\times K_1+4$) of the multipliers are required while $32\times K_1$ number of the multipliers are required for the latter. Namely, a large number of the multipliers can be dispensed with according to the first embodiment of the present invention. In this way, reduction of the number of the multipliers contributes to higher operational speed of the apparatus and reduction in costs.

Furthermore, weighting $p_i$ (i=1, 2, 3, 4) of the multipliers 12b required at the second correlator 12 is either ±1 according to the first embodiment as described above. If weighting is ±1, this means that the multipliers 12b are not necessary. If weighting is −1, this means that the multipliers 12b may be replaced by inverters. Accordingly, the first embodiment of the present invention is increasingly advantageous in terms of higher speed and lower cost.

Similar comparison is next made with regard to the adders. The first embodiment of the present invention requires the adder 11c having $8\times K_1$ number of the input terminals, and the adder having four input terminals. On the other hand, the conventional apparatus requires the adder having $32\times K_1$ number of the input terminals. Since, in general, an adder operates to add input values accumulatively, the less the number of input terminals is required, the more the operational speed can be increased and the more the cost can be reduced. Accordingly, those are further advantages of the first embodiment.

For correlation processing of the second echo signal, the same correlator as the one shown in FIG. 27 can be used as the first correlator 11, and the second correlator 12 shown in FIG. 28 but which has replaced the weighting $p_i$ ($i=1, 2, 3, 4$) for the multiplier 12b by $q_i$ can be utilized.

For correlation processing of the third echo signal, the correlator shown in FIG. 27 but which has replaced the weighting Ua(k$\Delta$t) (k=1, 2, ..., 8K$_1$) for the multiplier 11b by Ub(k$\Delta$t) can be used as the first correlator 11, and as the second correlator 12, the one identical to the one shown in FIG. 28 can be used.

For correlation processing of the fourth echo signal, the correlator such as shown in FIG. 27 but which has replaced the weighting Ua(k$\Delta$t) (k=1, 2, ..., 8K$_1$) for the multiplier 11b by Ub(k$\Delta$t) can be used as the first correlator 11, and as the second correlator 12, such a correlator as identical with the one shown in FIG. 28 but which has replaced the weighting $p_i$ ($i=1, 2, 3, 4$) for the multiplier 12b by $q_i$ can be utilized. Or the first and second correlators may be independently provided for correlation processing of the second, third and fourth echo signals.

Figure 29A:
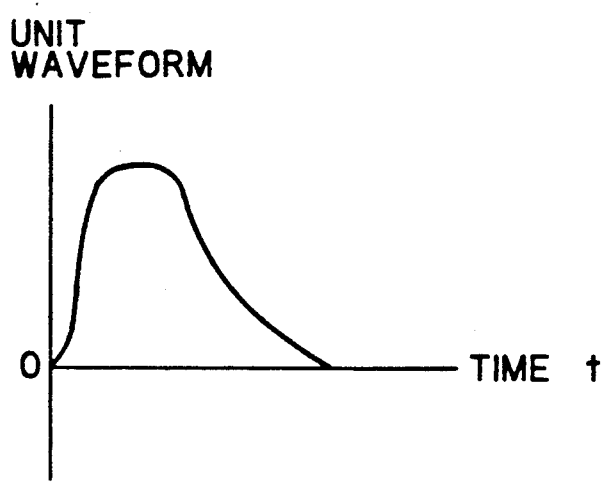
FIGS. 29(a) and 29(b) are waveform diagrams illustrating other unit waveforms utilizable in the first embodiment.
Figure 29B:
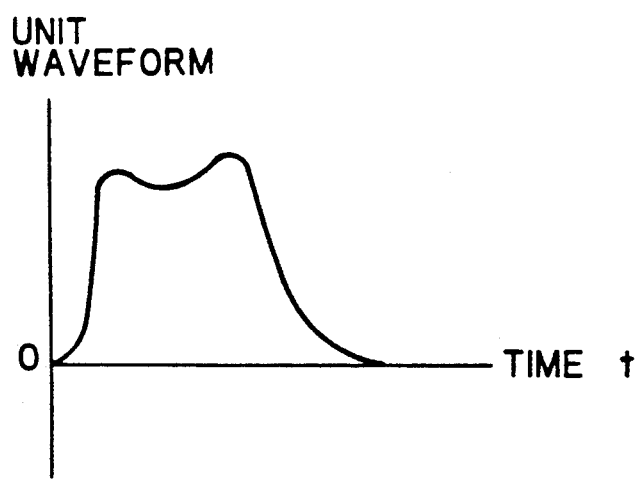

With reference to the first embodiment as described above, the unit waveform corresponding to the respective components ($\pm$) of the first and second sequences {a} and {b} has been described as rectangular in the first and second basic unit signals, as shown in FIGS. 6 and 7. However, even if the unit waveform is modified to such a shape rather than rectangular as shown in FIGS. 29(a) or 29(b), similar function and effects to those explained above can be attained.

Figure 30:
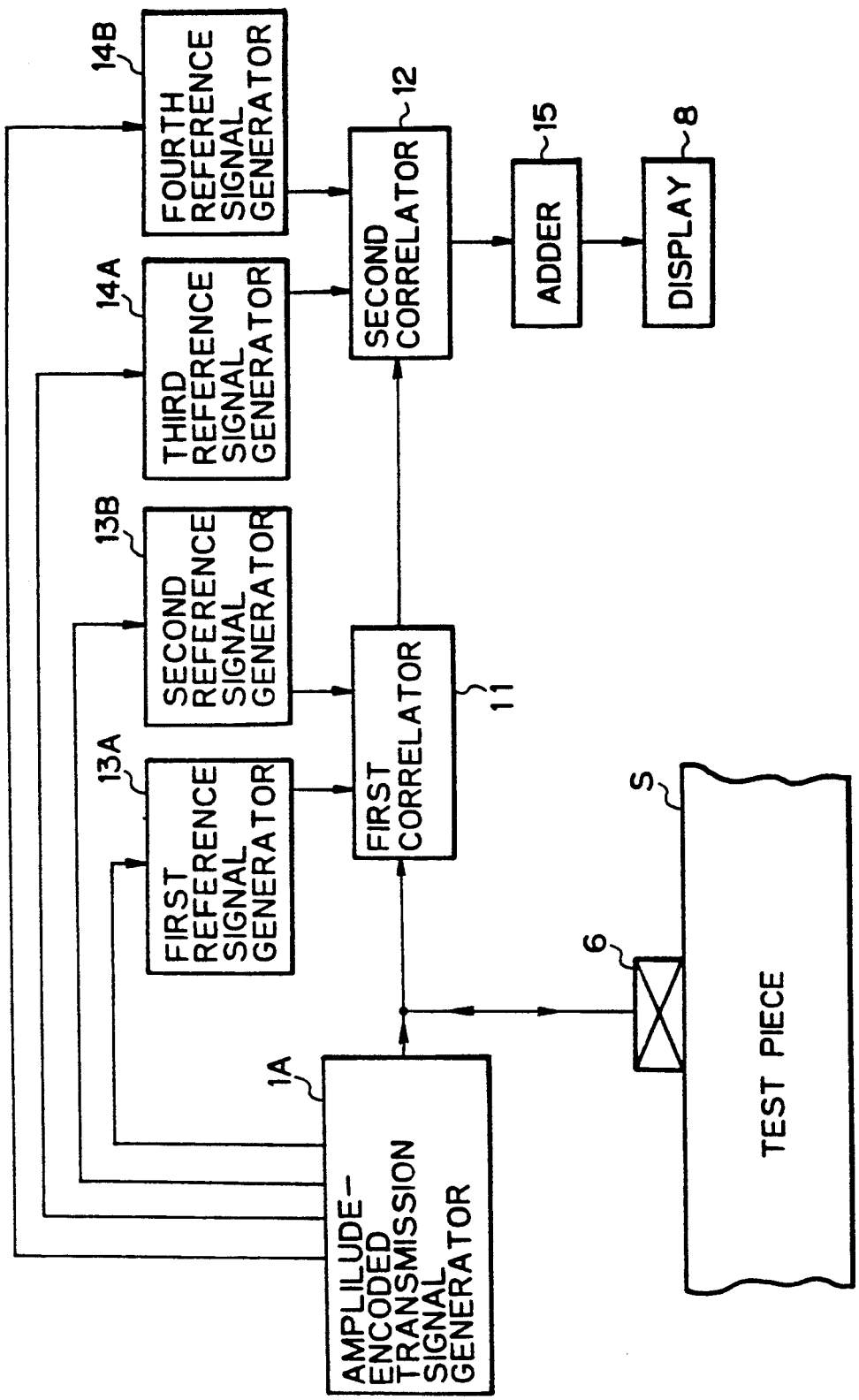
FIG. 30 is a block diagram illustrating a second embodiment of the present invention.

Constitution of a second embodiment of the present invention will now be explained by referring to FIG. 30.

In this drawing, first and second correlators 11 and 12, adder 15, ultrasonic prove 6 and display 8 are identical to those in the first embodiment, however, amplitude-encoded transmission signal generator 1A does not have the same constitution and function as those of the generator 1A in the first embodiment. That is, in the second embodiment, although the generator 1A is constituted to generate the first through fourth transmission signals Sap(t), Saq(t), Sbp(t) and Sbq(t) in the same manner as that of the first embodiment, but none of the first through fourth reference signals Ua(t), Ub(t), Up(t) and Uq(t). Instead thereof, first through fourth reference signal generators 13A, 13B, 14A and 14B are incorporated thereinto as shown in FIG. 30.

The generators 13A and 13B are enabled by the transmission signal generator 1A to generate first and second reference signals having waveforms similar to or identical with waveforms of echo signals which are obtained when the probe 6 is driven by the first and second basic unit signals ga(t) and gb(t), respectively. These generated reference signals are sent to the first correlator 11.

On the other hand, the generator 14A and 14B are enabled by the generator 1A to generate third and fourth reference signals having waveforms similar to or identical with those of the third and fourth reference signals Up(t) and Uq(t) in the first embodiment, and supplies them to the second correlator 12.

The reference signals generated by the generators 13A and 13B are identical to or similar to the signals expressed by the right side of equation (4) but Sap(t) has been replaced by ga(t) and gb(t), respectively. Accordingly, each of the generators 13A and 13B functions as a filter having frequency response characteristics in both transmission and reception of the ultrasonic probe 6, those of the test piece S and those relating to the ultrasonic reflection from the reflective portion such as defects in the test piece S.

Correlation processing of echo signals by utilizing reference signals having waveforms identical to or similar to waveforms of echo signals such as the first and second reference signals generated by the generators 13A and 13B is equivalent to signal processing causing the echo signal to pass through a matching filter or a quasi-matching filter which is effective in receiving a signal buried in noises with the maximum S/N ratio.

Accordingly, the second embodiment of the present invention can derive an advantage of further improving the S/N ratio in addition to the advantages provided by the first embodiment which utilizes the first and second basic unit signals themselves as the reference signals for the first correlator 11.

It is to be understood that the generators 13A and 13B are acceptable if they have the function of generating the following reference signals.

Firstly, in the case where a surface of bottom echo reflected by the front or bottom surface of the test piece S and received by the ultrasonic probe 6 when the ultrasonic probe 6 is driven by the first basic unit signal ga(t) can be measured and provided with a large S/N ratio, a waveform of an echo signal corresponding to the front or bottom surface echo is measured and a signal having a waveform identical to or similar to the measured waveform is generated as the first reference signal by the first reference signal generator 13A. The second reference signal from the second reference signal generator 13B is similarly generated, but the second basic unit signal gb(t) is used instead of the first one.

If an adequate S/N ratio cannot be attained by the echo reflected from the front or bottom surface of the test piece S, then another test piece S$_1$ should be prepared. Then, similarly to the above, the ultrasonic probe 6 is driven by the first and second basic unit signals ga(t) and gb(t) respectively, the echoes reflected from the test piece S$_1$ are received by the ultrasonic probe 6, and signals having waveforms identical to or similar to those of the corresponding echo signals are generated as the reference signals by the generators 13A and 13B.

The generator 13A may be constituted as to generate a reference signal having a waveform computed in accordance with frequency response characteristics of a signal transmission path from the output terminal of the amplitude-encoded transmission signal generator 1A through the ultrasonic probe 6, the test piece S and again the ultrasonic probe 6 to the input terminal of the first correlator 11 as well as the first basic unit signal when the ultrasonic probe 6 is driven by the first basic unit signal. Similarly, the generator 13B may be constituted in considering the second basic unit signal. In these cases, if frequency response characteristics relating to reflection by the reflective body in the test piece S is involved in the frequency response characteristics of the signal transmission path, S/N ratio may further be enhanced.

Further, if a plurality of the first and second reference signals which have different frequency response characteristics related to reflection from the reflection body in the test piece S are prepared to be generated, the function of discriminating the reflective bodies may be additionally provided as disclosed in the Japanese Patent Application No. 86383/89 relating to the field of the present invention.

With regard to the third and fourth reference signal generators, the generators 14A and 14B may be constituted to generate signals, as the third and fourth reference signals, amplitudes of which are slightly changed from ±1 for each time Tp. The signals enabling the first through fourth compressed pulses Caapp(t), Caaqq(t), Cbbpp(t) and Cbbqq(t), and/or the composite compressed pulse C to be provided at a high S/N ratio may be generated as the third and fourth reference signals.

According to the second embodiment of the present invention, supposing that there are $K_3$ number of sampling points in the time duration of the first or second reference signal and $K_2$ number of sampling points in the time duration Tp, the first correlator 11 may be constituted, in the similar manners to illustration of FIG. 27, by a delay line with $K_3$ number of taps, $K_3$ number of multipliers connected to the respective output taps of the delay line and an adder with $K_3$ number of input terminals, as it is seen if equation (5) is changed like equation (2). The second correlator 12 may be constituted, in the similar manner to illustration of FIG. 28, by a delay line having $(N-1) \times K_2$ number of taps, N number of multipliers connected to the output taps of the delay line for every $K_2$ number of taps and an adder having N number of input terminals. Weightings of $p_i$ and $q_i (i = 1, 2, 3, \ldots, N)$ to N number of multipliers may be executed as ±1, or as explained above, it may be changed from ±1 respectively for every i so that the first through fourth compressed pulses and hence the composite compressed pulse may be obtained at a high S/N ratio.

Figure 31:
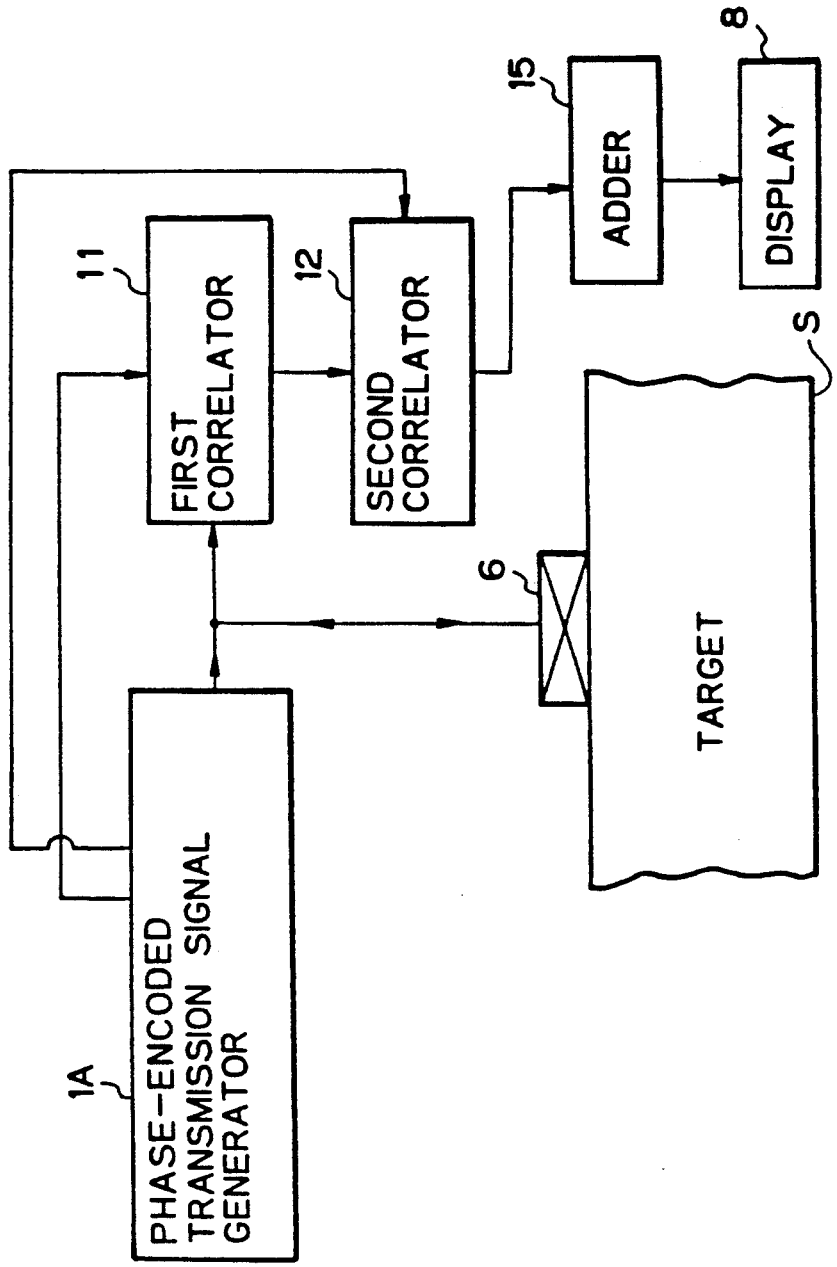
FIG. 31 is a block diagram illustrating a third embodiment of the present invention.

Constitution of a third embodiment of the present invention will now be explained by referring to FIG. 31.

The third embodiment comprises the same components as those in the first embodiment except a phase-encoded transmission signal generator 1B is substituted for the amplitude-encoded transmission signal generator 1A in the first embodiment.

Operation of the third embodiment will be explained by referring to FIGS. 32 through 38.

Figure 32:
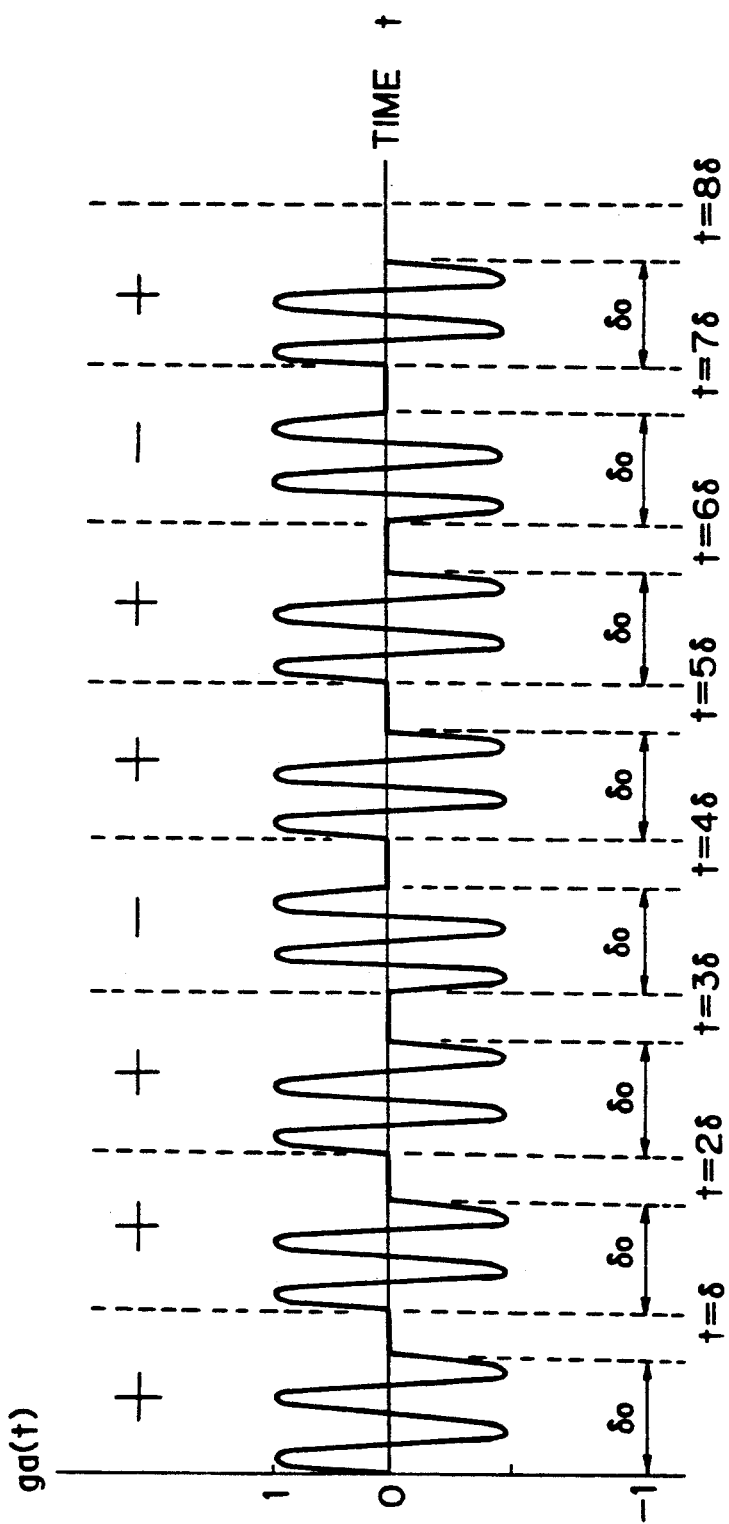
Figure 34A:
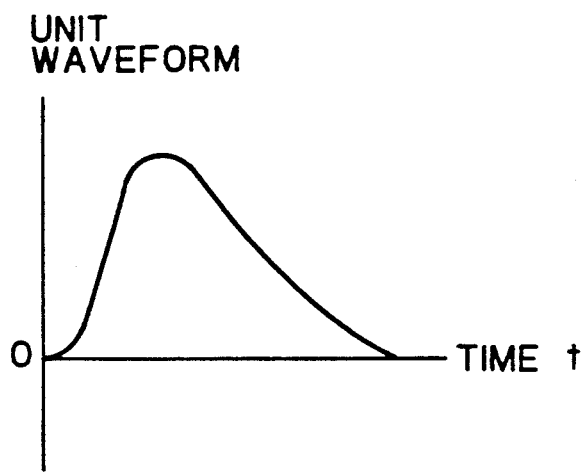
FIG. 34 is a waveform diagram illustrating other unit waveforms utilizable in the third embodiment.

FIGS. 32 and 33 are waveform diagrams illustrating first and second basic unit signals ga(t) and gb(t) in the third embodiment. FIGS. 34(a) and (b) are waveform diagrams illustrating other unit waveforms constituting the basic unit signals. FIGS. 35 through 38 respectively show waveforms of first through fourth transmission signals Sap(t), Saq(t), Sbp(t) and Sbq(t).

In FIG. 32, the first basic unit signals ga(t) is a signal generated using the same first sequence {a} as that in the first embodiment, and $\delta$ and $\delta_0$ designate fixed times. For better understanding of relationships between the first sequence {a} and the first basic unit signal ga(t), the symbols (+) and (−) of the first sequence {a} are also indicated in the drawing.

In FIG. 33, the second basic unit signal gb(t) is a signal generated by using the same second sequence {b} as that in the first embodiment. The symbols (+) and (−) of the second sequence {b} are also indicated in the drawing.

In FIGS. 32 and 33, the unit waveforms correspondingly shown to the respective components (+) and (−) of the first or second sequences {a} and {b} are illustrated as sinusoidal waves. The above-mentioned unit waveforms may take waveforms having smooth curves or oscillation waveforms having non-uniform amplitudes and/or zero-crossing points as shown in FIG. 34(a) or (b).

It is to be noted from FIGS. 32 and 33 that when $\delta = \delta_0$, the first and second basic unit signals ga(t) and gb(t) may have waveforms which have been phase-encoded. Methods of phase-encoding are described in detail in the Japanese Patent Application No. 45316/89 to which the present invention relates.

In FIG. 35, the first transmission signal Sap(t) is a signal that has been generated in the same steps as those in the first embodiment by using the same third sequence {p} as in the first embodiment and the first basic unit signal ga(t) shown in FIG. 32. More specifically, the first basic unit signal ga(t) is allocated to the symbol (+) of the third sequence {p}, the signal −ga(t) obtained by multiplying the first basic unit signal ga(t) by −1 is allocated to the symbol (−) and ±ga(t) are arranged along the time base in the appearance order of the symbol of the third sequence {p}. For better understanding of the relationships between the symbols (+) and (−) of the third sequence {p} and the signals ±ga(t), the symbols of the third sequence {p} are also indicated in the drawing.

In FIG. 36, the second transmission signal Saq(t) is a signal which has been generated in the same steps of the first embodiment by using the same fourth sequence {q} as that employed in the first embodiment and the first basic unit signal ga(t) shown in FIG. 32. Similarly to FIG. 35, symbols (+) and (−) of the fourth sequence {q} are also indicated therein.

In FIG. 37, the third transmission signal Sbp(t) is a signal that has been generated in the same steps as those of the first embodiment in accordance with the same third sequence {p} as that in the first embodiment and the second basic unit signal gb(t) shown in FIG. 33, and the symbols (+) and (−) corresponding to the component symbols of the third sequence {p} are also indicated.

In FIG. 38, the fourth transmission signal Sbq(t) is a signal that has been generated in the same steps as those of the first embodiment in accordance with the same fourth sequence {q} as that in the first embodiment and the second basic unit signal gb(t) shown in FIG. 33, and the symbols (+) and (−) correspond to the component symbols of the fourth sequence {q}.

According to the third embodiment, the first, second, third and fourth transmission signals shown in FIGS. 35 through 38 are supplied from the phase-encoded transmission signal generator 1B to drive the ultrasonic probe 6. Signal processing of echo signals is similar to that of the first embodiment. Namely, the first basic unit signal ga(t) shown in FIG. 32 is utilized as the first reference signal for the first correlator 11, the second basic unit signal gb(t) shown in FIG. 33 is utilized as the second reference signal for the correlator 11 and signals exactly same as the third and fourth reference signals in the first embodiment are used as the third and fourth reference signals for the second correlator 12, in the third embodiment.

Figure 34B:
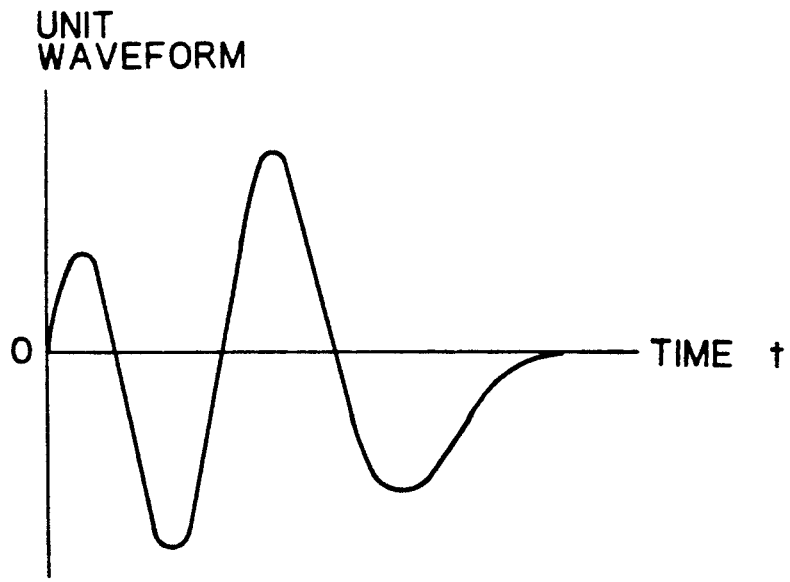

Also according to the third embodiment, the same function and advantages as those of the first embodiment may be provided, because equations (3) through (11) are applicable regardless of the waveform of the first basic unit signal ga(t), a composite basic unit compressed pulse, which is the result of summing up of the first and second basic unit compressed pulses Aa(t) and Ab(t) obtained by utilizing the first and second basic unit signals shown in FIGS. 32 and 33 in equations (6)

and (8), provides a large amplitude only around t=t₀ while the zero amplitude at the others, in other words, Aa(t) and Ab(t) are in the complementary relationship, and the third and fourth sequences {p} and {q} are in the complementary relationships. The complementary relationships between the first and second basic unit compressed pulses as described above are also applicable when the unit waveform shown in FIG. 34(a) or 34(b) is used, so that the similar effects as those of the first embodiment may also be obtained in these cases.

As explained above, the third embodiment can derive similar function and effects to those of the first embodiment. Further, in the third embodiment, frequency characteristics can be made close to those which are composed of the frequency characteristics of the ultrasonic probe 6 both in transmission and reception, the frequency characteristics of the test piece S and the frequency characteristics of the ultrasonic reflection of the reflection body in the piece S, as understood from Japanese Patent Application Nos. 45316/89 and 86383/89 to which the present invention also relates.

Accordingly, a high utilization efficiency of the signal energy can be expected. If the unit waveforms corresponding to the components (+) and (−) of the first and second sequences {a} and {b}, as shown in the period $\delta_0$ of FIG. 32 or 33 or in FIG. 34(a) or 34(b), are so selected that it has frequency characteristics close to the composite frequency characteristics as described above, the utilizing efficiency of the signal energy may be increasingly enhanced and thus S/N ratio may be increased.

When the first correlator 11 and the second correlator 12 are constituted by a delay line with taps, multipliers and an adder, the same constitution as that in the first embodiment can be employed.

Constitution of a fourth embodiment of the present invention will next be explained by referring to FIG. 39.

The fourth embodiment comprises exactly the same components as those of the second embodiment as described above except that a phase-encoded transmission signal generator 1B is employed instead of the amplitude-encoded transmission signal generator 1A of the second embodiment.

The generator 1B is adapted to generate the same first and second basic unit signals ga(t) and gb(t) as in the third embodiment to the respective first and second reference signal generator 13A and 13B, where first and second reference signals having waveforms identical to or similar to those of echo signals which are obtained when the ultrasonic probe 6 is driven with the signals ga(t) and gb(t) in the third embodiment are generated to be sent to the first correlator 11.

The third and fourth reference signal generators 14A and 14B respectively generate third and fourth reference signals having waveforms identical to or similar to those in the third embodiment to be sent to the second correlator 12.

In the fourth embodiment, the first and second reference signals are identical to or similar to the signals which are obtained from equation (4) in which Sap(t) is replaced by the respective first and second basic unit signals ga(t) and gb(t) in the third embodiment at the right side thereof. Accordingly, the fourth embodiment may derive the same advantages of the second embodiment in addition to those of the third embodiment.

It is also to be noted that the generators 13A and 13B in the fourth embodiment may be constituted in other types similar to those explained in connection with the second embodiment.

Also in the fourth embodiment, the generators 14A and 14B may be constituted to generate signals as the third and fourth reference signals having amplitudes slightly varied from ±1 for every time Tp, similarly to the second embodiment. That is, the third and fourth reference signals having the waveforms enabling the first through fourth compressed pulses and/or the composite compressed pulse to be obtained at a high S/N ratio may be generated.

The first correlator 11 and the second correlator 12 may be constituted in a similar manner to that in the second embodiment.

Constitution of a fifth embodiment of the present invention will now be explained by referring to FIG. 40.

The fifth embodiment comprises the same elements as those of the fourth embodiment except that an ultrasonic probe 6A for transmission and an ultrasonic probe 6B for reception are employed in this embodiment.

The fifth embodiment has advantages similar to those of the fourth embodiment.

It is naturally possible to apply the ultrasonic probe 6A and the ultrasonic probe 6B to the first, second and third embodiments of the present invention.

Figure 41:
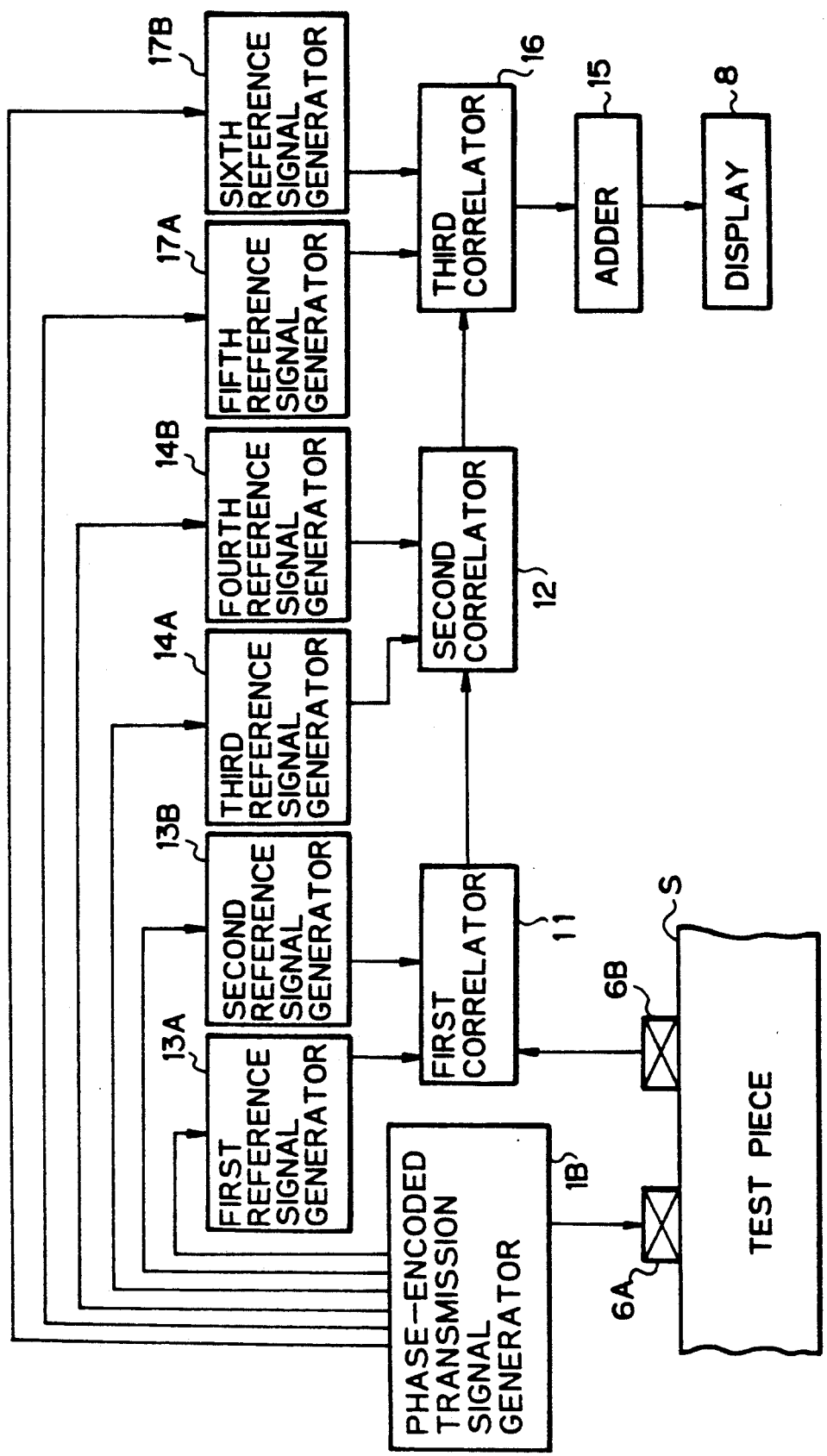

Constitution of a sixth embodiment of the present invention will be explained by referring to FIG. 41.

Figure 40:
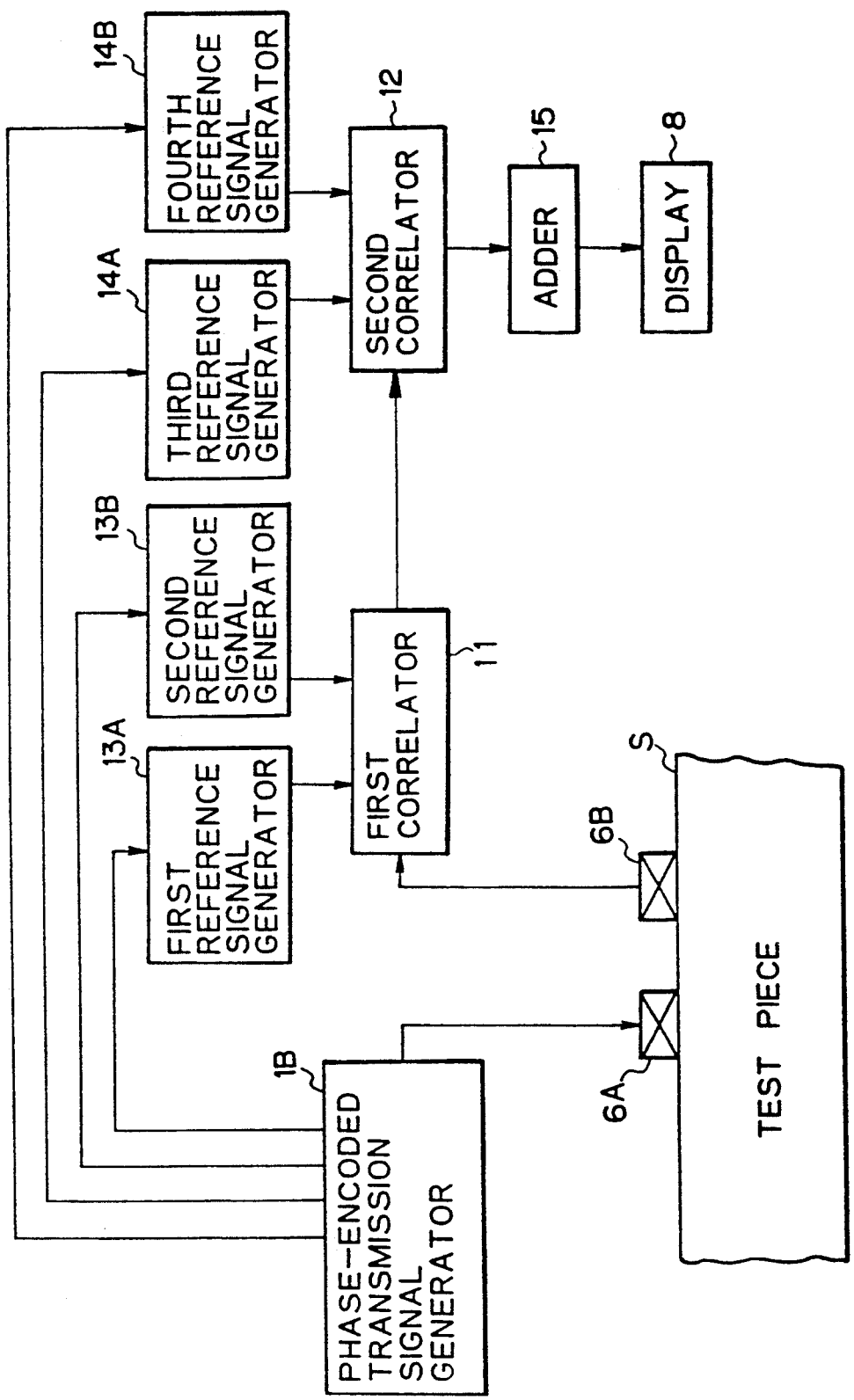

The sixth embodiment consists components identical to the fifth embodiment shown in FIG. 40 except that a third correlator 16, fifth and sixth reference signal generators 17A and 17B are newly incorporated in this sixth embodiment.

The generators 17A and 17B are connected to receive signals from the phase encoded transmission signal generator 1B and the third correlator 16 is connected to receive signals from the second correlator 12 and the generators 17A and 17B and to supply its output signal to the adder 15.

According to the sixth embodiment, the transmission signal generator 1B is adapted to newly generate fifth and sixth sequences {v} and {w} and also new first transmission signals by assuming the first through fourth transmission signals Sap(t), Saq(t), Sbp(t) and Sbq(t) as shown in FIGS. 35-38 relating to the fifth embodiment respectively as new first through fourth basic unit signals designated as $g_1(t)$, $g_2(t)$, $g_3(t)$, $g_4(t)$ and also by utilizing the fifth sequence {v} and the first basic unit signal $g_1(t)$. The steps of generating this first transmission signal follow the same steps of generating the first transmission signal Sap(t) as applied in the fifth embodiment by utilizing the first basic unit signal ga(t) and the third sequence {p}.

That is, the first basic unit signal $g_1(t)$ is allocated to the component symbol (+) of the fifth sequence {v}, the signal $-g_1(t)$ obtained by multiplying the first basic unit signal $g_1(t)$ by $-1$ is applied to the component symbol (−) thereof and these signals $g_1(t)$ and $-g_1(t)$ are arranged in the appearing order of the symbols (+) and (−) of the fifth sequence {v}. The time duration for each symbol is decided to be Tpp.

Furthermore, new second, third and fourth transmission signals are generated in a similar manner by utilizing respectively the sequence {v} and the second basic unit signal $g_2(t)$, the sequence {v} and the third basic unit signal $g_3(t)$, and the sequence {v} and the fourth basic unit signal $g_4(t)$. Furthermore, fifth through eighth transmission signals are generated by respectively utilizing the sixth sequence {w} and the first basic unit signal $g_1(t)$, the sequence {w} and the second basic unit signal $g_2(t)$, the sequence {w} and the third basic unit signal $g_3(t)$, and the sequence {w} and the fourth basic unit signal $g_4(t)$.

And these first through eighth transmission signals are sent to the ultrasonic probe 6A with a constant repetition period.

The generators 17A and 17B are adapted to generate respective fifth and sixth reference signals identical to or similar to signals amplitudes of which have been encoded by using the fifth and sixth sequences {v} and {w} and transmit them to the third correlator 16.

The correlator 16 is adapted to execute correlation processing of outputs from the second correlator 13, relating to the first through fourth transmission signals, by utilizing the fifth reference signal. It is further adapted to execute correlation processing of the outputs from the correlator 12, relating to the fifth through eighth transmission signals, by utilizing the sixth reference signal and transmit the results of these correlation processing to the adder 15.

The adder 15 in turn stores the results from the third correlator 16 relating to the first through eighth transmission signals, adds them to obtain a composite compressed pulse and transmit the composite compressed pulse to the display 8.

In this case, if the fifth and sixth sequences {v} and {w} are in the complementary relationships, the composite compressed pulse will provide a zero range side lobe.

It is further to be noted that when the third correlator 16 is constituted by a delay line with taps, multipliers and an adder, such a constitution is similar to that of the second correlator 12. It is to be understood, however, that if the length of each of the fifth and sixth sequences {v} and {w} is assumed to be L, the total number L of the multipliers should be provided to connect to the output taps spaced to each other corresponding to the time interval Tpp. The adder should also be provided with L number of input terminals.

According to the sixth embodiment, the duration time of each of the transmission signals can be made longer than in the case of the fifth embodiment. In this way, the longer is the duration of the transmission signals, the number of the multipliers as well as the number of the input terminals of the adder may be relatively decreased in comparison with a prior art as mentioned above, so that more advantage can be provided in respect of the operational speed and the cost.

Furthermore, by repeating the steps of generating the transmission signal in the sixth embodiment, or repeating the waveforms of the transmission signals to assume the repeated waveforms as a new basic unit signal and providing seventh, eighth, ninth, tenth, . . . reference signal generators and fourth, fifth, . . . correlators corresponding to the newly assumed basic unit signal, the duration of a new composite transmission signal S can further be prolonged, such that differences in the number of the multipliers and the number of the input terminals of the adder between such an inspection apparatus operable to generate the above new composite transmission signal and a prior art operable to generate a similar long duration transmission signal may be relatively increased resulting in more and more advantages in respect of operational speed and cost.

The generation steps of such a composite transmission signal having a long duration as described above regarding the sixth embodiment can be naturally applied to the first through fourth embodiments.

Various modification will next be explained.

First will follow an explanation of a modification wherein the second sequence {b} is not utilized in the generator 1A in the first embodiment shown in FIG. 5, and thus no second reference signal Ub(t) and neither third nor fourth transmission signal Sbp(t), Sbq(t) is generated from the generator 1A.

In this case, the composite transmission signal S from the generator 1A is comprised of the first and second transmission signals Sap(t) and Saq(t), and accordingly, the composite echo signal R includes the first and second echo signals Rap(t) and Raq(t) but not either the third or fourth echo signal Rbp(t) and Rbq(t).

The first correlator 11 performs a correlation-operation between the first reference signal Ua(t) and the first and second echo signals Rap(t) and Raq(t) to provide the correlation results Caap(t) and Caaq(t), and the second correlator 12 performs the correlation-operation between the correlation results Caap(t) and the third reference signal Up(t), and between the correlation results Caaq(t) and the fourth reference signal Uq(t) to provide the first and second correlation results Caapp(t) and Caaqq(t). These results are then summed at the adder 15 to provide the composite compressed pulse C.

Figure 42:
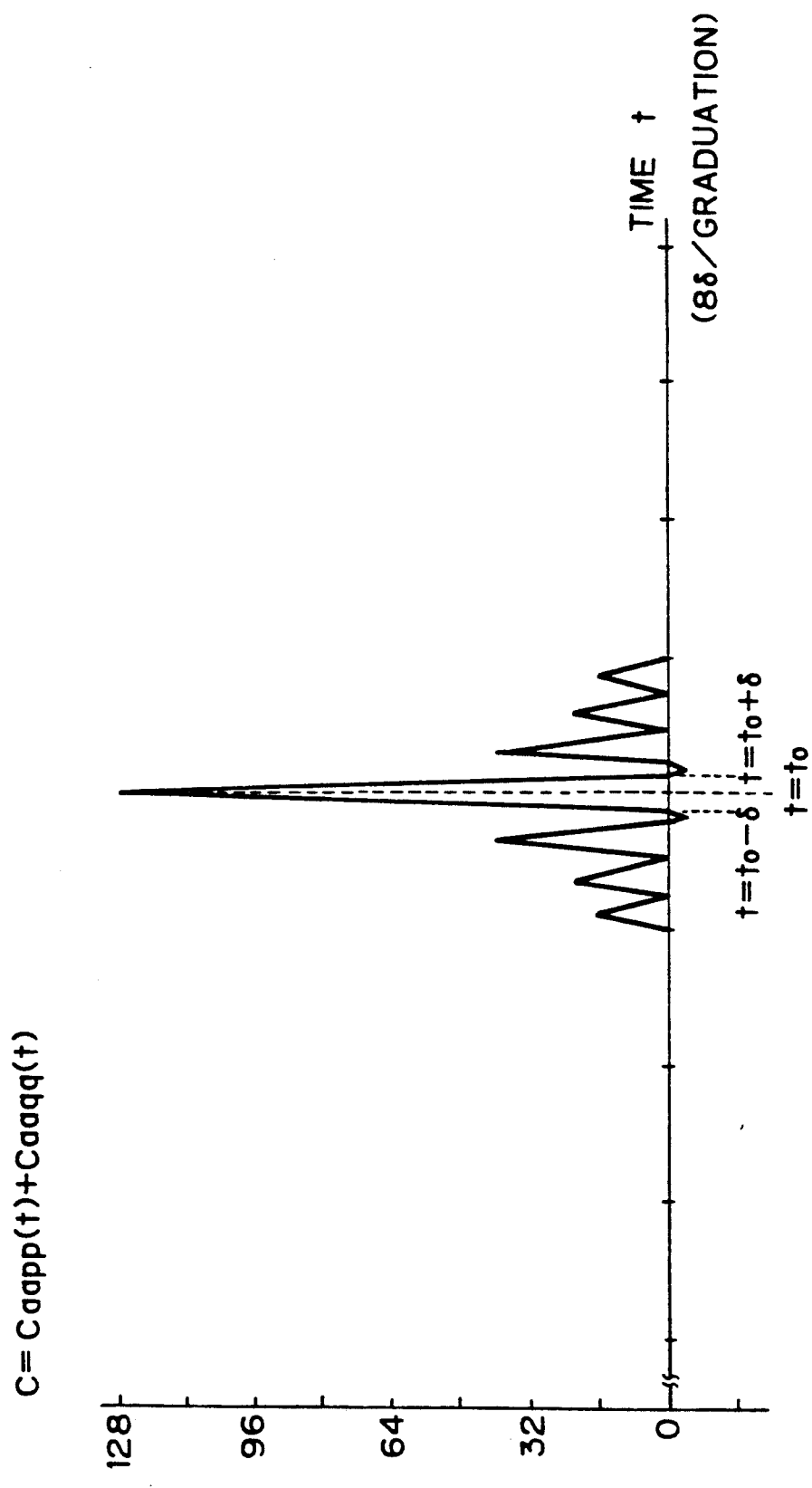
FIG. 42 is a waveform diagram illustrating a composite compressed pulse of a modification of the first embodiment.

As seen from FIGS. 20–24, since neither results Cbbpp(t) nor Cbbqq(t) are summed with the results Caapp(t) and Caaqq(t), the compressed pulse C=Caapp(t)+Caaqq(t) has side lobes of certain amplitudes which are not zero as shown in FIG. 42 in comparison with the pulse C=Caapp(t)+Caaqq(t)+Cbbpp(t)+Cbbqq(t) shown in FIG. 24.

In view of equation (11), Caaqq(t) is similarly represented as follows:

$$Caaqq(t) = pqq(0)Aa(t-t_0) + \\ pqq(1)[Aa(t-t_0-Tp) + Aa(t-t_0+Tp)] + \\ pqq(2)[Aa(t-t_0-2Tp) + Aa(t-t_0+2Tp)] + \\ pqq(3)[Aa(t-t_0-3Tp) + Aa(t-t_0+3Tp)]$$

The third and fourth sequences are in the complementary relationships as described above, and thus $ppp(0) = pqq(0)$ $ppp(1) = -pqq(1)$ $ppp(2) = -pqq(2)$ $ppp(3) = -pqq(3)$ Accordingly, $$Caapp(t) + Caaqq(t) = 2ppp(0)Aa(t-t_0) \qquad (12)$$

From equation (12), it is apparent that if the first basic unit compressed pulse $Aa(t-t_0)$ has substantially small side lobes, the compressed pulse C=Caapp(t)+Caaqq(t) has also substantially small side lobes.

Since a Barker sequence is a well-known sequence, a autocorrelation function of which has small side lobes, such a Barker sequence can be employed as the first sequence {a} to reduce the side lobes of the pulse C when the second sequence {b} is not utilized.

Further, modification which does not employ the fourth sequence {q} as well as the second sequence {b}.

In this case, the transmission signal S comprises only the first transmission signal Sap(t), and thus the echo signal R only the first echo signal Rap(t).

The correlation result at the first correlator 11 is only Caap(t) which is fed from the first reference signal Ua(t) and the first echo signal Rap(t). The correlation result, or compressed pulse C at the second correlator 12 is only Caapp(t) as shown in FIG. 20 which is fed from the result Caap(t) and the third reference signal Up(t).

The result Caapp(t) is representable as equation (11). That is, $$Caapp(t) = ppp(0)Aa(t - t_0) +$$
$$ppp(1)[Aa(t - t_0 - Tp) + Aa(t - t_0 + Tp)] +$$
$$ppp(2)[Aa(t - t_0 - 2Tp) + Aa(t - t_0 + 2Tp)] +$$
$$ppp(3)[Aa(t - t_0 - 3Tp) + Aa(t - t_0 + 3Tp)]$$

Although the compressed pulse Caapp(t) has side lobes having certain amplitudes as shown in FIG. 20, it is obvious from the above equation that the amplitudes of the side lobes can be sufficiently lowered, relative to the main lobe at $t=t_0$, if the autocorrelation function value $ppp(0)$ is sufficiently larger than the others $ppp(1)$ through $ppp(3)$ and also if the basic unit compressed pulse $Aa(t-t_0)$ has sufficiently larger amplitude at $t=t_0$ (main lobe) and near thereto than the others at the other time t (side lobes).

Figure 43:
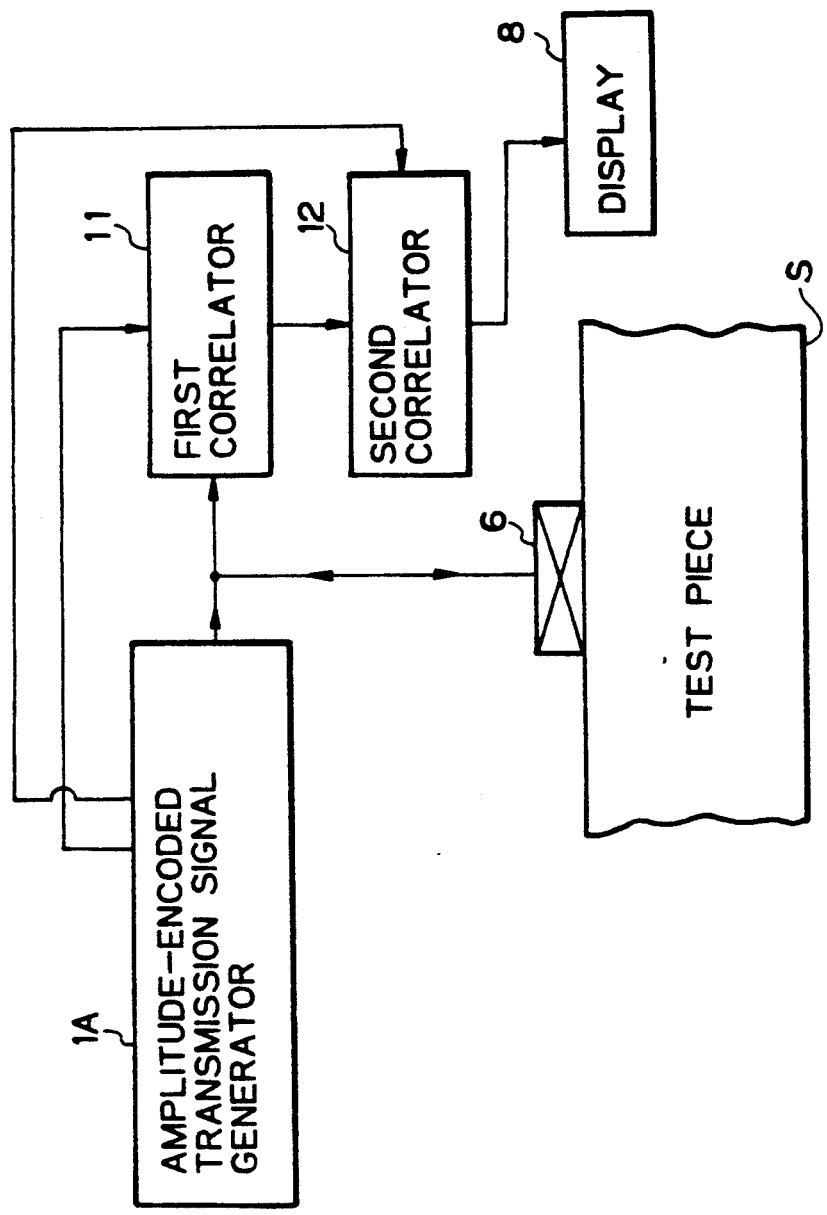
FIG. 43 is a block diagram illustrating a modification of the first embodiment.

The latter condition can obviously be satisfied by the sequence {a} being a Barker sequence, as the first modification. Accordingly, if a Barker sequence is employed as the first sequence {a} and the autocorrelation function $ppp(i)$ of the third sequence {p} has a sufficiently large value at $i=0$ in comparison with the others ($i\neq 0$), the second modification can derive advantages similar to those of the first embodiment. In this case, since the compressed pulse C contains only Caapp(t), the adder 15 in the first embodiment can be neglected as shown in FIG. 43.

It is to be understood that the above modifications explained with regard to the first embodiment can also be applied to the second through sixth embodiments.

In the respective embodiments which have been explained so far, the length M of the first and second sequences {a} and {b} is 8 while the length N of the third and fourth sequences {p} and {q} is 4. For the length M and N, any natural number may be applied.

For example, supposing that the first basic unit signal is used as the first reference signal and there are $K_1$ number of sampling points in the time period δ, let each of the length M and N be any natural number including 1.

In a case of $Tp=M\delta$, the first correlator 11 can be constituted in a similar manner to FIG. 27 by a delay line 11a having $M\times K_1$ number of output taps, $M\times K_1$ number of multipliers 11b connected respectively to the output taps of the delay line 11a and an adder 11c having $M\times K_1$ number of input terminals. The second correlator 12 can be constituted in a similar manner to FIG. 28 by a delay line 12a having $(N-1)\times M\times K_1$ number of output taps, N number of multipliers connected to the output taps of the delay line 12a for every $(M\times K_1)$-th taps, and an adder 12c having N number of input terminals.

Compared to the above-mentioned embodiment, the correlator 10 (FIG. 4) of the conventional apparatus requires a delay line 10a having $M\times N\times K_1$ number of output taps, $M\times N\times K_1$ number of multipliers 10b connected to the respective output taps and an adder 10c having $M\times N\times K_1$ number of input terminals in order to attain a similar effect to that of the above-mentioned embodiment, and thus requires a larger number of multipliers and input terminal of the adder.

Consideration is made next on the case of $Tp>M\delta$ or $Tp<M\delta$. Supposing that there are $K_2$ number of sampling points in the time period Tp in these cases, the first correlator 11 can be constituted in a similar manner to FIG. 27 by a delay line 11a having $M\times K_1$ number of taps, $M\times K_1$ number of multipliers 11b connected to the respective taps of the delay line 11a, and an adder 11c having $M\times K_1$ number of input terminals. The second correlator 12 can be constituted in a similar manner to FIG. 28 by the delay line 12a having $(N-1)\times K_2$ number of taps, and N number of multipliers 12b connected to the output taps of the delay line 12a for every $K_2$-th taps and the adder 12c having N number of the input terminals. This constitution can provide similar advantages to those of the embodiment as described above. That is, a number of the multipliers and input terminals of the adder is decreased in comparison with the corresponding prior art.

It is to be noted that if $M=1$, the waveforms of the first and second basic unit signals are equivalent to unit waveforms such as a rectangular waveform, a quasi-rectangular waveform, a sinusoidal waveform, a waveform having a smooth curve or a vibration waveform. In this case, therefore, the first correlator 11 may be dispensed with in the first and third embodiments. In the second, fourth, fifth and sixth embodiments, the first correlator 11 may be left as a matching filter or a quasi-matching filter. In a case of $N=1$, the second correlator 12 may be dispensed with in the first through sixth embodiments.

Furthermore, in general, supposing that there are $K_3$ number of sampling points within the time duration of the first reference signal and there are $K_2$ number of sampling points within the time duration Tp, the first correlator 11 may be constituted in a similar manner to FIG. 24 by a delay line 11a having $K_3$ number of taps, $K_3$ number of multipliers 11c connected to the respective taps of the delay line 11a and an adder 11c having $K_3$ number of input terminals. The second correlator 12 may be constituted in a similar manner to FIG. 28 by a delay line 12a having $(N-1)\times K_2$ number of taps, N number of multipliers 12b connected to the taps of the delay line 12a for every $K_2$-th taps and the adder 12c having N number of input terminals. This constitution also has the similar function and advantages to those of the embodiment as described above.

In the respective embodiments as described above, the impulse response h(t) is a delta function. The present invention is not limited to these embodiments and a similar function and effect to those of the embodiments may be expected when h(t) is an arbitrary function, for example, a function with waveform portions of vibrations.

In the respective embodiments as described above, the first and second sequences are in the complementary relationships. The present invention is not limited to these embodiments and a similar function and effect to those of the embodiments may be expected when the first and second basic unit compressed pulses are in the complementary relationships.

Further, in the respective embodiments as described above, such embodiments have been described in which the third and fourth sequences are in the complementary relationships, but the present invention is not also limited to them. A similar function and effect to those of the embodiments may be attained if the result of summation of the first and third compressed pulses and the results of summation of the second and fourth compressed pulses are in the complementary relationships under that the first and second basic unit compressed pulses are in the complementary relationships.

Although the present invention has been explained with respect to application to an ultrasonic flaw detector apparatus, it can be applied to other apparatuses such as an ultrasonic diagnostic apparatus.

Also, although the explanation has been made on such a situation where the test piece S is in contact with the ultrasonic probe 6, the test piece may need not be in contact with the ultrasonic probe. In this instance, transmission and reception of the ultrasonic wave between the ultrasonic probe and the test piece may be effected through such a coupling medium as water.

The present invention can also be applied to an ultrasonic wave transmission and reception system utilizing a plurality of probe elements consisting an ultrasonic probe array, and to a transmission and reception system utilizing another wave, for instance an electromagnetic wave.

What is claimed is:

1. An inspection apparatus comprising:
generator means for generating first and second basic unit signals based on respective first and second sequences, and a composite transmission signal comprising first, second, third and fourth transmission signals arranged in sequence, based on said first basic unit signal and a third sequence, said first basic unit signal and a fourth sequence, said second basic unit signal and said third sequence, and said second basic unit signal and said fourth sequence, respectively;
transmission means for transmitting said composite transmission signal generated from said generator means to a target;
reception means for receiving an echo reflected from said target to provide a composite echo signal comprising first, second, third and fourth echo signals corresponding respectively to said first, second, third and fourth transmission signals;
first correlator means for correlation-processing said first and second echo signals provided by said reception means by utilizing a first reference signal based on said first sequence to provide first and second correlation results, and said third and fourth echo signals provided by said reception means by utilizing a second reference signal based on said second sequence to provide third and fourth correlation results;
second correlator means for correlation-processing said first and third correlation results provided by said first correlator means by utilizing a third reference signal based on said third sequence to provide first and second compressed pulses, and said second and fourth correlation results provided by said first correlator means by utilizing a fourth reference signal based on said fourth sequence to provide third and fourth compressed pulses; and
adder means for summing said first, second, third and fourth compressed pulses and Cbbqq(t) provided by said second correlation means to provide a composite compressed pulse having a main lobe and side lobes, whereby the level of the main lobe of said composite compressed pulse becomes satisfactorily large and the level of the side lobes becomes satisfactorily low.

2. An inspection apparatus according to claim 1, wherein said first and second sequences have an identical number of components of first and second kinds and are in a complementary relationship and said third and fourth sequences have an identical number of components of first and second kinds and are in a complementary relationship.

3. An inspection apparatus according to claim 2, wherein said generator means comprises means for amplitude-encoding a wave signal in accordance with said components of said first and second sequences so that said first and second basic unit signals have waveforms amplitude-encoded with said first and second sequences.

4. An inspection apparatus according to claim 3, wherein said wave signal includes a unit rectangular wave signal, and said first and second basic unit signals comprise said unit rectangular wave signal allocated to said first kind of components of said first and second sequences, and an inverted unit rectangular wave signal obtained by multiplying said unit rectangular wave signal by $-1$ allocated to said second kind of components of said first and second sequences.

5. An inspection apparatus according to claim 2, wherein said generator means comprises means for phase-encoding a wave signal in accordance with said components of said first and second sequences so that said first and second basic unit signals have waveforms phase-encoded with said first and second sequences, respectively.

6. An inspection apparatus according to claim 5, wherein said wave signal has a unit wave signal, and said first and second basic unit signals comprise said unit wave signal allocated to said first kind of components of said first and second sequences, and an inverted unit wave signal obtained by multiplying said unit wave signal by $-1$ allocated to said second kind of components of said first and second sequences.

7. An inspection apparatus according to claim 6, wherein said unit wave signal is a unit rectangular wave signal.

8. An inspection apparatus according to claim 6, wherein said unit wave signal is an oscillation wave signal.

9. An inspection apparatus according to claim 2, wherein said first and second transmission signals comprise said first basic unit signal allocated to said first kind of components of said third and fourth sequences, and an inverted first basic unit signal obtained by multiplying said first basic unit signal by $-1$ allocated to said second kind of components of said third and fourth sequences, respectively, and said third and fourth transmission signals comprise said second basic unit signal allocated to said first kind of components of said third and fourth sequences and an inverted second basic units signal obtained by multiplying said second basic unit signal by $-1$ allocated to said second kind of components of said third and fourth sequences, respectively.

10. An inspection apparatus according to claim 1, wherein said first and second reference signals have waveforms similar to waveforms of said first and second basic unit signals, respectively.

11. An inspection apparatus according to claim 1, wherein said first and second reference signals have waveforms similar to waveforms of echo signals obtained by reflection from said target to said reception means when said transmission means is driven by said first and second basic unit signals, respectively.

12. An inspection apparatus according to claim 1, wherein said third and fourth reference signals have waveforms similar to waveforms of signals obtained by amplitude-encoding a wave signal with said third and fourth sequences, respectively.

13. An inspection apparatus comprising:
generator means for generating a basic unit signal based on a first sequence, and a composite transmission signal comprising first and second transmission signals arranged in sequence, based on said basic unit signal and a second sequence and said basic unit signal and a third sequence respectively;
transmission means for transmitting said composite transmitting signal generated from said generator means to a target;
reception means for receiving an echo reflected from said target to provide a composite echo signal comprising first and second echo signals corresponding to said respective first and second transmission signals;
first correlator means for correlation-processing said first and second echo signals provided by said reception means by utilizing a first reference signal based on said first sequence to provide first and second correlation results;
second correlator means for correlation-processing said second correlation results provided by said first correlator means by utilizing second and third reference signals based on said second and third sequences to provide first and second compressed pulses respectively; and
adder means for summing said compressed pulses provided by said second correlator means to provide a composite compressed pulse having a main lobe and side lobes whereby the level of the main lobe of said composite compressed pulse becomes satisfactorily large and the level of the side lobes becomes satisfactorily low.

14. An inspection apparatus according to claim 13, wherein said first sequence is a Barker sequence having first and second kinds of components, and said second and third sequences have an identical number of components of first and second kinds and are in a complementary relationship.

15. An inspection apparatus according to claim 14, wherein said generator means comprises means for amplitude-encoding a wave signal in accordance with said components of said first sequence so that said basic unit signal has a waveform amplitude-encoded with said first sequence.

16. An inspection apparatus according to claim 15, wherein said wave signal is a unit rectangular wave signal, and said basic unit signal comprises said unit rectangular wave signal allocated to said first kind of components of said first sequence, and an inverted unit rectangular wave signal, obtained by multiplying said unit rectangular wave signal by −1, allocated to said second kind of components of said first sequence.

17. an inspection apparatus according to claim 14, wherein said generator means comprising means for phase-encoding a wave signal in accordance with said components of said first sequence so that said basic unit signal has a waveform phase-encoded with said first sequence.

18. An inspection apparatus according to claim 17, wherein said wave signal is a unit wave signal, and said basic unit signal comprises said wave signal allocated to said first kind of components of said first sequence and an inverted unit wave signal obtained by multiplying said unit wave signal by −1, allocated to said second kind of components of said first sequence.

19. An inspection apparatus according to claim 18, wherein said unit wave signal is a unit rectangular wave signal.

20. An inspection apparatus according to claim 18, wherein said unit wave signal is an oscillation wave signal.

21. An inspection apparatus according to claim 14, wherein said first and second transmission signals comprise said basic unit signal allocated to said first kind components of said second and third sequences, and an inverted basic unit signal obtained by multiplying said basic unit signal by −1 allocated to said second kind components of said second and third sequences, respectively.

22. An inspection apparatus according to claim 13, wherein said first reference signal has a waveform similar to a waveform of said basic unit signal.

23. An inspection apparatus according to claim 13, wherein said first reference signal has a waveform similar to a waveform of an echo signal obtained by reflection from said target to said reception means when said transmission means is driven by said basic unit signal.

24. An inspection apparatus according to claim 13, wherein said second and third reference signals have waveforms similar to waveforms of signals obtained by amplitude-encoding a wave signal with said second and third sequences and, respectively.

25. An inspection apparatus comprising:
generator means for generating a basic unit signal based on a first sequence and a transmission signal based on said basic unit signal and a second sequence;
transmission means for transmitting said transmission signal generated from said generator means to a target;
reception means for receiving an echo reflected from said target to provide an echo signal corresponding to said transmission signal;
first correlator means for correlation-processing said echo signal, provided by said reception means by utilizing a first reference signal based on said first sequence to provide a correlation result; and
second correlator means for correlation-processing said correlation result provided by said first correlator means by utilizing a second reference signal based on said second sequence to provide a compressed pulse.

26. An inspection apparatus according to claim 25, wherein said first sequence is a Barker sequence having first and second kinds of components, and said second sequence has the first and second kinds of components and has an autocorrelation function having a sufficiently large main lobe.

27. An inspection apparatus according to claim 26, wherein said generator means comprises means for amplitude-encoding a wave signal in accordance with said components of said first sequence so that said basic unit signal has a waveform amplitude-encoded with said first sequence.

28. An inspection apparatus according to claim 27, wherein said wave signal is a unit rectangular wave signal, and said basic unit signal comprises said unit rectangular wave signal allocated to said first kind of components of said first sequence, and an inverted unit rectangular wave signal obtained by multiplying said unit rectangular wave signal by −1, allocated to said second kind of components of said first sequence.

29. An inspection apparatus according to claim 27, wherein said generator means comprises means for phase-encoding a wave signal in accordance with said components of said first sequence so that said basic unit signal has a waveform phase-encoded with said first sequence.

30. An inspection apparatus according to claim 29, wherein said wave signal is a unit wave signal, and said basic unit signal comprises said unit wave signal allocated to said first kind of components of said first sequence and an inverted unit wave signal obtained by multiplying said unit wave signal by −1 allocated to said second kind of components of said first sequence.

31. An inspection apparatus according to claim 30, wherein said unit wave signal is a unit rectangular wave signal.

32. An inspection apparatus according to claim 30, wherein said unit wave signal is an oscillation wave signal.

33. An inspection apparatus according to claim 26, wherein said transmission signals comprises said basic unit signal allocated to said first kind of components of said second sequence and an inverted basic unit signal obtained by multiplying said basic unit signal by −1 allocated to said second kind of components of said second sequence.

34. An inspection apparatus according to claim 25, wherein said first reference signal has a waveform similar to a waveform of said basic unit signal.

35. An inspection apparatus according claim 25, wherein said first reference signal has a waveform similar to a waveform of an echo signal obtained by reflection from said target to said reception means when said transmission means is driven by said basic unit signal.

36. An inspection apparatus according to claim 25, wherein said second reference signal has a waveform similar to a waveform of a signal obtained by amplitude-encoding a wave signal with said second sequence.

* * * * *